US012668607B2

(12) United States Patent
Peng et al.

(10) Patent No.: US 12,668,607 B2
(45) Date of Patent: Jun. 30, 2026

(54) HETEROCYCLIC AMIDE COMPOUND, PREPARATION METHOD THEREFOR AND USE THEREOF

(71) Applicant: SHANGHAI JEYOU PHARMACEUTICAL CO., LTD., Shanghai (CN)

(72) Inventors: Jianbiao Peng, Shanghai (CN); Shuchun Guo, Shanghai (CN); Yang Liu, Shanghai (CN); Haibing Guo, Shanghai (CN)

(73) Assignee: SHANGHAI JEYOU PHARMACEUTICAL CO., LTD., Shanghai (CN)

( * ) Notice: Subject to any disclaimer, the term of this patent is extended or adjusted under 35 U.S.C. 154(b) by 1179 days.

(21) Appl. No.: 17/629,522

(22) PCT Filed: Jul. 24, 2020

(86) PCT No.: PCT/CN2020/104506

§ 371 (c)(1),
(2) Date: Jan. 24, 2022

(87) PCT Pub. No.: WO2021/013250

PCT Pub. Date: Jan. 28, 2021

(65) Prior Publication Data

US 2022/0267364 A1 Aug. 25, 2022

(30) Foreign Application Priority Data

Jul. 25, 2019 (CN) ........................ 201910676596.X
Jul. 17, 2020 (CN) ........................ 202010695694.0

(51) Int. Cl.
*C07H 15/26* (2006.01)
*A61P 35/00* (2006.01)
(Continued)

(52) U.S. Cl.
CPC .............. *C07H 15/26* (2013.01); *A61P 35/00* (2018.01); *C07D 403/14* (2013.01); *C07D 471/10* (2013.01); *C07D 491/107* (2013.01)

(58) Field of Classification Search
CPC ....... C07H 15/26; A61P 35/00; C07D 403/14; C07D 471/10; C07D 491/107
See application file for complete search history.

(56) References Cited

U.S. PATENT DOCUMENTS

2018/0105514 A1 4/2018 Mehlmann et al.
2020/0330556 A1 10/2020 Pesiridis et al.
2021/0139473 A1 5/2021 Charnley et al.

FOREIGN PATENT DOCUMENTS

CN 109071514 A 12/2018
EP 3848366 A1 7/2021
(Continued)

OTHER PUBLICATIONS

Calvaresi et al. (Chem. Sci., 2013, vol. 4, pp. 2319-2333)(Year: 2013).*
(Continued)

*Primary Examiner* — Scarlett Y Goon
*Assistant Examiner* — Sarah Grace Hibshman
(74) *Attorney, Agent, or Firm* — SZDC Law PC

(57) ABSTRACT

Disclosed in the present invention are a compound shown in formula (IA), an optical isomer thereof and a pharmaceuti-
(Continued)

cally acceptable salt thereof, and the use of the compound as a STING agonist.

(IA)

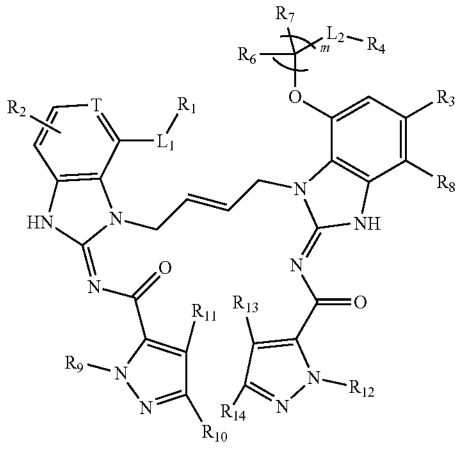

16 Claims, 1 Drawing Sheet

(51) Int. Cl.

| | |
|---|---|
| ***C07D 403/14*** | (2006.01) |
| ***C07D 471/10*** | (2006.01) |
| ***C07D 491/107*** | (2006.01) |

(56) References Cited

FOREIGN PATENT DOCUMENTS

| | | | |
|---|---|---|---|
| JP | 2019510796 | A | 4/2019 |
| JP | 2020536105 | A | 12/2020 |
| WO | 2017175147 | A1 | 10/2017 |
| WO | 2019069275 | A1 | 4/2019 |
| WO | 2019134705 | A1 | 7/2019 |
| WO | 2020042995 | A1 | 3/2020 |
| WO | 2020214858 | A1 | 10/2020 |
| WO | 2021202984 | A1 | 10/2021 |

OTHER PUBLICATIONS

Lewandowska et al. (2017, Ann. Agric. Environ. Med. vol. 26, pp. 1-7) (Year: 2017).*

McArthur, D.B. (2019, Nurs. Clin. N. Am. vol. 54; pp. 297-311) (Year: 2019).*

Chinese Second Office Action issued in Chinese Patent Application No. 202010727314.7 dated Jul. 27, 2023.

Partial supplementary European search report issued in European Patent Application No. 20844297.0 dated Aug. 4, 2023.

Extended European search report issued in European Patent Application No. 20844297.0 dated Nov. 30, 2023.

Taiwan First Office Action issued in Taiwan Patent Application No. 109125104 dated Oct. 12, 2023.

First Office Action issued in Chinese Patent Application No. 202010727314.7 dated Jan. 4, 2023.

First Office Action issued in Chinese Patent Application No. 202080053824.9 dated Jan. 19, 2023.

First Office Action issued in Japanese Patent Application No. 202250537.9 dated Apr. 4, 2023.

International Search Report issued on Jul. 24, 2020in International Patent Application No. PCT/CN2020/104506.

Written Opinion of the International Searching Authority issued Jul. 24, 2020 in International Patent Application No. PCT/CN2020/104506.

Office Action dated Jun. 14, 2024 issued in Taiwanese Patent Application No. 109125104.

Second Office Action issued in Japanese Patent Application No. 2022505379 dated Jan. 9, 2024.

First Office Action after Reexamination in Taiwan issued in Taiwan Patent Application No. 109125104 dated Mar. 7, 2025.

* cited by examiner

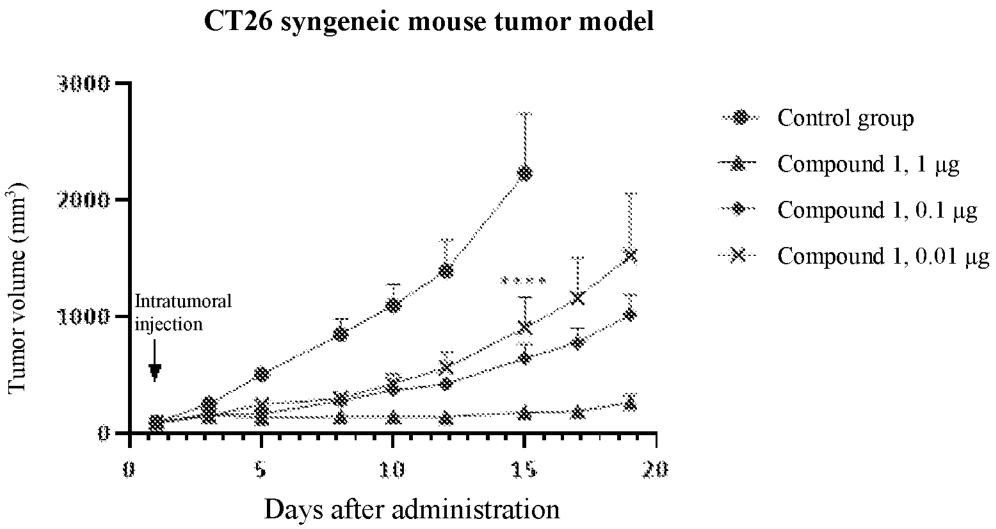
CT26 syngeneic mouse tumor model
3000
2000
1000
0
Tumor volume (mm3)
Intratumoral
injection
****
0
5
10
15
20
Days after administration
Control group
Compound 1, 1 μg
Compound 1, 0.1 μg
Compound 1, 0.01 μg

HETEROCYCLIC AMIDE COMPOUND, PREPARATION METHOD THEREFOR AND USE THEREOF

The present application is the National Stage Application of PCT/CN2020/104506, filed on Jul. 24, 2020, which claims the priority to:

CN 201910676596.X, filed on Jul. 25, 2019; and

CN 202010695694.0, filed on Jul. 17, 2020.

TECHNICAL FIELD

The present disclosure relates to a compound of formula (IA), an optical isomer thereof and a pharmaceutically acceptable salt thereof, and use of the compound as a STING agonist.

BACKGROUND

For a long time, researchers have attempted to completely eliminate tumor cells by activating the immune system of patients so that their own immune system can effectively fight against tumors. However, the probability of spontaneous remission of tumors is very low, and therefore most patients cannot benefit from it. In the 1960s and 1970s, therapeutic methods, such as BCG vaccine injection and non-specific immune enhancement therapy, have appeared. In the 1980s, interferon and IL-2, which are capable of activating T cells and NK cells, have also been tried for cancer treatment, but these methods still have many limitations, such as very short half-life of exogenous cytokines in blood, which must be compensated with frequent dosing and high doses. Non-specific activation of the immune system results in inflammatory responses in normal tissues, cytokine storms, etc., and thus many therapies have very strong toxic side effects. Therapy targeting STING, as an immunomodulatory agent that triggers the production of specific therapeutically beneficial cytokines in vivo, has raised hopes for solving this problem.

It is currently known that human STING is activated in three ways: 1) activation by binding exogenous (3',3') cyclic dinucleotides (c-diGMP, c-diAMP and c-GAMP) released by invading bacteria or archaea, which shows that STING has a role in innate immune activation in anti-infection; 2) activation by binding (2',3') cyclic guanosine adenosine monophosphate (2',3' c-GAMP) which is an endogenous cyclic dinucleotides induced by cyclic GMP-AMP synthase (cGAS) in the presence of exogenous double-stranded DNA (e.g., released by invading bacteria, viruses or protozoa) or self-DNA in mammals, which shows that STING has a role in innate immune activation induced by endogenous or exogenous DNA; 3) activation by binding a synthetic ligand.

STING acts as a cytoplasmic DNA sensor, and its activation can lead to activation of both the downstream IRF3 and NF-κB pathways to activate the immune system. The activation of NF-κB pathway leads to the activation of a series of downstream proinflammatory cytokines, while the activation of IRF3 pathway leads to the activation of type I interferon (IFN-α/β) and the activation of dendritic cells, cytotoxic cells, NK cells and the like, thereby exerting an anti-tumor effect.

DNA in the human body does not generally activate STING proteins because DNA is generally only present in nucleus (except for mitochondrial DNA). However, if DNA leaks into cytoplasm, it will activate STING, triggering an immune response. It has recently been found that radiation therapy and chemotherapy can also activate STING, which may also result from DNA leakage in dead tumor cells leading to activation of STING.

CONTENT OF THE INVENTION

In one aspect of the present disclosure, provided are a compound of formula (IA), an optical isomer thereof and a pharmaceutically acceptable salt thereof, (IA)

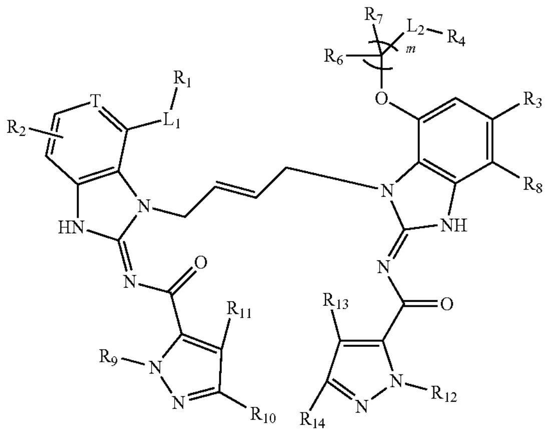

wherein, $L_1$ is selected from the group consisting of —O—, —NH— and a single bond;

$R_1$ is selected from the group consisting of H and $C_{1-6}$ alkyl, wherein the $C_{1-6}$ alkyl is optionally substituted with 1, 2 or 3 R;

$R_2$ and $R_3$ are each independently selected from the group consisting of H,

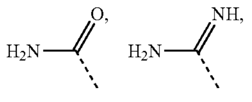

$C_{3-6}$ cycloalkyl, 5-6 membered heterocycloalkyl and 5-6 membered heteroaryl, wherein the $C_{3-6}$ cycloalkyl, 5-6 membered heterocycloalkyl or 5-6 membered heteroaryl is optionally substituted with 1, 2 or 3 R;

$L_2$ is selected from the group consisting of a single bond, —O—, —S—, —NH— and —NHC(═O)—;

$R_4$ is selected from the group consisting of

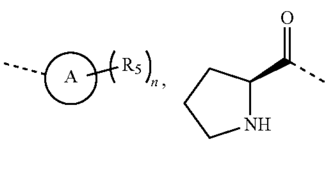

and $C_{1-6}$ alkyl-C(═O)—, wherein the $C_{1-6}$ alkyl-C(═O)— is optionally substituted with 1, 2 or 3 R;

ring A is selected from the group consisting of 4-10 membered heterocycloalkyl and $C_{3-10}$ cycloalkyl;

n is selected from the group consisting of 0, 1, 2, 3, 4, 5 and 6;

m is selected from the group consisting of 1, 2, 3, 4, 5 and 6;

$R_5$ is independently selected from the group consisting of halogen, $N_3$, OH, SH, $NH_2$, CN,

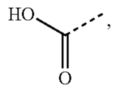

$C_{1-6}$ alkyl, $C_{1-6}$ alkoxy, $C_{1-6}$ alkylthio, $C_{1-6}$ alkylamino and 5-6 membered heterocycloalkyl-$L_3$-, wherein the $C_{1-6}$ alkyl, $C_{1-6}$ alkoxy, $C_{1-6}$ alkylthio or $C_{1-6}$ alkylamino is optionally substituted with 1, 2 or 3 R, and the 5-6 membered heterocycloalkyl-$L_3$- is optionally substituted with 1, 2, 3 or 4 R;

$L_3$ is selected from the group consisting of —O—, —S—, —NH— and —$CH_2$—;

$R_6$ and $R_7$ are each independently selected from the group consisting of H, halogen, $N_3$, OH, SH, $NH_2$, CN,

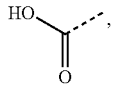

$C_{1-6}$ alkyl, $C_{1-6}$ alkoxy, $C_{1-6}$ alkylthio and $C_{1-6}$ alkylamino, wherein the $C_{1-6}$ alkyl, $C_{1-6}$ alkoxy, $C_{1-6}$ alkylthio or $C_{1-6}$ alkylamino is optionally substituted with 1, 2 or 3 R;

$R_8$ is selected from the group consisting of H, halogen, $N_3$, OH, SH, $NH_2$, CN,

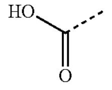

and $C_{1-6}$ alkyl, wherein the $C_{1-6}$ alkyl is optionally substituted with 1, 2 or 3 R;

or, $R_3$ and $R_8$ are linked to form a 5-6 membered heterocyclic ring;

$R_9$ and $R_{12}$ are each independently selected from the group consisting of H and $C_{1-6}$ alkyl, wherein the $C_{1-6}$ alkyl is optionally substituted with 1, 2 or 3 R;

$R_{10}$, $R_{11}$, $R_{13}$ and $R_{14}$ are each independently selected from the group consisting of H, halogen, $N_3$, OH, SH, $NH_2$, CN and $C_{1-6}$ alkyl, wherein the $C_{1-6}$ alkyl is optionally substituted with 1, 2 or 3 R;

or, $R_9$ and $R_{13}$ are linked to form a carbon chain comprising 3-7 carbon atoms;

T is selected from the group consisting of N and CH;

R is independently selected from the group consisting of H, halogen, $N_3$, OH, SH, $NH_2$, CN,

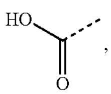, 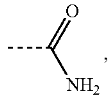, 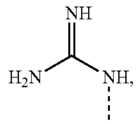

$C_{1-6}$ alkyl, $C_{1-6}$ alkoxy, $C_{1-6}$ alkylthio, $C_{1-6}$ alkylamino, 5-6 membered heterocycloalkyl, phenyl and 5-10 membered heteroaryl, wherein the $C_{1-6}$ alkyl, $C_{1-6}$ alkoxy, $C_{1-6}$ alkylthio, $C_{1-6}$ alkylamino, 5-6 membered heterocycloalkyl, phenyl or 5-10 membered heteroaryl is optionally substituted with 1, 2 or 3 R';

R' is selected from the group consisting of H, F, Cl, Br, I, OH, $NH_2$ and $CH_3$;

the 5-6 membered heterocycloalkyl, 5-6 membered heteroaryl, 4-10 membered heterocycloalkyl or 5-10 membered heteroaryl contains 1, 2 or 3 heteroatoms or heteroatom groups independently selected from the group consisting of —O—, —NH—, —S— and N.

In some embodiments of the present disclosure, provided are the compound, the optical isomer thereof and the pharmaceutically acceptable salt thereof described above, selected from the group consisting of:

(IB)

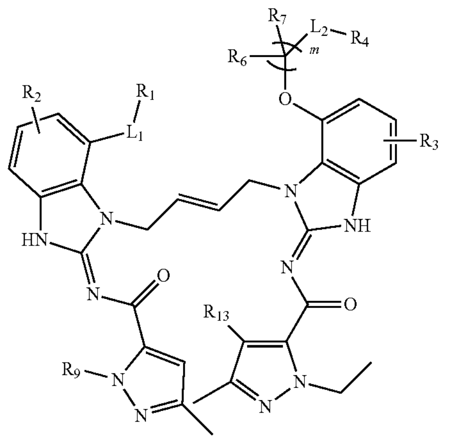

wherein, $L_1$ is selected from the group consisting of —O—, —NH— and a single bond;

$R_1$ is selected from the group consisting of H and $C_{1-6}$ alkyl, wherein the $C_{1-6}$ alkyl is optionally substituted with 1, 2 or 3 R;

$R_2$ and $R_3$ are each independently selected from the group consisting of H,

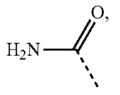 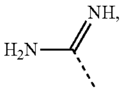

$C_{3-6}$ cycloalkyl, 5-6 membered heterocycloalkyl and 5-6 membered heteroaryl, wherein the $C_{3-6}$ cycloalkyl, 5-6 membered heterocycloalkyl or 5-6 membered heteroaryl is optionally substituted with 1, 2 or 3 R;

$L_2$ is selected from the group consisting of a single bond, —O—, —S—, —NH— and —NHC(═O)—;

$R_4$ is selected from the group consisting of

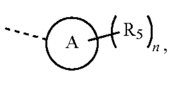 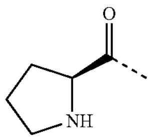

and $C_{1-6}$ alkyl-C(═O)—, wherein the $C_{1-6}$ alkyl-C(═O)— is optionally substituted with 1, 2 or 3 R;

ring A is selected from the group consisting of 5-10 membered heterocycloalkyl and $C_{3-10}$ cycloalkyl;

n is selected from the group consisting of 0, 1, 2, 3, 4, 5 and 6;

m is selected from the group consisting of 1, 2, 3, 4, 5 and 6;

$R_5$ is independently selected from the group consisting of halogen, $N_3$, OH, SH, $NH_2$, CN,

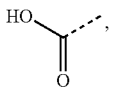

$C_{1-6}$ alkyl, $C_{1-6}$ alkoxy, $C_{1-6}$ alkylthio, $C_{1-6}$ alkylamino and 5-6 membered heterocycloalkyl-$L_3$-, wherein the $C_{1-6}$ alkyl, $C_{1-6}$ alkoxy, $C_{1-6}$ alkylthio or $C_{1-6}$ alkylamino is optionally substituted with 1, 2 or 3 R, and the 5-6 membered heterocycloalkyl-$L_3$- is optionally substituted with 1, 2, 3 or 4 R;

$L_3$ is selected from the group consisting of —O—, —S—, —NH— and —$CH_2$—;

$R_6$ and $R_7$ are each independently selected from the group consisting of H, halogen, $N_3$, OH, SH, $NH_2$, CN,

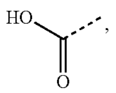

$C_{1-6}$ alkyl, $C_{1-6}$ alkoxy, $C_{1-6}$ alkylthio and $C_{1-6}$ alkylamino, wherein the $C_{1-6}$ alkyl, $C_{1-6}$ alkoxy, $C_{1-6}$ alkylthio or $C_{1-6}$ alkylamino is optionally substituted with 1, 2 or 3 R;

$R_9$ is independently selected from the group consisting of H and $C_{1-6}$ alkyl, wherein the $C_{1-6}$ alkyl is optionally substituted with 1, 2 or 3 R;

$R_{13}$ is independently selected from the group consisting of H, halogen, $N_3$, OH, SH, $NH_2$, CN and $C_{1-6}$ alkyl, wherein the $C_{1-6}$ alkyl is optionally substituted with 1, 2 or 3 R;

or, $R_9$ and $R_{13}$ are linked to form a carbon chain comprising 3-7 carbon atoms;

R is independently selected from the group consisting of H, halogen, $N_3$, OH, SH, $NH_2$, CN,

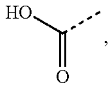 , 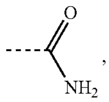 , 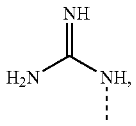

$C_{1-6}$ alkyl, $C_{1-6}$ alkoxy, $C_{1-6}$ alkylthio, $C_{1-6}$ alkylamino, 5-6 membered heterocycloalkyl, phenyl and 5-10 membered heteroaryl, wherein the $C_{1-6}$ alkyl, $C_{1-6}$ alkoxy, $C_{1-6}$ alkylthio, $C_{1-6}$ alkylamino, 5-6 membered heterocycloalkyl, phenyl or 5-10 membered heteroaryl is optionally substituted with 1, 2 or 3 R';

R' is selected from the group consisting of H, F, Cl, Br, I, OH, $NH_2$ and $CH_3$;

the 5-6 membered heterocycloalkyl, 5-6 membered heteroaryl, 5-10 membered heterocycloalkyl or 5-10 membered heteroaryl contains 1, 2 or 3 heteroatoms or heteroatom groups independently selected from the group consisting of —O—, —NH—, —S— and N.

In some embodiments of the present disclosure, provided are the compound, the optical isomer thereof and the pharmaceutically acceptable salt thereof described above, selected from the group consisting of:

(I)

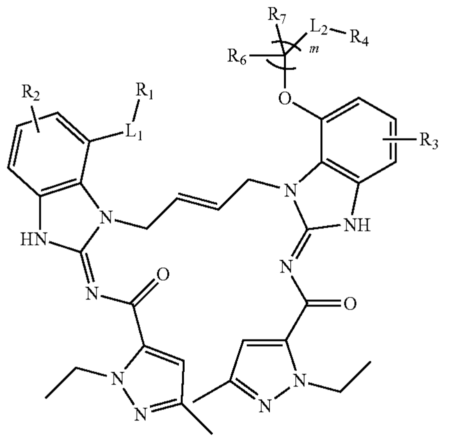

wherein, $L_1$ is selected from the group consisting of —O—, —NH— and a single bond;

$R_1$ is selected from the group consisting of H and $C_{1-6}$ alkyl, wherein the $C_{1-6}$ alkyl is optionally substituted with 1, 2 or 3 R;

$R_2$ and $R_3$ are each independently selected from the group consisting of H,

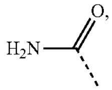 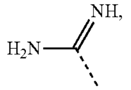

$C_{3-6}$ cycloalkyl, 5-6 membered heterocycloalkyl and 5-6 membered heteroaryl, wherein the $C_{3-6}$ cycloalkyl, 5-6 membered heterocycloalkyl or 5-6 membered heteroaryl is optionally substituted with 1, 2 or 3 R;

$L_2$ is selected from the group consisting of a single bond, —O—, —S—, —NH— and —NHC(=O)—;

$R_4$ is selected from the group consisting of

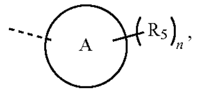 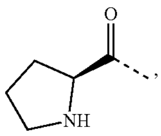

and $C_{1-6}$ alkyl-C(=O)—, wherein the $C_{1-6}$ alkyl-C(=O)— is optionally substituted with 1, 2 or 3 R;

ring A is selected from the group consisting of 5-10 membered heterocycloalkyl and $C_{3-10}$ cycloalkyl;

n is selected from the group consisting of 0, 1, 2, 3, 4, 5 and 6;

m is selected from the group consisting of 1, 2, 3, 4, 5 and 6;

$R_5$ is independently selected from the group consisting of halogen, $N_3$, OH, SH, $NH_2$, CN,

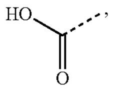

$C_{1-6}$ alkyl, $C_{1-6}$ alkoxy, $C_{1-6}$ alkylthio, $C_{1-6}$ alkylamino and 5-6 membered heterocycloalkyl-$L_3$-, wherein the $C_{1-6}$ alkyl, $C_{1-6}$ alkoxy, $C_{1-6}$ alkylthio or $C_{1-6}$ alkylamino is optionally substituted with 1, 2 or 3 R, and the 5-6 membered heterocycloalkyl-$L_3$- is optionally substituted with 1, 2, 3 or 4 R;

$L_3$ is selected from the group consisting of —O—, —S—, —NH— and —$CH_2$—;

$R_6$ and $R_7$ are each independently selected from the group consisting of H, halogen, $N_3$, OH, SH, $NH_2$, CN,

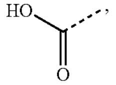

$C_{1-6}$ alkyl, $C_{1-6}$ alkoxy, $C_{1-6}$ alkylthio and $C_{1-6}$ alkylamino, wherein the $C_{1-6}$ alkyl, $C_{1-6}$ alkoxy, $C_{1-6}$ alkylthio or $C_{1-6}$ alkylamino is optionally substituted with 1, 2 or 3 R;

R is independently selected from the group consisting of H, halogen, $N_3$, OH, SH, $NH_2$, CN,

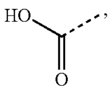 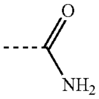, 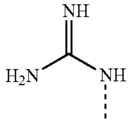, $C_{1-6}$ alkyl, $C_{1-6}$ alkoxy, $C_{1-6}$ alkylthio, $C_{1-6}$ alkylamino, 5-6 membered heterocycloalkyl, phenyl and 5-10 membered heteroaryl, wherein the $C_{1-6}$ alkyl, $C_{1-6}$ alkoxy, $C_{1-6}$ alkylthio, $C_{1-6}$ alkylamino, 5-6 membered heterocycloalkyl, phenyl or 5-10 membered heteroaryl is optionally substituted with 1, 2 or 3 R';

R' is selected from the group consisting of H, F, Cl, Br, I, OH, $NH_2$ and $CH_3$; the 5-6 membered heterocycloalkyl, 5-6 membered heteroaryl, 5-10 membered heterocycloalkyl or 5-10 membered heteroaryl contains 1, 2 or 3 heteroatoms or heteroatom groups independently selected from the group consisting of —O—, —NH—, —S— and N.

In some embodiments of the present disclosure, R is independently selected from the group consisting of H, halogen, $N_3$, OH, SH, $NH_2$, CN,

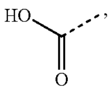 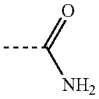, 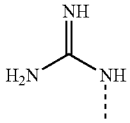, $C_{1-3}$ alkyl, $C_{1-3}$ alkoxy, $C_{1-3}$ alkylthio, $C_{1-3}$ alkylamino, morpholinyl, phenyl, imidazolyl and indolyl, wherein the $C_{1-3}$ alkyl, $C_{1-3}$ alkoxy, $C_{1-3}$ alkylthio, $C_{1-3}$ alkylamino, morpholinyl, phenyl, imidazolyl or indolyl is optionally substituted with 1, 2 or 3 R'; the other variables are as defined in the present disclosure.

In some embodiments of the present disclosure, R is independently selected from the group consisting of H, F, Cl, Br, I, $N_3$, OH, SH, $NH_2$, CN, Me,

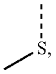 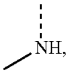 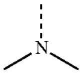, 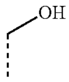, 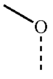, 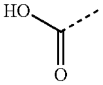,

-continued

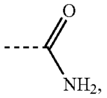 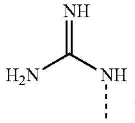, 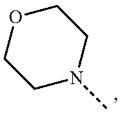, 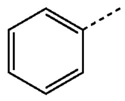,

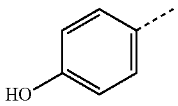, 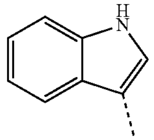 and 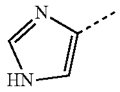;

the other variables are as defined in the present disclosure.

In some embodiments of the present disclosure, $R_1$ is selected from the group consisting of H, Me,

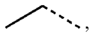, 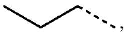, 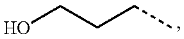,

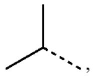, 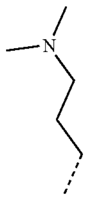 and 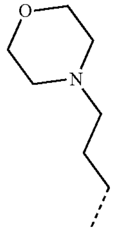;

the other variables are as defined in the present disclosure.

In some embodiments of the present application, the structural unit

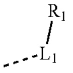

is selected from the group consisting of H,

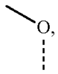, 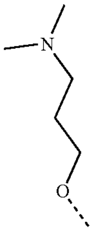 and 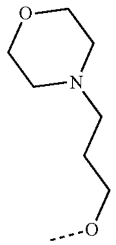;

the other variables are as defined in the present disclosure.

In some embodiments of the present disclosure, ring A is selected from the group consisting of tetrahydro-2H-pyranyl, tetrahydrofuryl, morpholinyl, 2,7-diazaspiro[4.5]decanyl and 2-oxa 6-azaspiro[3.3]heptanyl; the other variables are as defined in the present disclosure.

In some embodiments of the present disclosure, $R_5$ is independently selected from the group consisting of halogen, $N_3$, OH, SH, $NH_2$, CN,

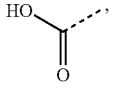

$C_{1-3}$ alkyl, $C_{1-3}$ alkoxy, $C_{1-3}$ alkylthio, $C_{1-3}$ alkylamino, morpholinyl-$L_3$- and tetrahydro-2H-pyranyl-$L_3$-, wherein the $C_{1-3}$ alkyl, $C_{1-3}$ alkoxy, $C_{1-3}$ alkylthio or $C_{1-3}$ alkylamino is optionally substituted with 1, 2 or 3 R, and the morpholinyl-$L_3$- or tetrahydro-2H-pyranyl-$L_3$- is optionally substituted with 1, 2, 3 or 4 R; the other variables are as defined in the present disclosure.

In some embodiments of the present disclosure, $R_5$ is independently selected from the group consisting of F, Cl, Br, I, $N_3$, OH, SH, $NH_2$, CN, —$CH_2NH_2$,

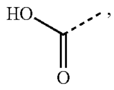 , 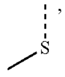 , 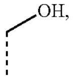 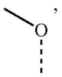 ,

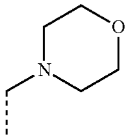 and 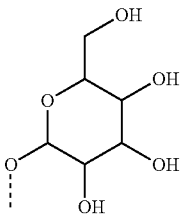 ;

the other variables are as defined in the present disclosure.

In some embodiments of the present disclosure, the structural unit

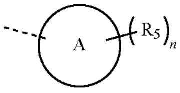

is selected from the group consisting of

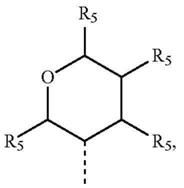 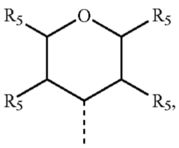 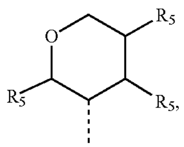

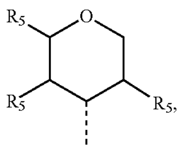 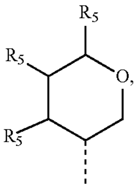 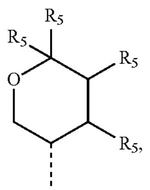

-continued

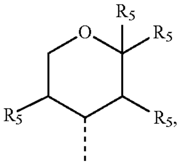 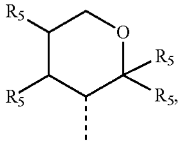 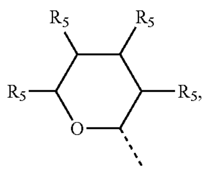

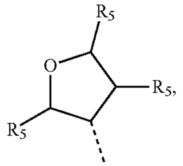 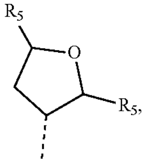 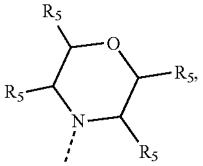

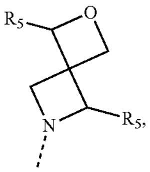 and 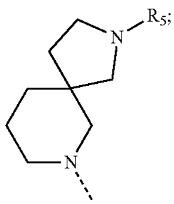

the other variables are as defined in the present disclosure.

In some embodiments of the present disclosure, the structural unit

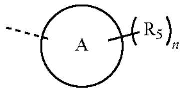

is selected from the group consisting of

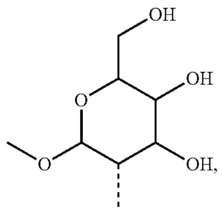 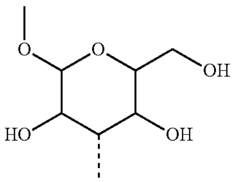 ,

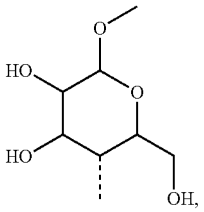 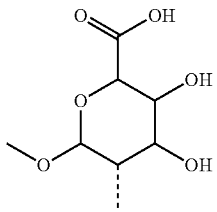 ,

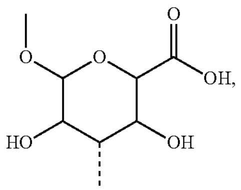 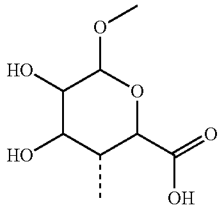 ,

-continued
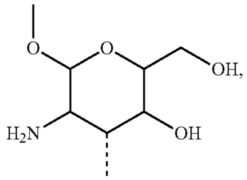 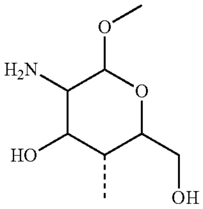 ,
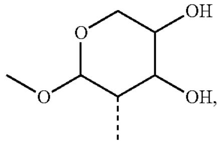 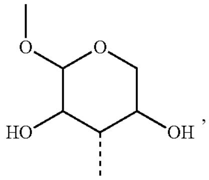 ,
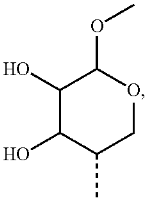 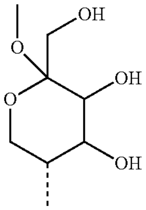 ,
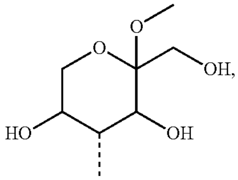 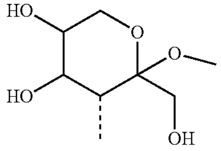 ,
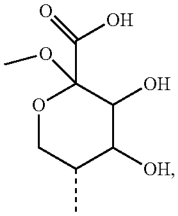 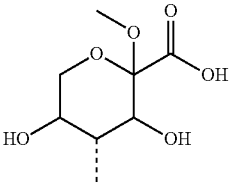 ,
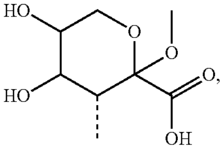 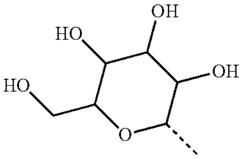 ,
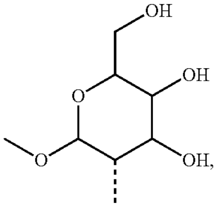 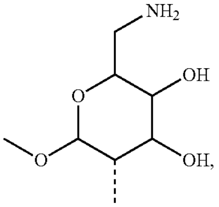
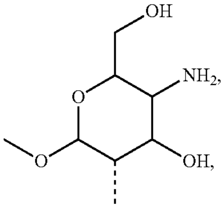 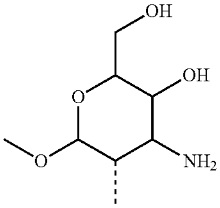 ,
-continued
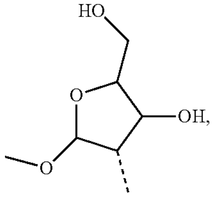 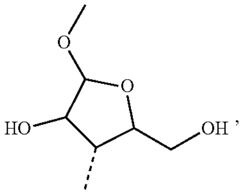
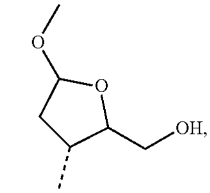 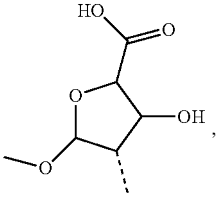
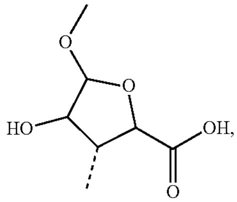 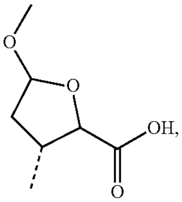 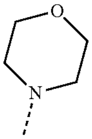 ,
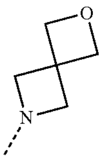 , 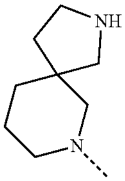 , 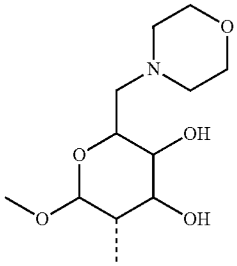 and
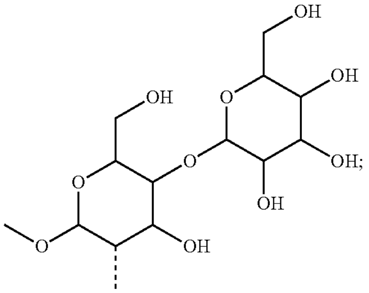
the other variables are as defined in the present disclosure.
In some embodiments of the present disclosure, $R_4$ is selected from the group consisting of
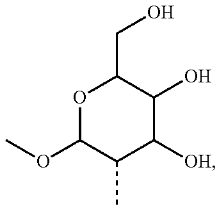 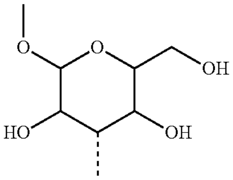 , -continued
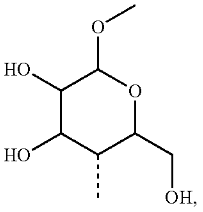
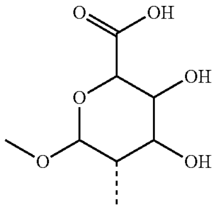
,
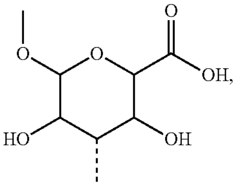
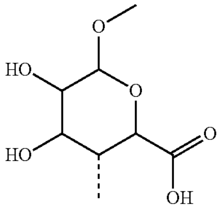
,
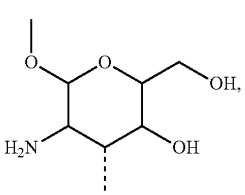
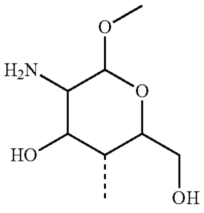
,
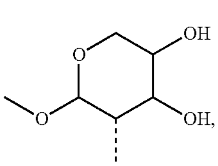
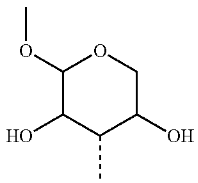
,
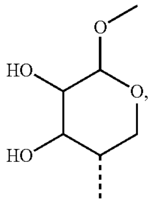
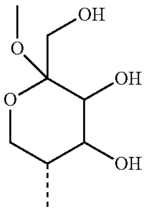
,
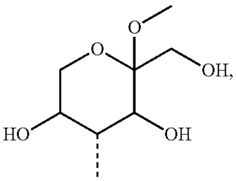
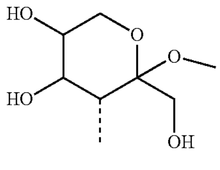
,
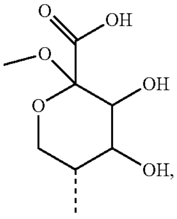
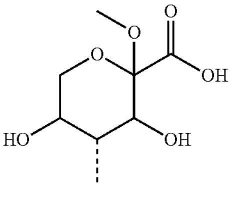
,
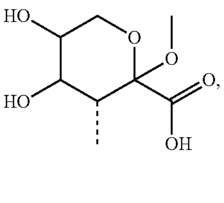
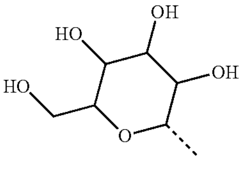
,
-continued
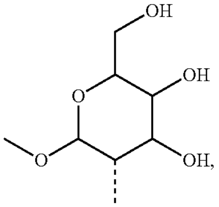
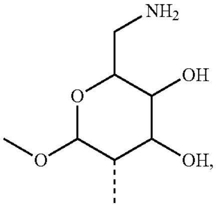
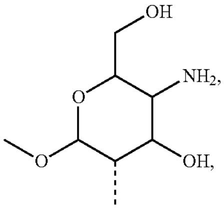
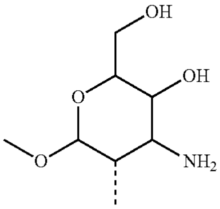
,
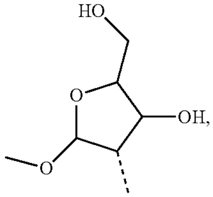
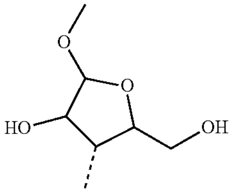
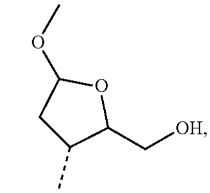
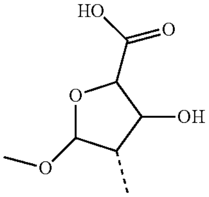
,
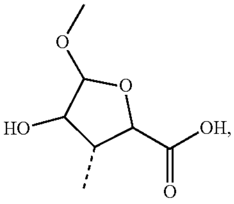
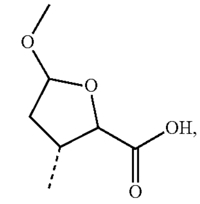
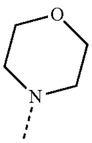
,
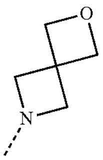
,
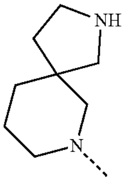
,
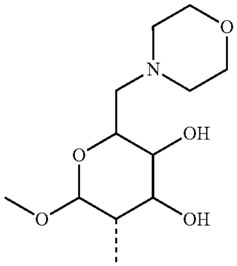
,
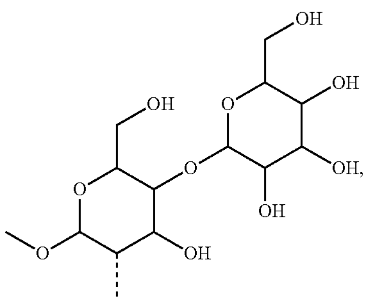
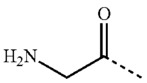
,
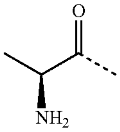
,
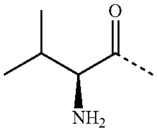
,
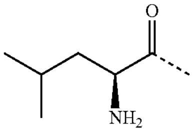
, -continued

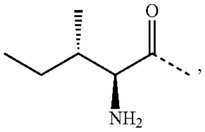, 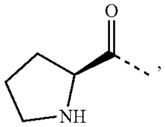,

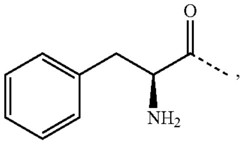, 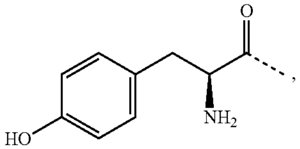,

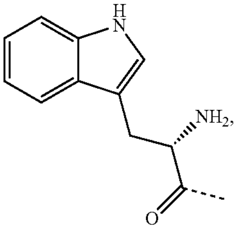 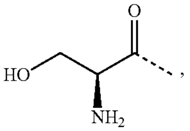,

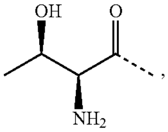, 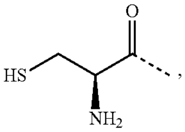,

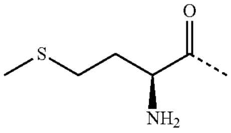, 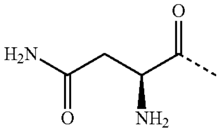,

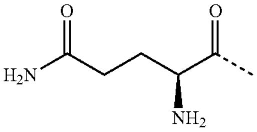, 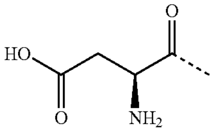,

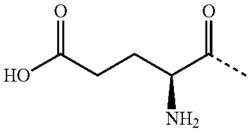,

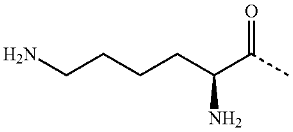,

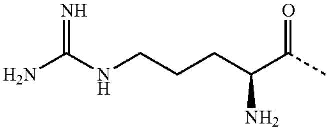,

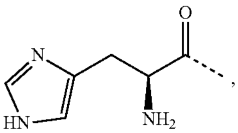, 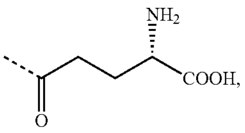

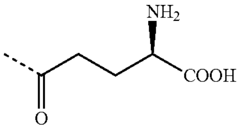 and 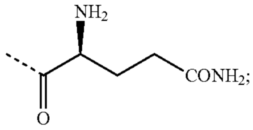

the other variables are as defined in the present disclosure.

In some embodiments of the present disclosure, $R_6$ and $R_7$ are each independently selected from the group consisting of H, halogen, $N_3$, OH, SH, $NH_2$, CN,

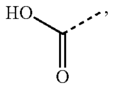

$C_{1-3}$ alkyl, $C_{1-3}$ alkoxy, $C_{1-3}$ alkylthio and $C_{1-3}$ alkylamino, wherein the $C_{1-3}$ alkyl, $C_{1-3}$ alkoxy, $C_{1-3}$ alkylthio or $C_{1-3}$ alkylamino is optionally substituted with 1, 2 or 3 R; the other variables are as defined in the present disclosure.

In some embodiments of the present disclosure, $R_6$ and $R_7$ are each independently selected from the group consisting of H, F, Cl, Br, I, $N_3$, OH, SH, $NH_2$, CN, Me,

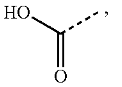, 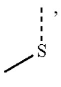, 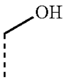 and 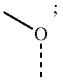;

the other variables are as defined in the present disclosure.

In some embodiments of the present application, the structural unit

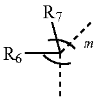

is selected from the group consisting of —$CH_2$—,

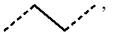, 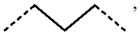, 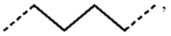,

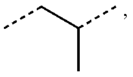, 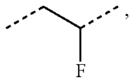, 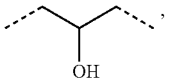,

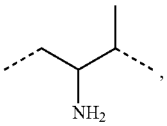, 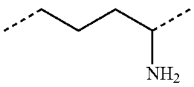 and

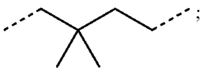;

the other variables are as defined in the present disclosure.

In another aspect of the present disclosure, also provided are a compound of a formula selected from the group consisting of the formulas below, an optical isomer thereof and a pharmaceutically acceptable salt thereof:

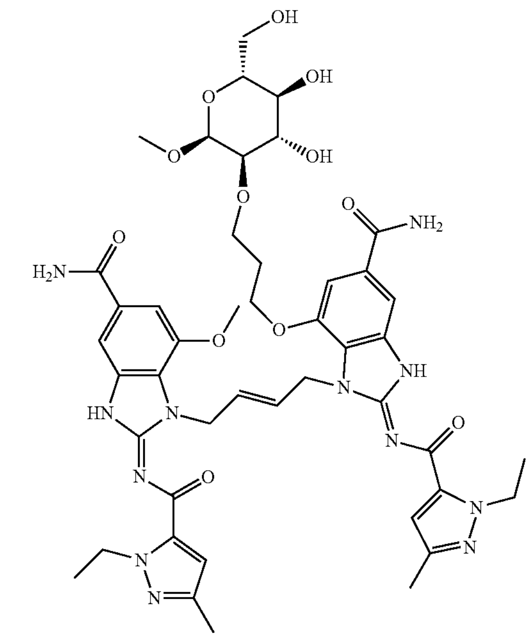
,
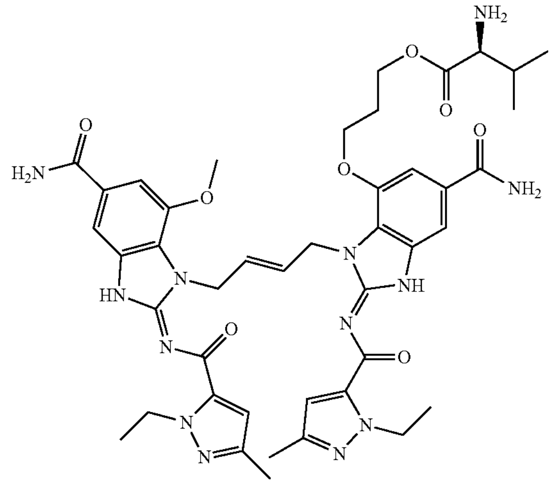
,
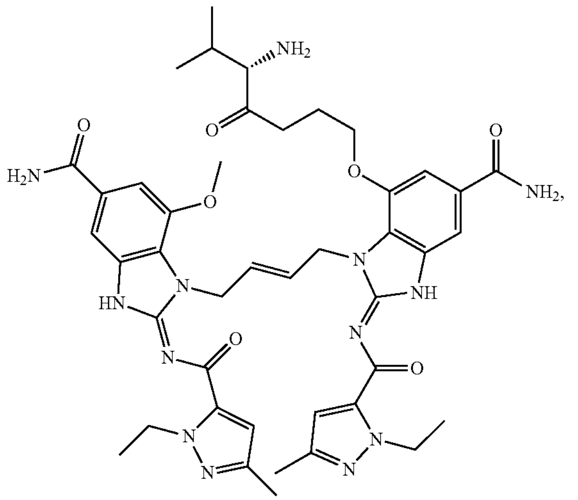
-continued
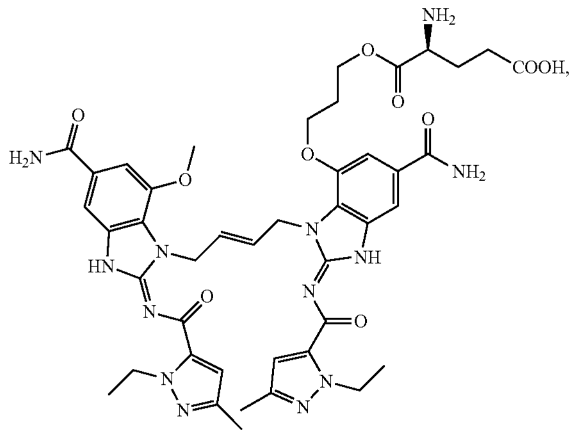
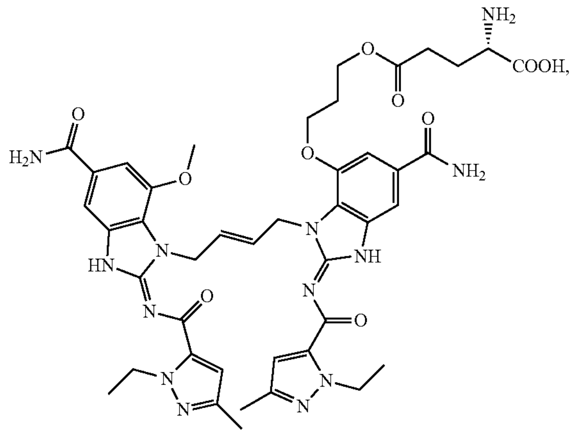
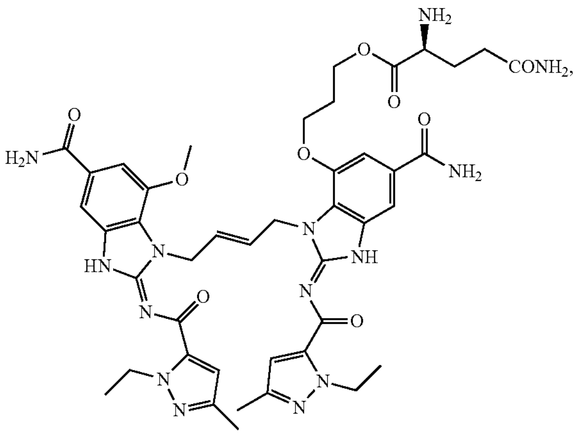

-continued
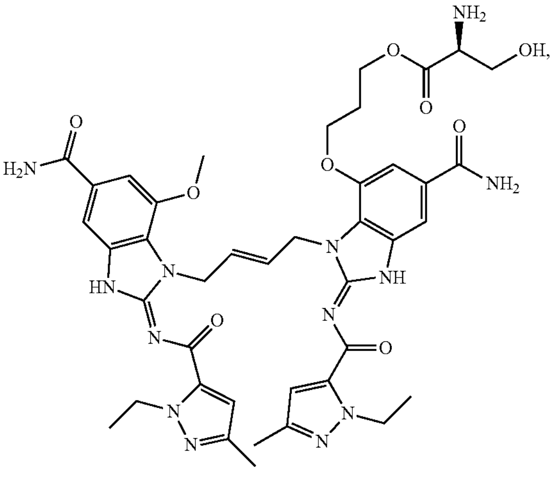
-continued
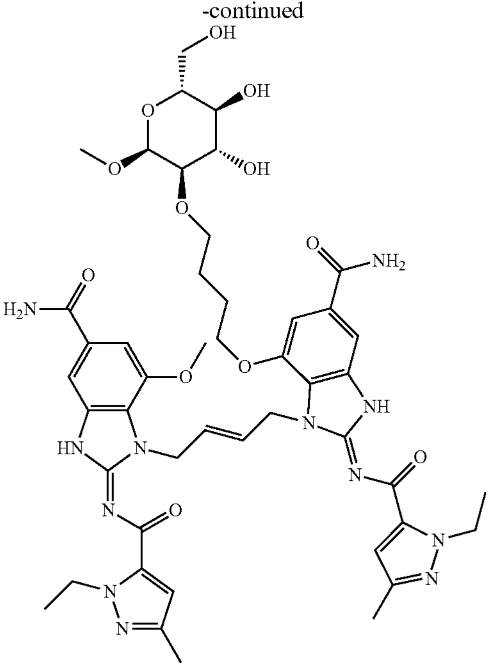
,
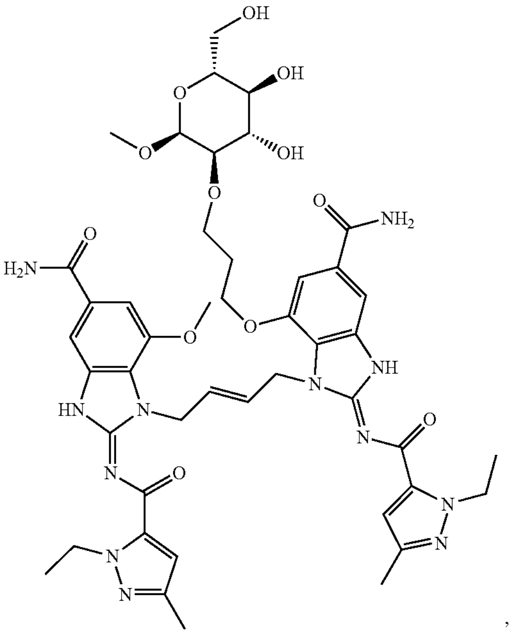
,
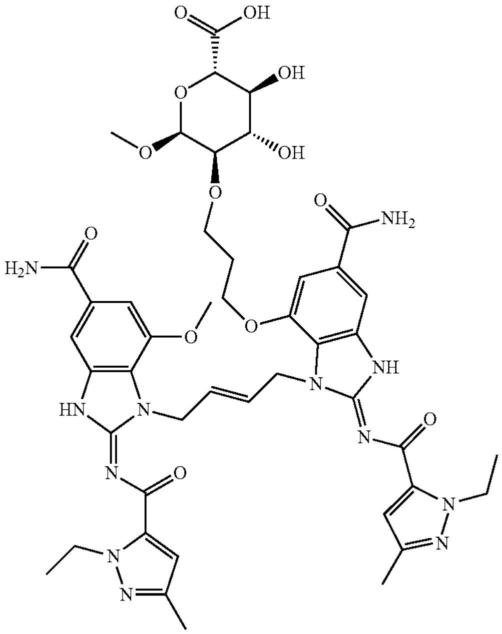
,

-continued
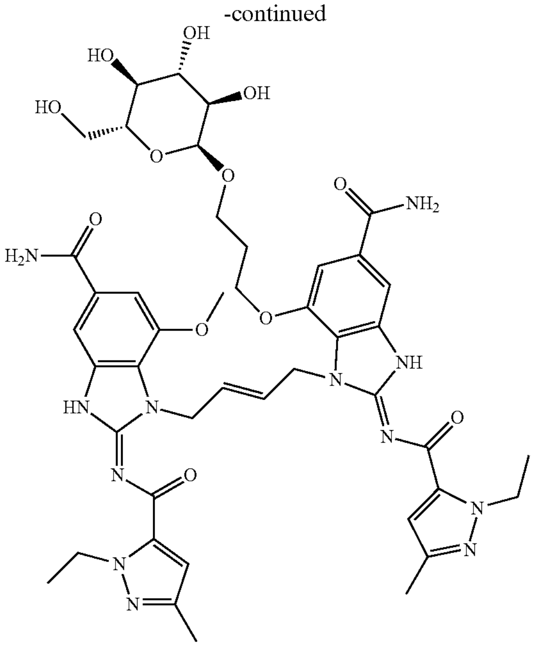
,
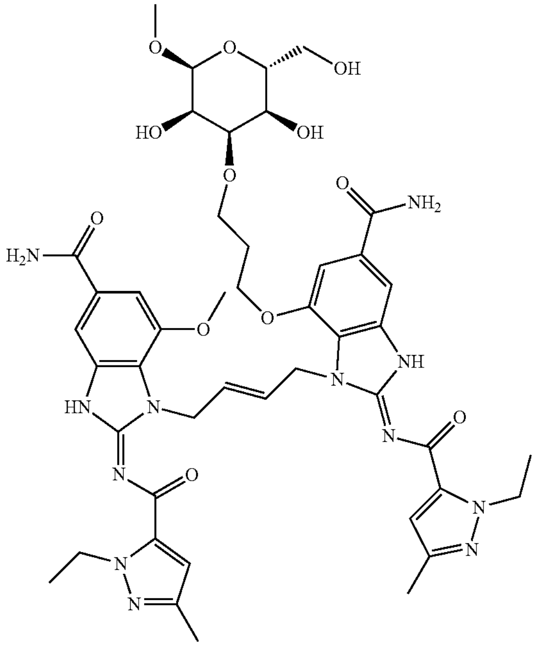
,
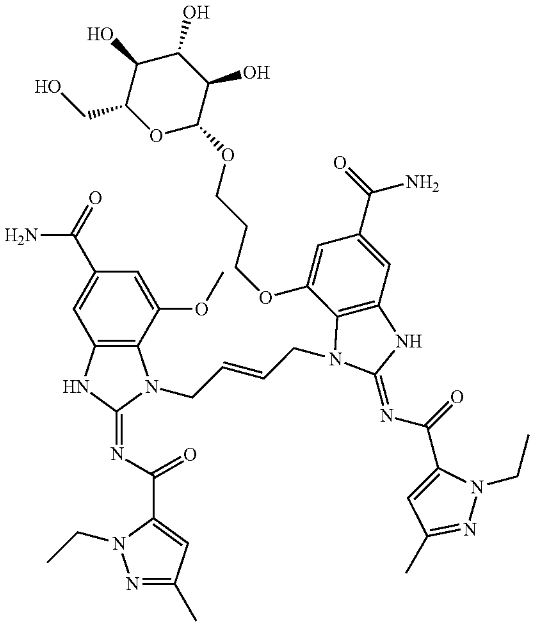
,
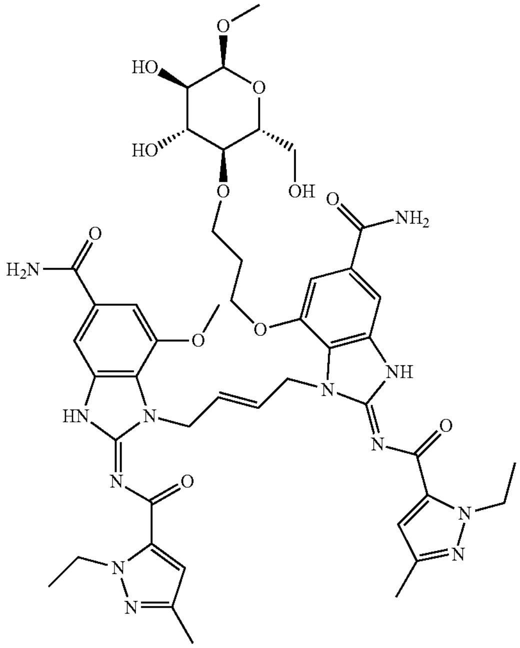
,

-continued
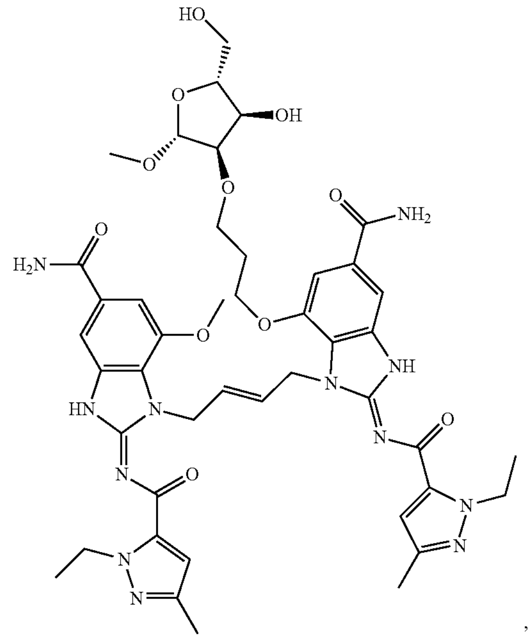
,
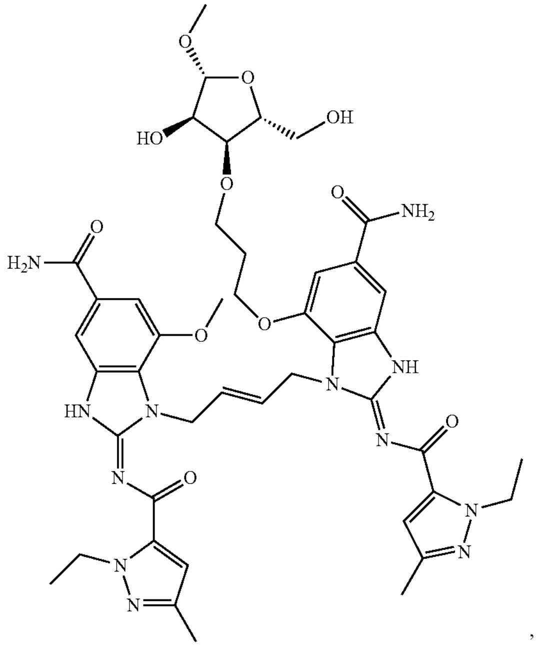
,
-continued
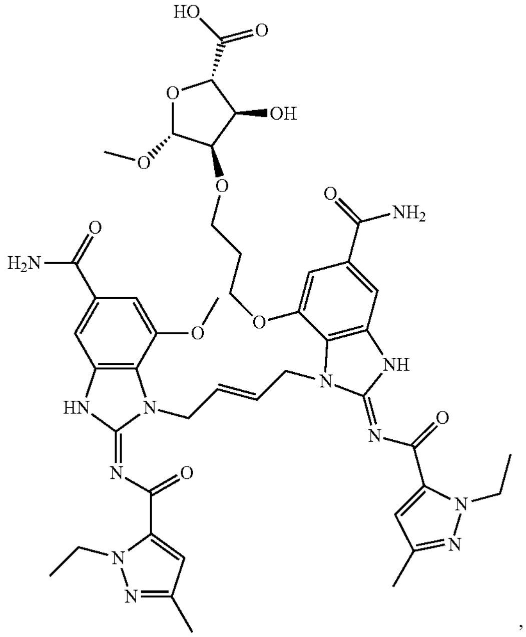
,
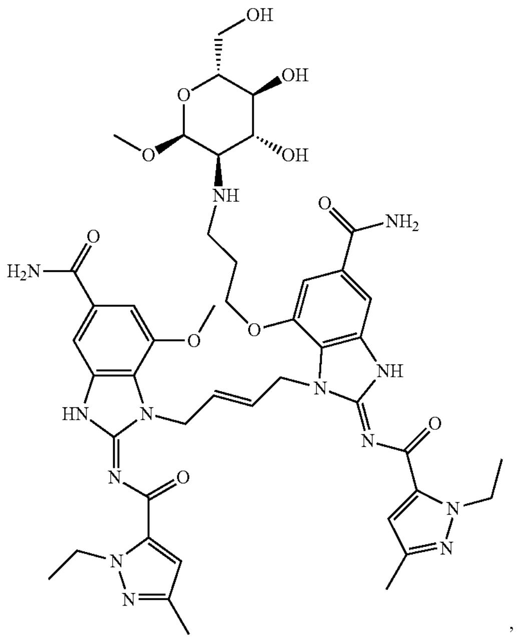
,

-continued
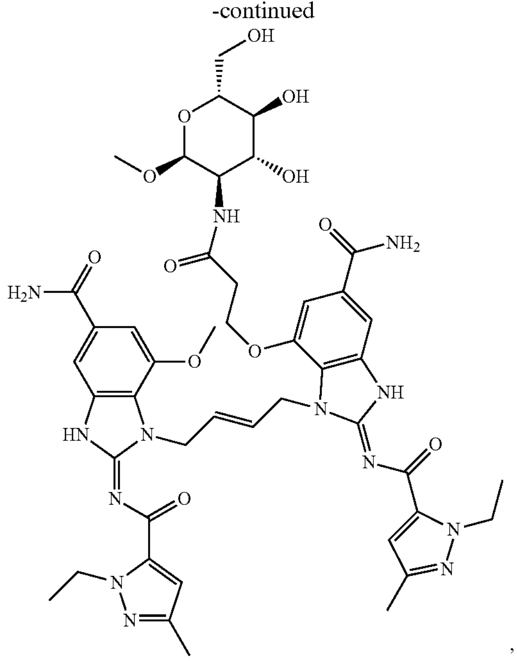
,
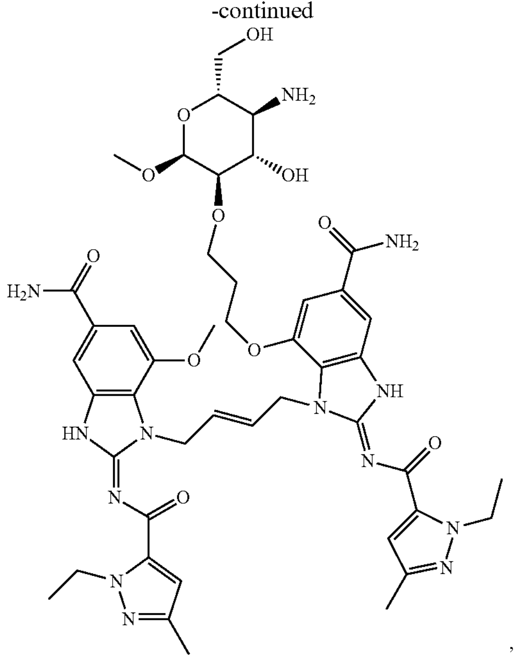
,
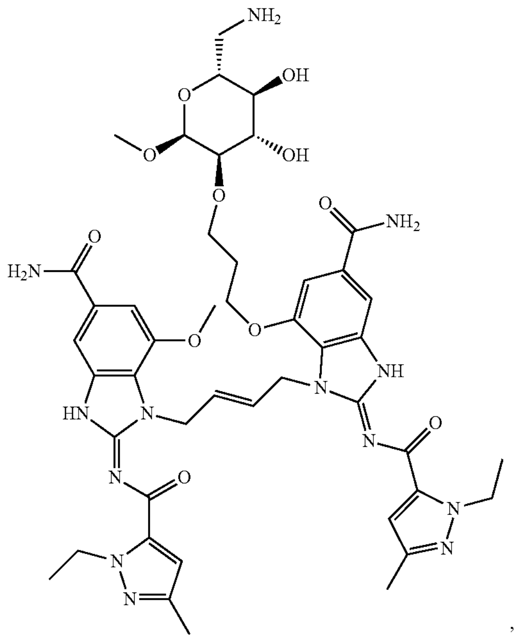
,
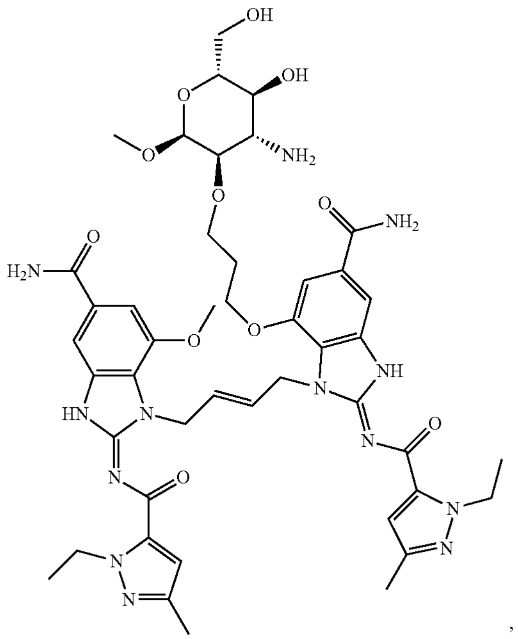
,

-continued
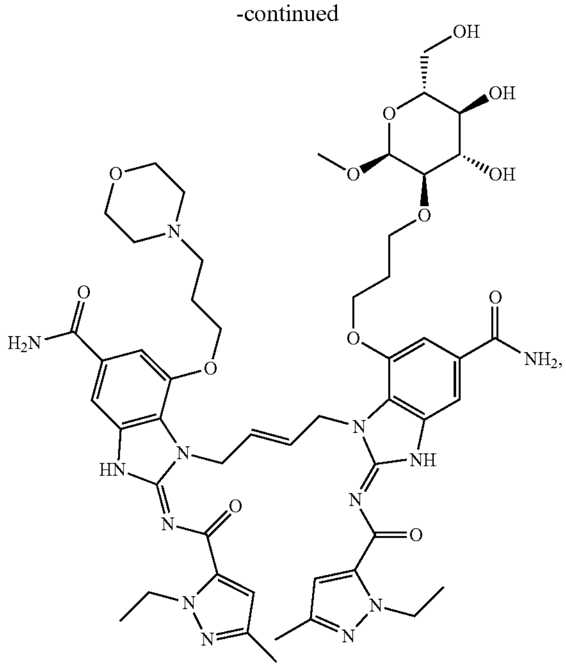
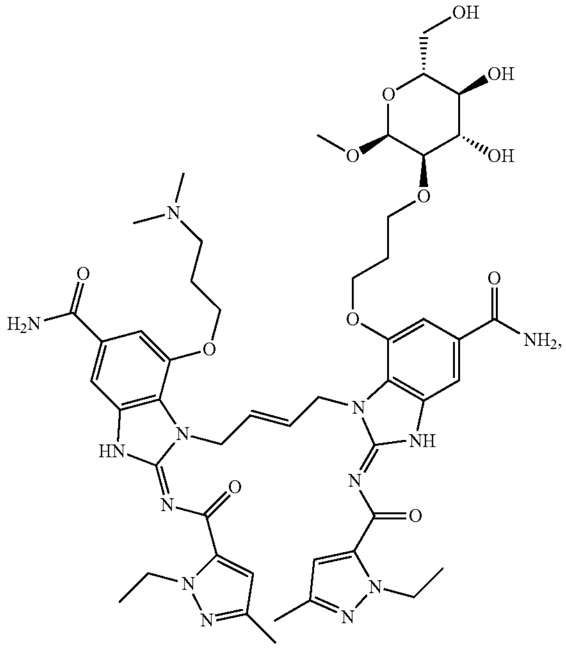
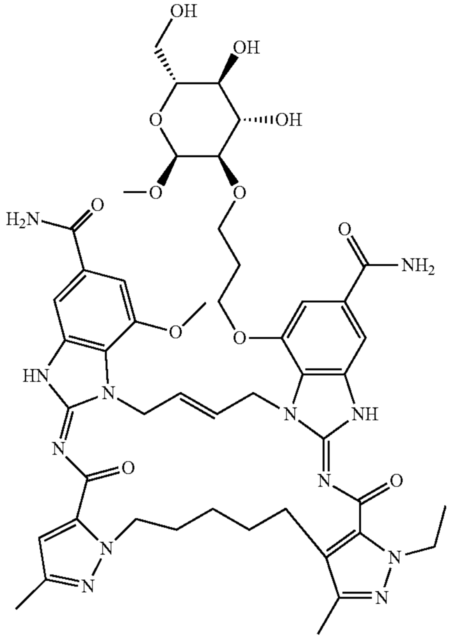
,
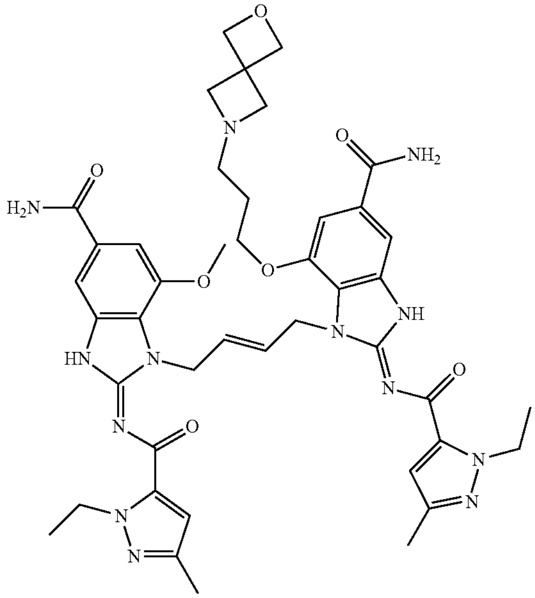
,

-continued
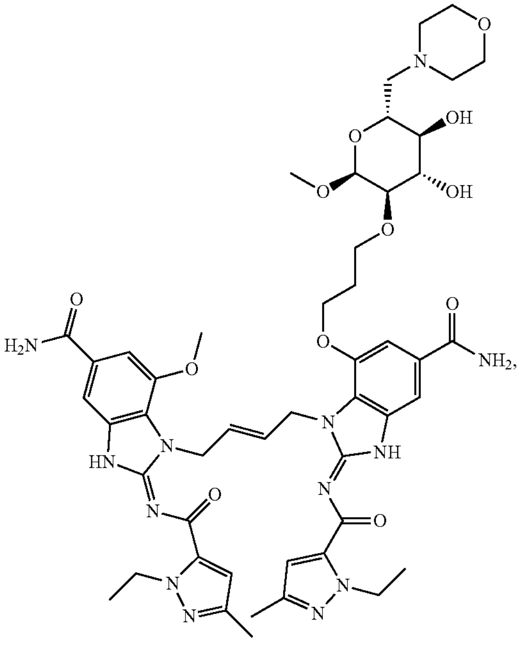
-continued
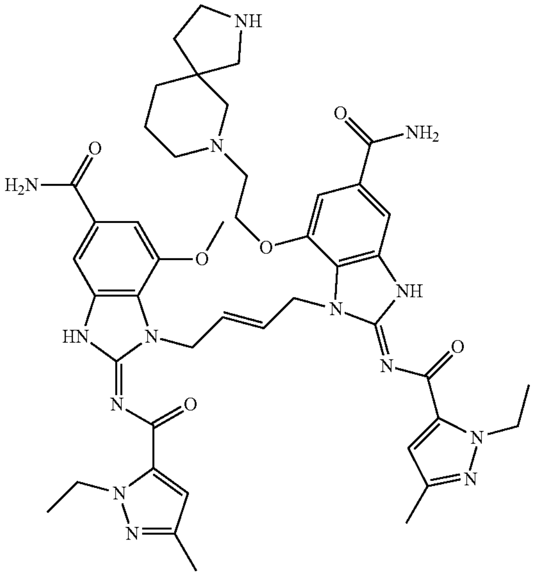
,
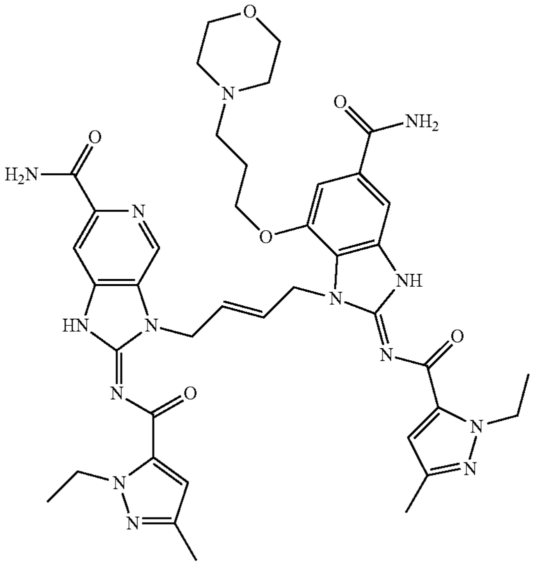
,
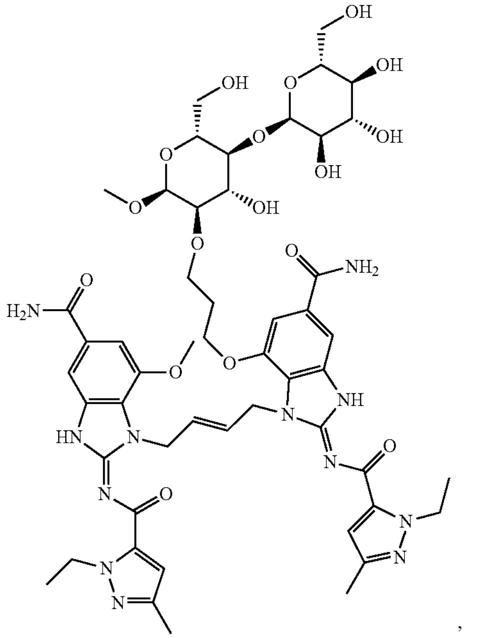
,

-continued
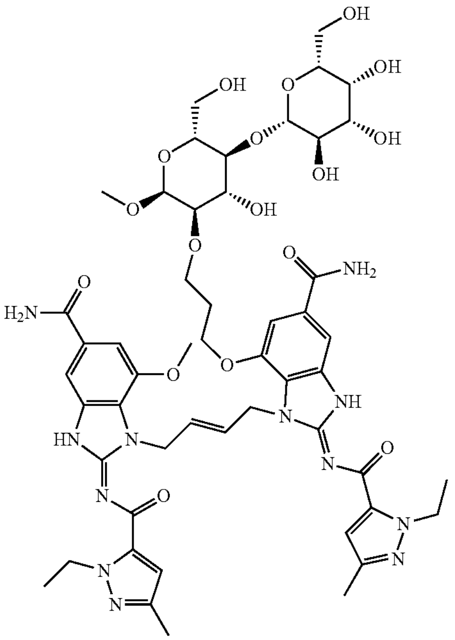
,
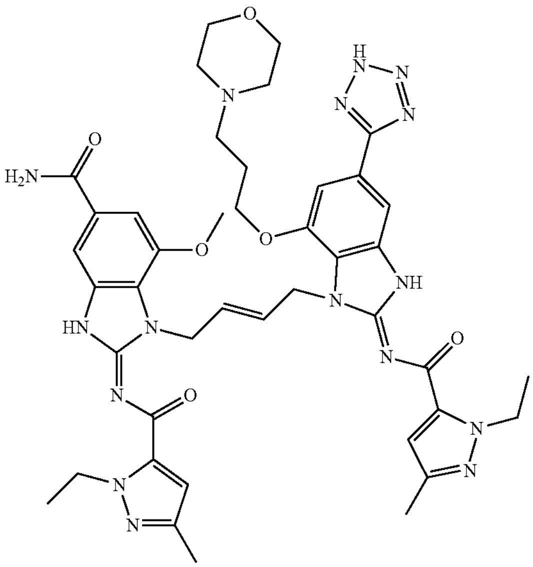
,
-continued
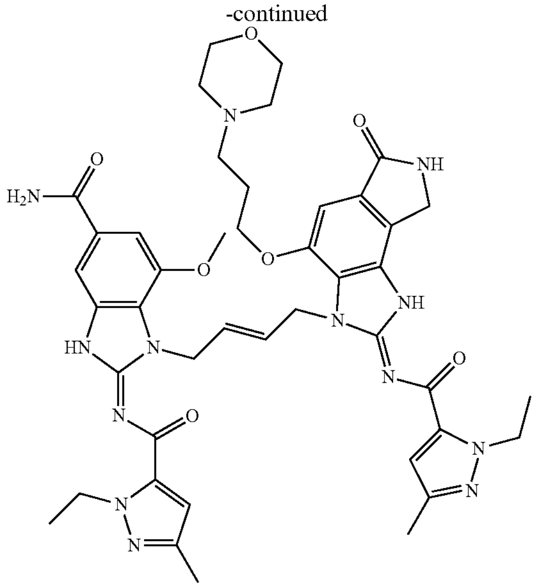
,
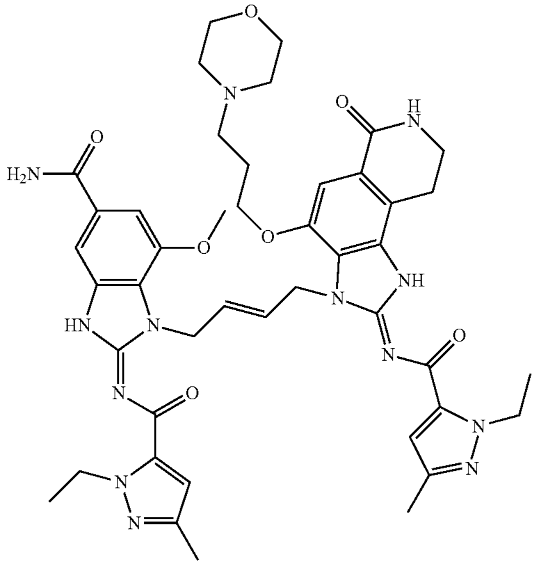
,
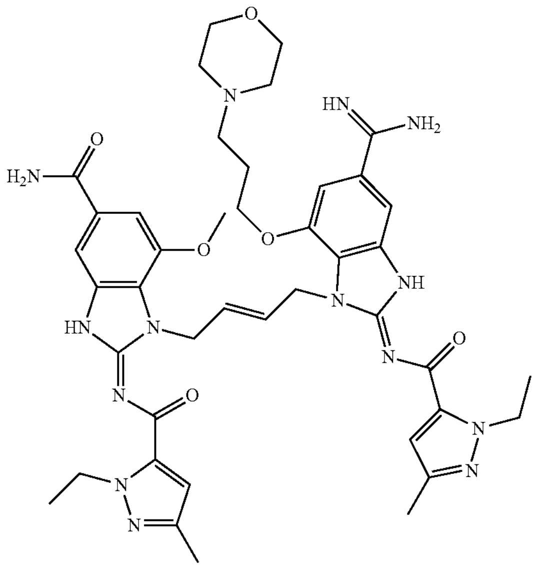
, -continued

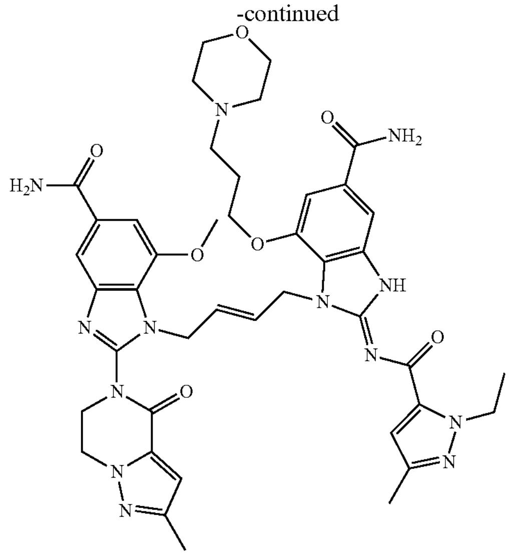

and

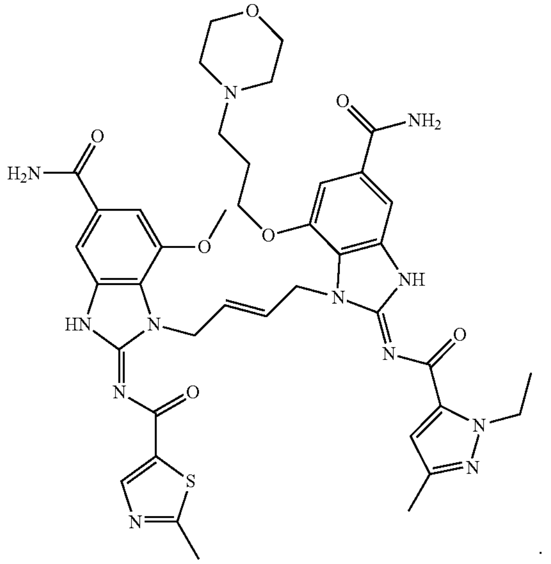

.

In yet another aspect of the present disclosure, also provided is a pharmaceutical composition. In some embodiments of the present disclosure, the pharmaceutical composition comprises the compound or the pharmaceutically acceptable salt thereof described above.

In some embodiments of the present disclosure, the pharmaceutical composition further comprises one or more pharmaceutically acceptable carriers, diluents or excipients.

In yet another aspect of the present disclosure, also provided is use of the compound or the pharmaceutically acceptable salt thereof described above or the pharmaceutical composition described above in the preparation of a medicament for the prevention or treatment of a STING-mediated disease.

In some embodiments of the present disclosure, the STING-mediated disease comprises a disease selected from the group consisting of cancer, inflammation, infectious diseases and immune-related diseases.

In some embodiments of the present disclosure, the cancer is selected from the group consisting of adrenocortical carcinoma, anal carcinoma, anorectal carcinoma, anal canal carcinoma, appendiceal carcinoma, cerebellar astrocytoma, cerebral astrocytoma, basal cell carcinoma, skin carcinoma (non-melanoma), biliary tract carcinoma, extrahepatic bile duct carcinoma, intrahepatic bile duct carcinoma, bladder carcinoma, osteoarticular carcinoma, osteosarcoma, malignant fibrous histiocytoma, brain carcinoma, brain tumors, brain stem glioma, ependymoma, medulloblastoma, visual pathway and hypothalamic gliomas, breast carcinoma, bronchial adenoma, nervous system carcinoma, nervous system lymphoma, central nervous system carcinoma, central nervous system lymphoma, cervical carcinoma, chronic lymphocytic leukemia, chronic myelogenous leukemia, chronic myeloproliferative disease, colon carcinoma, colorectal carcinoma, cutaneous T-cell lymphoma, lymphoid tumors, granuloma fungoides, Sezary syndrome, endometrial carcinoma, esophageal carcinoma, extracranial germ cell tumors, extragonadal germ cell tumors, eye carcinoma, intraocular melanoma, retinoblastoma, gallbladder carcinoma, gastric carcinoma, gastrointestinal carcinoids, gastrointestinal stromal tumors (GIST), germ cell tumors, ovarian germ cell tumors, head and neck carcinoma, hepatocellular carcinoma, Hodgkin lymphoma, islet cell tumors, Kaposi's sarcoma, kidney carcinoma, laryngeal carcinoma, acute lymphocytic leukemia, acute myelogenous leukemia, hairy cell leukemia, lip and oral cavity carcinoma, liver carcinoma, lung carcinoma, non-small-cell lung carcinoma, small cell lung carcinoma, non-Hodgkin's lymphoma, primary central nervous system lymphoma, Waldenstrom macroglobulinemia, melanoma, mesothelioma, metastatic squamous carcinoma, tongue carcinoma, multiple endocrine tumor syndrome, myelodysplastic syndrome, multiple myeloma, nasopharyngeal carcinoma, neuroblastoma, oropharyngeal carcinoma, ovarian carcinoma, ovarian epithelial carcinoma, ovarian low malignant potential tumors, pancreatic carcinoma, pancreatic islet cell pancreatic carcinoma, sinus and nasal cavity carcinoma, parathyroid carcinoma, sinus carcinoma and nasal cavity carcinoma, parathyroid carcinoma, penile carcinoma, pharyngeal carcinoma, pheochromocytoma, pinealoma, pituitary tumors, plasma cell tumors, pleuropulmonary blastoma, prostate carcinoma, rectal carcinoma, renal pelvis and ureter transitional cell carcinoma, retinoblastoma, rhabdomyosarcoma, salivary gland carcinoma, Ewing's sarcoma, Kaposi's sarcoma, synovial sarcoma, uterine carcinoma, uterine sarcoma, small intestine carcinoma, soft tissue sarcoma, squamous cell carcinoma, supratentorial primitive neuroectodermal tumors, testicular carcinoma, throat carcinoma, thymoma, urinary tract carcinoma, endometriosis, vaginal carcinoma, vulval carcinoma, malignant pleural effusion, and Wilm's tumors.

In some embodiments of the present disclosure, the STING-mediated disease is selected from head and neck carcinoma.

In some embodiments of the present disclosure, the STING-mediated disease is selected from breast carcinoma.

In some embodiments of the present disclosure, the STING-mediated disease is selected from colorectal carcinoma.

In some embodiments of the present disclosure, the STING-mediated disease is selected from melanoma.

In some embodiments of the present disclosure, the STING-mediated disease is selected from lymphoma.

In some embodiments of the present disclosure, the STING-mediated disease is selected from bladder carcinoma.

In some embodiments of the present disclosure, the STING-mediated disease is selected from cutaneous squamous cell carcinoma.

In some embodiments of the present disclosure, the STING-mediated disease is selected from ovarian carcinoma.

In some embodiments of the present disclosure, the STING-mediated disease is selected from gastric carcinoma.

In some embodiments of the present disclosure, the STING-mediated disease is selected from esophageal carcinoma.

In some embodiments of the present disclosure, the STING-mediated disease is selected from prostate carcinoma.

In yet another aspect of the present disclosure, also provided is use of the compound or the pharmaceutically acceptable salt thereof described above or the pharmaceutical composition described above in the preparation of a medicament for the prevention or treatment of a STING-mediated tumor complication.

In some embodiments of the present disclosure, the STING-mediated tumor complication is selected from malignant pleural effusion.

In some embodiments of the present disclosure, the STING-mediated tumor complication is selected from ascites.

In yet another aspect of the present disclosure, also provided is a method for treating a STING-mediated disease. In some embodiments of the present disclosure, the method comprises administering to a patient suffering from a STING-mediated disease a therapeutically effective amount of the compound or the pharmaceutically acceptable salt thereof described above or a therapeutically effective amount of the pharmaceutical composition described above.

DEFINITIONS AND DESCRIPTION

Unless otherwise stated, the following terms and phrases used herein are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound disclosed herein contains a relatively acidic functional group, a base addition salt can be obtained by contacting the neutral form of such a compound with a sufficient amount of a base in a pure solution or a suitable inert solvent. Pharmaceutically acceptable base addition salts include sodium, potassium, calcium, ammonium, organic amine, or magnesium salts, or similar salts. When the compound disclosed herein contains a relatively basic functional group, an acid addition salt can be obtained by contacting the neutral form of such a compound with a sufficient amount of an acid in a pure solution or a suitable inert solvent. Examples of pharmaceutically acceptable acid addition salts include salts derived from inorganic acids, such as hydrochloric acid, hydrobromic acid, nitric acid, carbonic acid, bicarbonate radical, phosphoric acid, monohydrogen phosphate, dihydrogen phosphate, sulfuric acid, hydrogen sulfate, hydroiodic acid and phosphorous acid; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid; also included are salts of amino acids (e.g., arginine) and salts of organic acids such as glucuronic acid. Certain specific compounds disclosed herein contain both basic and acidic functional groups that allow the compounds to be converted into either base or acid addition salts.

The pharmaceutically acceptable salts disclosed herein can be synthesized from a parent compound having an acidic or basic group by conventional chemical methods. In general, such salts are prepared by the following method: performing a reaction of the free acid or base form of the compound and a stoichiometric amount of an appropriate base or acid in water or an organic solvent or a mixture thereof.

The compound disclosed herein may have a specific geometric or stereoisomeric form. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereomer enriched mixture, all of which are encompassed within the scope of the present disclosure. Substituents such as alkyl may have an additional asymmetric carbon atom. All these isomers and mixtures thereof are encompassed within the scope of the present disclosure.

Unless otherwise stated, the absolute configuration of a stereogenic center is represented by a wedged solid bond ( ) and a wedged dashed bond ( ) and the relative configuration of a stereogenic center is represented by a straight solid bond ( ) and a straight dashed bond ( ) A wavy line ( ) represents a wedged solid bond ( ) or a wedged dashed bond ( ), or a wavy line ( ) represents a straight solid bond ( ) and a straight dashed bond ( ).

The compounds disclosed herein may be present in a particular form. Unless otherwise stated, the term "tautomer" or "tautomeric form" means that different functional isomers are in dynamic equilibrium at room temperature and can be rapidly converted into each other. If tautomers are possible (e.g., in solution), the chemical equilibrium of the tautomers can be achieved. For example, a proton tautomer, also known as a prototropic tautomer, includes interconversion by proton migration, such as keto-enol isomerism and imine-enamine isomerism. A valence isomer includes interconversion by recombination of some bonding electrons. A specific example of the keto-enol tautomerism is the interconversion between the tautomers pentane-2,4-dione and 4-hydroxypent-3-en-2-one.

Unless otherwise stated, the term "enriched with one isomer", "isomer enriched", "enriched with one enantiomer" or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8% or 99.9%.

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. If one enantiomer of a certain compound disclosed herein is to be obtained, the desired pure enantiomer can be prepared by asymmetric synthesis or derivatization using a chiral auxiliary, wherein the resulting diastereoisomeric mixture is separated and the auxiliary group is cleaved. Or, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods known in the art to obtain the pure enantiomer. Furthermore, the enantiomer and the diastereoisomer are generally isolated through chromatography using a chiral stationary phase, optionally in combination with chemical derivatization (e.g., carbamate generated from amines). The compound disclosed herein may contain an unnatural proportion of atomic isotope at one or more of the atoms that constitute the compound. For example, the compound may be labeled with a radioisotope, such as tritium ($^{3}H$), iodine-125 ($^{125}I$), or C-14 ($^{14}C$). For another example, hydrogen can be substituted with deuterium to form a deuterated drug, and the bond formed by deuterium and carbon is firmer than that formed by common hydrogen and carbon. Compared with an undeuterated drug, the deuterated drug has the advantages of reduced toxic side effect, increased stability, enhanced efficacy, prolonged biological half-life and the like. All isotopic variations of the compounds disclosed herein, whether radioactive or not, are encompassed within the scope of the present disclosure. "Optional" or "optionally" means that the subsequently described event or circumstance may, but does not necessarily, occur, and the description includes instances where the event or the circumstance occurs and the instances where it does not.

The term "substituted" means that one or more hydrogen atoms on a specific atom are substituted by substituents which may include deuterium and hydrogen variants, as long as the valence of the specific atom is normal and the substituted compound is stable. When the substituent is oxygen (i.e., =O), it means that two hydrogen atoms are substituted. Substitution with oxygen does not occur on aromatic groups. The term "optionally substituted" means that an atom can be substituted with a substituent or not. Unless otherwise specified, the type and number of the substituent may be arbitrary as long as being chemically achievable.

When any variable (e.g., R) occurs more than once in the constitution or structure of a compound, the variable is independently defined in each case. Thus, for example, if a group is substituted with 0-2 R, the group can be optionally substituted with up to two R, and the definition of R in each case is independent. Furthermore, a combination of a substituent and/or a variant thereof is permissible only if the combination can result in a stable compound.

When the number of a linking group is 0, for example, —(CRR)O—, it means that the linking group is a single bond.

When one of variants is selected from a single bond, it means that two groups linking by this variant are linked directly. For example, in A-L-Z, when L represents a single bond, it means that the structure is actually A-Z.

When the enumerative linking group does not indicate the direction for linking, the direction for linking is arbitrary. For example, when the linking group L contained in

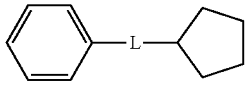

is -M-W—, -M-W— can either link phenyl ring and cyclopentane in a direction same as left-to-right reading order to form

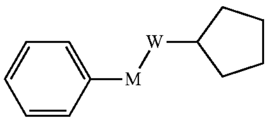

, or link phenyl ring and cyclopentane in an opposing direction to form

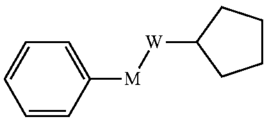

.

A combination of the linking group, a substituent and/or a variant thereof is permissible only if the combination can result in a stable compound.

Unless otherwise specified, the number of atoms on a ring is generally defined as the member number of the ring. For example, "5-6 membered ring" refers to a "ring" on which 5 to 6 atoms are arranged in a circle.

Unless otherwise specified, "5-6 membered heterocyclic ring" refers to a saturated or unsaturated cyclic group consisting of 5 to 6 ring atoms, of which 1, 2, 3 or 4 ring atoms are heteroatoms independently selected from the group consisting of O, S and N, with the remaining being carbon atoms. The nitrogen atom is optionally quaternized, and the nitrogen and sulfur heteroatoms can be optionally oxidized (i.e., NO and $S(O)_p$, wherein p is 1 or 2). This includes monocyclic and bicyclic systems, wherein the bicyclic system includes spirocyclic, fused, and bridged rings. Furthermore, with respect to the "5-6 membered heterocyclic ring", a heteroatom may occupy the position where the heterocycloalkyl is linked to the rest of the molecule. The 5-6 membered heterocyclic ring includes 5-membered heterocyclic ring and 6-membered heterocyclic ring. Examples of 5-6 membered heterocyclic ring include, but are not limited to,

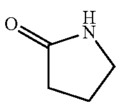

,

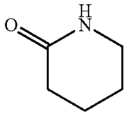

and the like.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc., and may be monovalent (e.g., methyl), divalent (e.g., methylene), or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, and the like.

Unless otherwise specified, the term "$C_{1-3}$ alkyl" refers to a linear or branched saturated hydrocarbon group consisting of 1 to 3 carbon atoms. The $C_{1-3}$ alkyl includes, but is not limited to, $C_{1-2}$ and $C_{2-3}$ alkyl, etc., and may be monovalent (e.g., methyl), divalent (e.g., methylene) or polyvalent (e.g., methenyl). Examples of $C_{1-3}$ alkyl include, but are not limited to, methyl (Me), ethyl (Et), propyl (including n-propyl and isopropyl), and the like.

Unless otherwise specified, the term "$C_{1-6}$ alkoxy" refers to those alkyl groups that each contains 1 to 6 carbon atoms and is linked to the rest part of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy and the like. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, and the like.

Unless otherwise specified, the term "$C_{1-3}$ alkoxy" refers to those alkyl groups that each contains 1 to 3 carbon atoms and is linked to the rest part of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, the term "$C_{1-6}$ alkylamino" refers to those alkyl groups that each contains 1 to 6 carbon atoms and is linked to the rest part of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino and the like. Examples of $C_{1-6}$ alkylamino include, but are not limited to, $-NHCH_3$, $-N(CH_3)_2$, $-NHCH_2CH_3$, $-N(CH_3)CH_2CH_3$, $-N(CH_2CH_3)(CH_2CH_3)$, $-NHCH_2CH_2CH_3$, $-NHCH_2(CH_3)_2$, $-NHCH_2CH_2CH_2CH_3$, and the like.

Unless otherwise specified, the term "$C_{1-3}$ alkylamino" refers to those alkyl groups that each contains 1 to 3 carbon atoms and is linked to the rest part of the molecule through an amino group. The $C_{1-3}$ alkylamino includes $C_{1-2}$, $C_3$ and $C_2$ alkylamino and the like. Examples of $C_{1-3}$ alkylamino include, but are not limited to, $-NHCH_3$, $-N(CH_3)_2$, $-NHCH_2CH_3$, $-N(CH_3)CH_2CH_3$, $-NHCH_2CH_2CH_3$, $-NHCH_2(CH_3)_2$, and the like.

Unless otherwise specified, the term "$C_{1-6}$ alkylthio" refers to those alkyl groups that each contains 1 to 6 carbon atoms and is linked to the rest part of the molecule through an sulfur atom. The $C_{1-6}$ alkylthio includes $C_{1-4}$, $C_{1-3}$, $C_{1-2}$, $C_{2-6}$, $C_{2-4}$, $C_6$, $C_5$, $C_4$, $C_3$ and $C_2$ alkylthio and the like. Examples of $C_{1-6}$ alkylthio include, but are not limited to, $-SCH_3$, $-SCH_2CH_3$, $-SCH_2CH_2CH_3$, $-SCH_2(CH_3)_2$, and the like.

Unless otherwise specified, the term "$C_{1-3}$ alkylthio" refers to those alkyl groups that each contains 1 to 3 carbon atoms and is linked to the rest part of the molecule through an sulfur atom. The $C_{1-3}$ alkylthio includes $C_{1-3}$, $C_{1-2}$ and $C_3$ alkylthio and the like. Examples of $C_{1-3}$ alkylthio include, but are not limited to, $-SCH_3$, $-SCH_2CH_3$, $-SCH_2CH_2CH_3$, $-SCH_2(CH_3)_2$, and the like.

Unless otherwise specified, the term "$C_{1-6}$ alkylamino" refers to those alkyl groups that each contains 1 to 6 carbon atoms and is linked to the rest part of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino and the like. Examples of $C_{1-6}$ alkylamino include, but are not limited to, $-NHCH_3$, $-N(CH_3)_2$, $-NHCH_2CH_3$, $-N(CH_3)CH_2CH_3$, $-N(CH_2CH_3)(CH_2CH_3)$, $-NHCH_2CH_2CH_3$, $-NHCH_2(CH_3)_2$, $-NHCH_2CH_2CH_2CH_3$, and the like.

Unless otherwise specified, the term "$C_{1-4}$ alkylamino" refers to those alkyl groups that each contains 1 to 4 carbon atoms and is linked to the rest part of the molecule through an amino group. The $C_{1-4}$ alkylamino includes $C_{1-3}$, $C_{1-2}$, $C_{2-4}$, $C_4$, $C_3$ and $C_2$ alkylamino and the like. Examples of $C_{1-4}$ alkylamino include, but are not limited to, $-NHCH_3$, $-N(CH_3)_2$, $-NHCH_2CH_3$, $-N(CH_3)CH_2CH_3$, $-N(CH_2CH_3)(CH_2CH_3)$, $-NHCH_2CH_2CH_3$, $-NHCH_2(CH_3)_2$, $-NHCH_2CH_2CH_2CH_3$, and the like.

Unless otherwise specified, the term "$C_{1-3}$ alkylamino" refers to those alkyl groups that each contains 1 to 3 carbon atoms and is linked to the rest part of the molecule through an amino group. The $C_{1-3}$ alkylamino includes $C_{1-2}$, $C_3$ and $C_2$ alkylamino and the like. Examples of $C_{1-3}$ alkylamino include, but are not limited to, $-NHCH_3$, $-N(CH_3)_2$, $-NHCH_2CH_3$, $-N(CH_3)CH_2CH_3$, $-NHCH_2CH_2CH_3$, $-NHCH_2(CH_3)_2$, and the like.

Unless otherwise specified, the term "5-6 membered heterocycloalkyl", by itself or in combination with other terms, refers to a saturated cyclic group consisting of 5 to 6 ring atoms, of which 1, 2, 3, or 4 ring atoms are heteroatoms independently selected from the group consisting of O, S and N, with the remaining being carbon atoms. The nitrogen atom is optionally quaternized, and the nitrogen and sulfur heteroatoms can be optionally oxidized (i.e., NO and $S(O)_p$, wherein p is 1 or 2). This includes monocyclic and bicyclic systems, wherein the bicyclic system includes spirocyclic, fused, and bridged rings. Furthermore, with respect to the "5-6 membered heterocycloalkyl", a heteroatom may occupy the position where the heterocycloalkyl is linked to the rest of the molecule. The 5-6 membered heterocycloalkyl includes 5-membered heterocycloalkyl and 6-membered heterocycloalkyl. Examples of 5-6 membered heterocycloalkyl include, but are not limited to, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, or the like.

Unless otherwise specified, the terms "$C_{6-10}$ aromatic ring" and "$C_{6-10}$ aryl" herein are used interchangeably. The term "$C_{6-10}$ aromatic ring" or "$C_{6-10}$ aryl" refers to a cyclic hydrocarbon group consisting of 6 to 10 carbon atoms and having a conjugated π-electron system. The group may be a monocyclic, fused bicyclic or fused tricyclic system, wherein the rings are aromatic. It may be monovalent, divalent or polyvalent, and the $C_{6-10}$ aryl includes $C_{6-9}$, $C_9$, $C_{10}$ and $C_6$ aryl, etc. Examples of $C_{6-10}$ aryl include, but are not limited to, phenyl, naphthyl (including 1-naphthyl, 2-naphthyl, etc.).

Unless otherwise specified, the terms "5-10 membered heteroaromatic ring" and "5-10 membered heteroaryl" are used interchangeably herein. The term "5-10 membered heteroaryl" refers to a cyclic group consisting of 5 to 10 ring atoms and having a conjugated pi-electron system, in which 1, 2, 3, or 4 ring atoms are heteroatoms independently selected from the group consisting of O, S and N, with the remaining being carbon atoms. It can be a monocyclic, fused bicyclic or fused tricyclic system, wherein the rings are aromatic. The nitrogen atom is optionally quaternized, and the nitrogen and sulfur heteroatoms are optionally oxidized (i.e., NO and $S(O)_p$, wherein p is 1 or 2). The 5-10 membered heteroaryl can be linked to the rest of the molecule through a heteroatom or a carbon atom. The 5-10 membered heteroaryl includes 5-8 membered heteroaryl, 5-7 membered heteroaryl, 5-6 membered heteroaryl, 5 membered heteroaryl and 6 membered heteroaryl, etc. Examples of the 5-10 membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (including 1H-1,2,3-triazolyl, 2H-1,2,3-triazolyl, 1H-1,2,4-triazolyl, 4H-1,2,4-triazolyl, etc.), tetrazolyl, isoxazolyl (including 3-isoxazolyl, 4-isoxazolyl, 5-isoxazolyl, etc.), thiazolyl (including 2-thiazolyl, 4-thiazolyl, 5-thiazolyl, etc.), furanyl (including 2-furanyl, 3-furanyl, etc.), thienyl (including 2-thienyl, 3-thienyl, etc.), pyridinyl (including 2-pyridinyl, 3-pyridinyl, 4-pyridinyl, etc.), pyrazinyl, pyrimidinyl (including 2-pyrimidinyl, 4-pyrimidinyl, etc.), benzothiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl, 5-isoquinolinyl, etc.), quinoxalinyl (including 2-quinoxalinyl, 5-quinoxalinyl, etc.) or quinolyl (including 3-quinolyl, 6-quinolyl, etc.).

Unless otherwise specified, $C_{n-n+m}$ or $C_n$—$C_{n+m}$ includes any one of the specific cases of n to n+m carbons, e.g., $C_{1-6}$ includes $C_1$, $C_2$, $C_3$, $C_4$, $C_5$ and $C_6$, and also includes any one of the ranges within n to n+m, e.g., $C_{1-6}$ includes $C_{1-3}$, $C_{1-6}$, $C_{1-4}$, $C_{3-6}$, $C_{3-5}$, $C_{2-5}$ and $C_{1-5}$, etc.; similarly, n membered to n+m membered means n to n+m atoms in a ring, for example, 5-6 membered rings include 5 membered ring and 6 membered ring.

The term "treatment" or "treating" as used herein refers to the administration of one or more pharmaceutical substances, in particular a compound of formula (I) and/or a pharmaceutically acceptable salt thereof as described herein, to an individual suffering from a disease or having symptoms of the disease so as to cure, relieve, alleviate, alter, remedy, ameliorate, improve or affect the disease or the symptoms of the disease. The term "prevention" as used herein refers to the administration of one or more pharmaceutical substances, in particular the compound of formula (IA) or (I) as described herein and/or the pharmaceutically acceptable salt thereof, to an individual having a predisposition to the disease so as to prevent the individual suffering from the disease. The terms "treating", "contacting", and "reacting", when referring to a chemical reaction, refer to the addition or mixing of two or more reagents under appropriate conditions to produce the indicated and/or desired product. It should be appreciated that the reaction that produces the indicated and/or desired product may not necessarily result directly from the combination of the two reagents that are initially added, i.e., there may be one or more intermediates formed in the mixture that ultimately result in the formation of the indicated and/or desired product.

The term "effective amount" as used herein refers to an amount generally sufficient to produce a beneficial effect in an individual. An effective amount of the compound disclosed herein can be determined by conventional methods (e.g., modeling, dose escalation research, or clinical trial) in combination with conventional influence factors (e.g., mode of administration, pharmacokinetics of the compound, severity and course of the disease, medical history of the individual, health condition of the individual, and the extent of responsiveness of the individual to the drug).

The compound disclosed herein can be prepared by a variety of synthetic methods well known to those skilled in the art, including the specific embodiments listed below, embodiments formed by combinations thereof with other chemical synthetic methods, and equivalents thereof known to those skilled in the art. Preferred embodiments include, but are not limited to, the examples disclosed herein.

The present disclosure employs the following abbreviations: aq represents water; $CDCl_3$ represents deuterated chloroform; $CD_3OD$ represents deuterated methanol; DMSO-$d_6$ represents deuterated dimethyl sulfoxide; Bz represents benzoyl; TBS represents tert-butyldimethylsilyl.

BRIEF DESCRIPTION OF THE DRAWINGS

FIG. 1 is a graph showing the evaluation results of the drug effect of compound 1 on a CT26 syngeneic mouse model.

DETAILED DESCRIPTION OF THE EMBODIMENT

The present application is described in detail below by way of examples. However, this is by no means disadvantageously limiting the scope of the present application. Although the present application has been described in detail herein and specific examples have also been disclosed, it will be apparent to those skilled in the art that various changes and modifications can be made to the specific embodiments without departing from the spirit and scope of the present application.

Example 1

Preparation of Compound 1

Step 1: Preparation of Compound 1-2

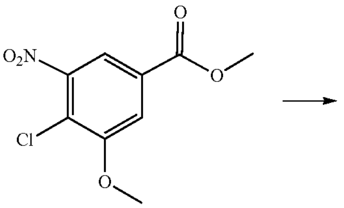

1-1

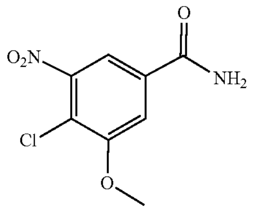

1-2

Compound 1-1 (8 g, 32.57 mmol) was dissolved in a solution of ammonia in methanol (7 M, 70.00 mL) and the system was heated to 50° C. in a sealed tube and stirred for 20 h. The reaction solution was filtered, and the obtained solid was washed with petroleum ether and dried under vacuum to obtain a crude product 1-2 which was used in the next step directly without further purification.

$^1$H NMR (400 MHz, DMSO-$d_6$) δ 8.30 (br s, 1H), 8.05 (d, J=2.0 Hz, 1H), 7.88 (d, J=2.0 Hz, 1H), 7.80 (br s, 1H), 4.02 (s, 3H).

Step 2: Preparation of Compound 1-3

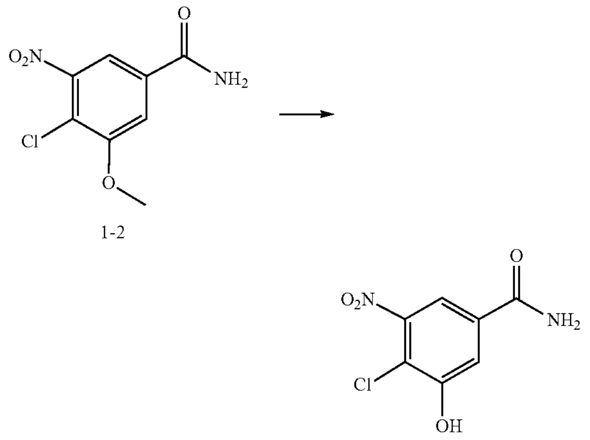

1-2

1-3

Compound 1-2 (7.5 g, 32.52 mmol) was dissolved in dichloromethane (100 mL) at 15° C. under nitrogen atmosphere, and a solution of boron tribromide in dichloromethane (40.74 g, 162.62 mmol, 15.67 mL) (1.0 M in dichloromethane) was added dropwise to the system, and after completion of addition, the reaction system was stirred for 24 h, poured into ice water (1200 mL), stirred for 30 min and filtered, and the solid was dried under vacuum to obtain a crude product 1-3 which was used in the next step directly without further purification.

$^1$H NMR (400 MHz, DMSO-$d_6$) δ 8.19 (br s, 1H), 7.92 (d, J=1.6 Hz, 1H), 7.20 (d, J=1.6 Hz, 1H), 7.68 (s, 1H).

Step 3: Preparation of Compound 1-4

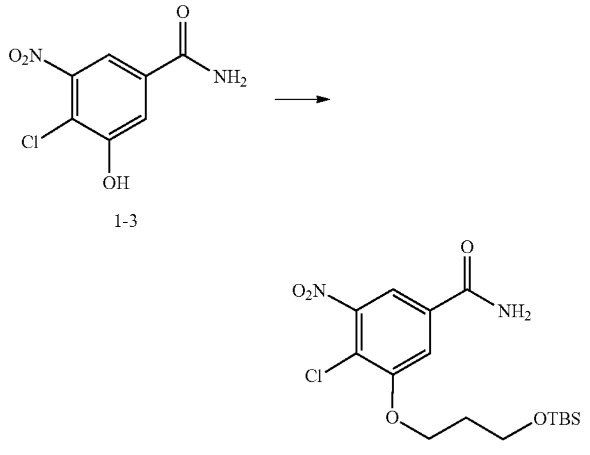

1-3

1-4

Compound 1-3 (1.5 g, 6.93 mmol) and (3-bromopropoxy)-tert-butyldimethylsilane (2.28 g, 9.00 mmol) were dissolved in N,N-dimethylformamide (20 mL), and potassium carbonate (1.91 g, 13.85 mmol) was added. The reaction system was heated to 100° C. and stirred for 2 h, poured into water (150 mL) and filtered to collect the solid, and the solid crude product was purified by silica gel column chromatography (petroleum ether/ethyl acetate (v/v)=1/0-1/1) to obtain compound 1-4.

$^1$H NMR (400 MHz, DMSO-$d_6$) δ 8.31 (br s, 1H), 8.05 (s, 1H), 7.89 (s 1H), 7.80 (br s, 1H), 4.31-4.28 (m, 2H), 3.81-3.78 (m, 2H), 1.99-1.96 (m, 2H), 0.84 (s, 9H), 0.03 (s, 6H).

Step 4: Preparation of Compound 1-5

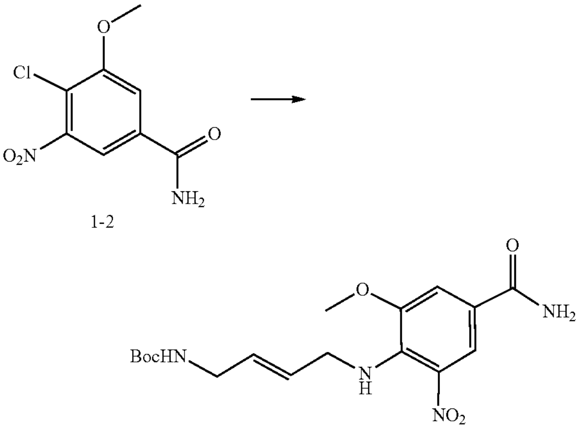

1-2

1-5

Compound 1-2 (2 g, 8.67 mmol) was dissolved in ethanol (15 mL), and tert-butyl trans-(4-amino-2-butenyl)carbamate (1.94 g, 10.41 mmol) and diisopropylethylamine (3.36 g, 26.02 mmol, 4.53 mL) were serially added, the reaction system was heated to 100° C. in a sealed tube and stirred for 24 h and filtered, and the solid was dried under vacuum to obtain a crude product 1-5 which was used in the next step directly without further purification.

MS (ESI) m/z $(M+H)^+$=676.2.

$^1$H NMR (400 MHz, DMSO-$d_6$) δ 8.15 (s, 1H), 7.99 (s, 1H), 7.73-7.70 (m, 1H), 7.51 (s, 1H), 7.30 (s, 1H), 5.49 (s, 2H), 4.05 (s, 2H), 3.98 (s, 3H), 3.44 (s, 2H), 1.31 (s, 9H).

Step 5: Preparation of Compound 1-6

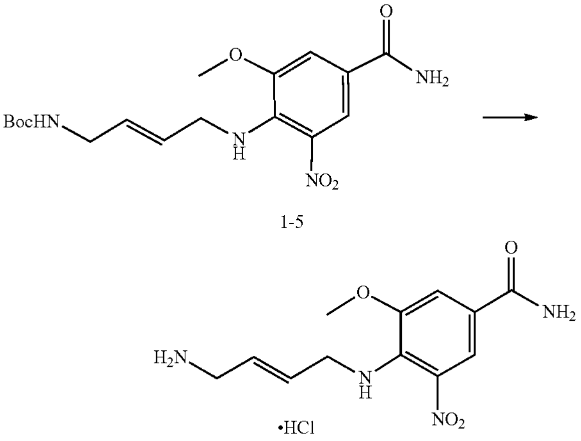

1-5

1-6

Compound 1-5 (2.8 g, 7.36 mmol) was dissolved in 1,4-dioxane (30 mL), a solution of hydrogen chloride in 1,4-dioxane (4.0 M, 20 mL) was added, and the reaction system was stirred at 15° C. for 2 h and concentrated under reduced pressure to obtain a crude product 1-6 which was used in the next step directly without further purification.

Step 6: Preparation of Compound 1-8

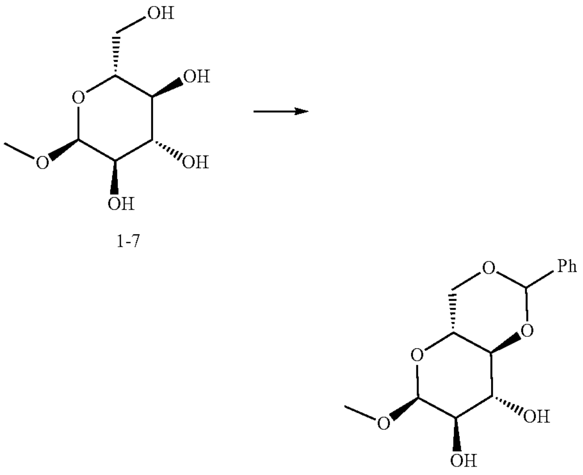

1-7

1-8

Compound 1-7 (5 g, 25.75 mmol) and benzaldehyde dimethylacetal (7.05 g, 46.35 mmol, 6.98 mL) were dissolved in N,N-dimethylformamide (50 mL), p-toluenesulfonic acid (644 mg, 2.58 mmol) was added, the reaction system was stirred at 45° C. for 2 h, added with triethylamine to adjust the pH of the solution to 8 and concentrated under reduced pressure to obtain a crude product, and the solid crude product was purified by silica gel column chromatography (petroleum ether/ethyl acetate (v/v)=1/0-0/1) to obtain compound 1-8.

Step 7: Preparation of Compound 1-9

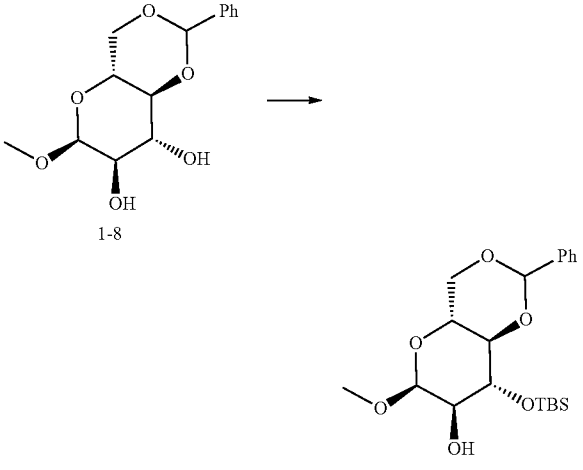

1-8

1-9

Compound 1-8 (5.6 g, 15.87 mmol) was dissolved in N,N-dimethylformamide (60 mL) at 0° C., and imidazole (1.62 g, 23.81 mmol) and tert-butyldimethylchlorosilane (2.87 g, 19.04 mmol) were serially added. The reaction system was heated to 15° C. and stirred for 16 h. The reaction was quenched by adding water (200 mL), and the reaction system was extracted with ethyl acetate (80 mL×3). The organic phases were combined, dried over anhydrous sodium sulfate and filtered, the filtrate was concentrated, and the solid crude product was purified by silica gel column chromatography (petroleum ether/ethyl acetate (v/v)=1/0-4/1) to obtain compound 1-9.

$^1$H NMR (400 MHz, $CDCl_3$) δ 7.58-7.45 (m, 2H), 7.41-7.32 (m, 3H), 5.51 (s, 1H), 4.81 (d, J=4.0 Hz, 1H), 4.28 (dd, J=4.0, 9.6 Hz, 1H), 3.96-3.87 (m, 1H), 3.82-3.72 (m, 2H), 3.60 (dt, J=4.0, 8.4 Hz, 1H), 3.50-3.36 (m, 4H), 2.12 (d, J=8.0 Hz, 1H), 0.88 (s, 9H), 0.11 (s, 3H), 0.03 (s, 3H).

Step 8: Preparation of Compound 1-11

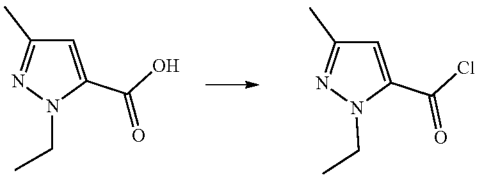

1-10 1-11

Compound 1-10 (1 g, 6.49 mmol) was dissolved in dichloromethane (20 mL), N,N-dimethylformamide (0.1 mL) and oxalyl chloride (906 mg, 7.14 mmol, 624 μL) were serially added, and the reaction system was stirred at 15° C. for 1 h and concentrated under reduced pressure to obtain a crude product 1-11 which was used in the next step directly without further purification.

Step 9: Preparation of Compound 1-12

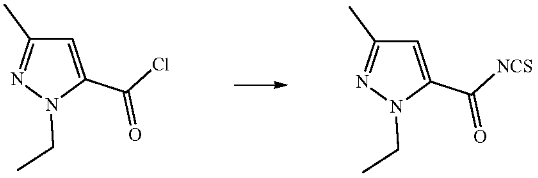

1-11 1-12

Compound 1-11 (1.12 g, 6.49 mmol) was dissolved in acetone (10 mL) at 0° C., and a solution of potassium thiocyanate (693 mg, 7.14 mmol) in acetone (25 mL) was added and stirred at this temperature for 1 h. The reaction system was added with petroleum ether (30 mL) and concentrated under reduced pressure to ⅓ volume. The process was repeated for 3 times, the solvent was removed by filtration, and the solid was washed with petroleum ether and then purified by silica gel column chromatography (petroleum ether/ethyl acetate (v/v)=1/0-9/1) to obtain compound 1-12.

$^1$H NMR (400 MHz, DMSO-$d_6$) δ 6.71 (s, 1H), 4.50-4.45 (m, 2H), 2.27 (s, 3H), 1.40-1.36 (m, 3H).

Step 10: Preparation of Compound 1-13

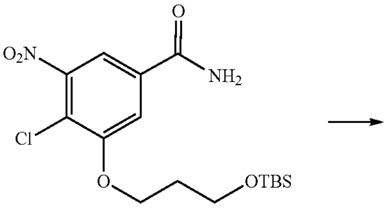

1-4

-continued

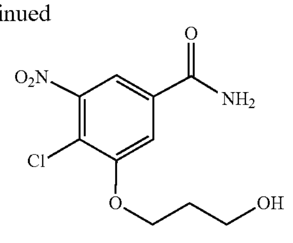

1-13

Compound 1-4 (300 mg, 771.37 μmol) was dissolved in tetrahydrofuran (4 mL), a solution of tetrabutylammonium fluoride in tetrahydrofuran (1.0 M, 1.54 mL) was added, and the reaction system was stirred at 15° C. for 1 h and diluted with ethyl acetate (100 mL) and washed with saturated saline (50 mL×3). The organic phase was dried over anhydrous sodium sulfate and filtered, the filtrate was concentrated under reduced pressure, and the crude product was purified by silica gel column chromatography (dichloromethane/methanol (v/v)=1/0-9/1) to obtain compound 1-13.

$^1H$ NMR (400 MHz, DMSO-$d_6$) δ 8.31 (s, 1H), 8.05 (s, 1H), 7.90 (s, 1H), 7.78 (s, 1H), 4.65-46.2 (m, 1H), 4.32-4.29 (m, 2H), 3.63-3.59 (m, 2H), 1.96-1.93 (m, 2H).

Step 11: Preparation of Compound 1-14

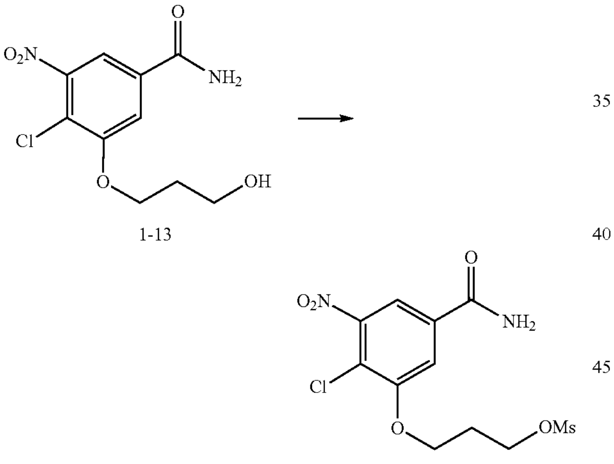

1-13

1-14

Compound 1-13 (0.2 g, 728.18 μmol) was dissolved in tetrahydrofuran (2 mL), triethylamine (221 mg, 2.18 mmol, 304.06 μL) and methanesulfonyl chloride (209 mg, 1.82 mmol, 141 μL) were serially added, and the reaction system was stirred at 15° C. for 0.5 h. The reaction was quenched by adding water (1 mL), and the reaction system was diluted with ethyl acetate (100 mL) and washed with saturated brine (50 mL×3). The organic phase was dried over anhydrous sodium sulfate and filtered, and the filtrate was concentrated under reduced pressure to obtain a crude product 1-14 which was used in the next step directly without further purification.

$^1H$ NMR (400 MHz, DMSO-$d_6$) δ 8.30 (m, 1H), 8.06 (s, 1H), 7.90 (s, 1H), 7.80 (s, 1H), 4.42-4.39 (m, 2H), 4.35-4.32 (m, 2H), 3.19 (s, 1H), 2.24-2.21 (m, 2H).

Step 12: Preparation of Compound 1-15

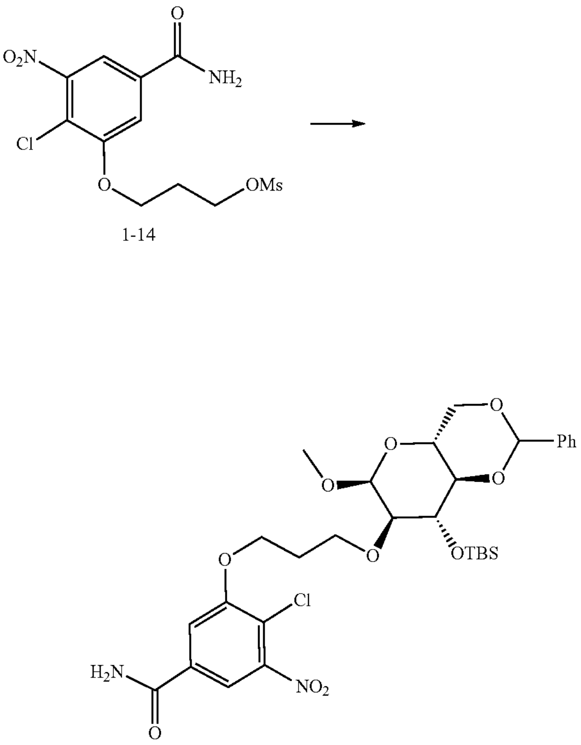

1-14

1-15

Compound 1-14 (1.5 g, 3.78 mmol) was dissolved in N,N-dimethylformamide (40 mL), sodium hydride (756.46 mg, 18.91 mmol, 60% purity) and compound 1-9 (1.40 g, 3.97 mmol) were serially added, and the reaction system was stirred at 15° C. for 2 h. The reaction was quenched by adding methanol (10 mL), and the system was diluted with ethyl acetate (100 mL) and washed with saturated saline (30 mL×3). The organic phase was dried over anhydrous sodium sulfate and filtered, the filtrate was concentrated under reduced pressure, and the crude product was purified by silica gel column chromatography (dichloromethane/methanol (v/v)=1/0-50/3) to obtain compound 1-15.

MS (ESI) m/z $(M+H)^+$=675.1.

Step 13: Preparation of Compound 1-16

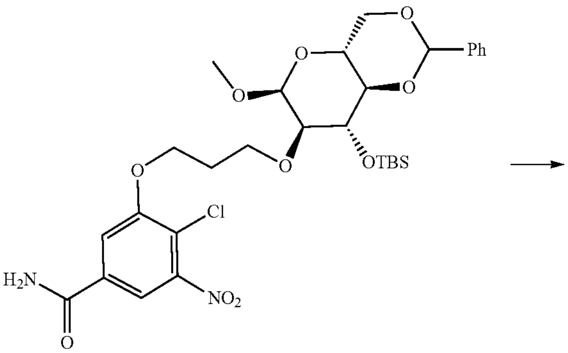

1-15

-continued

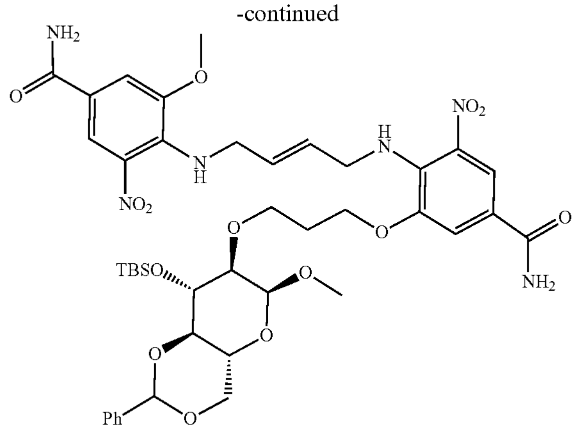

1-16

Compound 1-15 (240 mg, 367 μmol) was dissolved in ethanol (4 mL), and compound 1-6 (206 mg, 735 μmol), diisopropylethylamine (475 mg, 3.67 mmol, 610 μL) and sodium bicarbonate (62 mg, 734.85 μmol) were serially added, the reaction system was stirred at 150° C. for 3 h in a microwave condition, and concentrated under reduced pressure, and the crude product was purified by silica gel column chromatography (dichloromethane/methanol (v/v) =1/0-5/1) to obtain compound 1-16.

MS (ESI) m/z $(M+H)^+$=897.4.

Step 14: Preparation of Compound 1-17

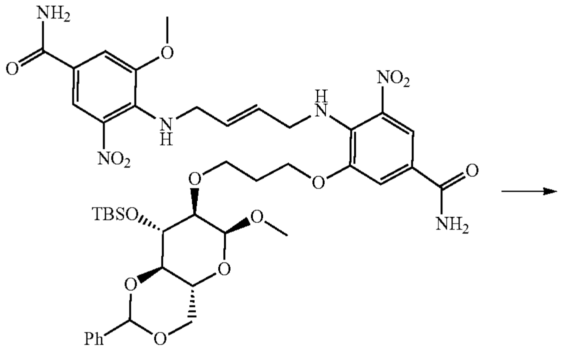

1-16

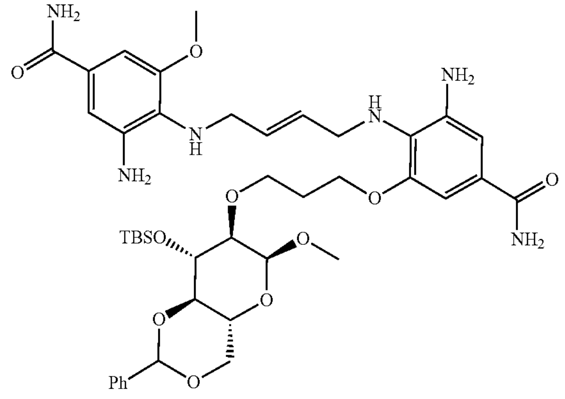

1-17

Compound 1-16 (220 mg, 245.26 μmol) was dissolved in methanol (4 mL) at 0° C., an aqueous solution (1 mL) of sodium dithionite (427.01 mg, 2.45 mmol) and aqueous ammonia (910.00 mg, 7.01 mmol, 1 mL, 27% aqueous solution) were serially added, and the reaction system was heated to 15° C. and stirred for 1 h, diluted with methanol (10 mL) and ethyl acetate (100 mL) and washed with saturated brine (30 mL×3). The organic phase was dried over anhydrous sodium sulfate and filtered, and the filtrate was concentrated under reduced pressure to obtain a crude product 1-17 which was used in the next step directly without further purification.

MS (ESI) m/z $(M+H)^+$=837.3.

Step 15: Preparation of Compound 1-18

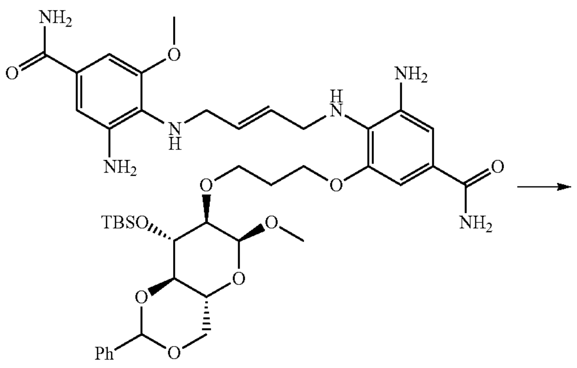

1-17

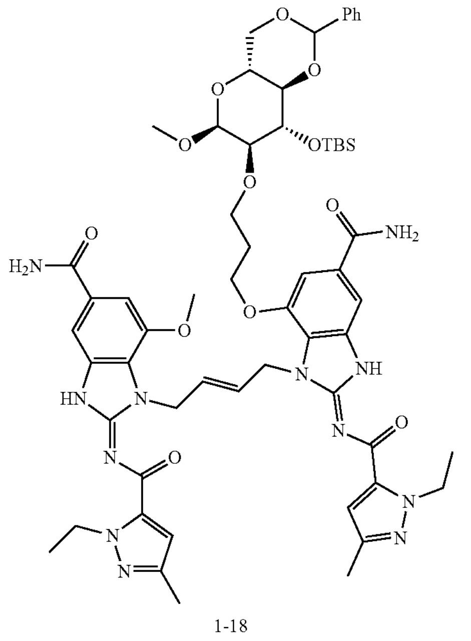

1-18

Compound 1-17 (408 mg, 250.88 μmol) was dissolved in N,N-dimethylformamide (4 mL) at 0° C., compound 1-12 (0.4 M in 1,4-dioxane, 1.57 mL) was added dropwise, then 1-ethyl-(3-dimethylaminopropyl)carbonyldiimine hydrochloride (120 mg, 627.21 μmol) and triethylamine (127 mg, 1.25 mmol) were added, and the reaction system was heated to 15° C. and stirred for 16 h. The reaction was quenched by adding water (2 mL), and the system was diluted with ethyl acetate (100 mL) and washed with saturated brine (30 mL×4). The organic phase was dried over anhydrous sodium sulfate and filtered, the filtrate was concentrated under reduced pressure, and the crude product was purified by high performance preparative silica gel plate chromatography (dichloromethane/methanol (v/v)=10/1) to obtain compound 1-18.

MS (ESI) m/z $(M+H)^+=580.5$.

Step 16: Preparation of Compound 1

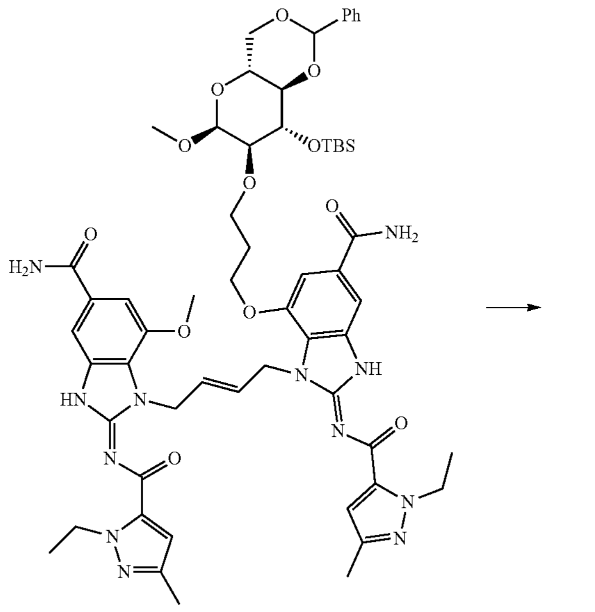

1-18

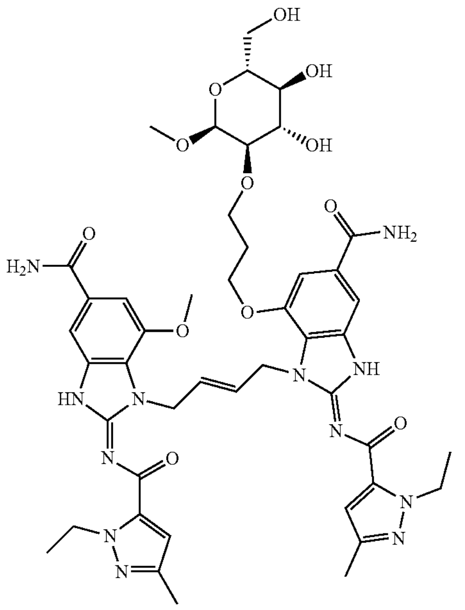

1

Compound 1-18 (120 mg, 103.51 μmol) was dissolved in dichloromethane (2 mL) at 0° C., trifluoroacetic acid (1.23 g, 10.80 mmol, 800 μL) (80% aqueous solution) was added, the reaction system was heated to 15° C. and stirred for 2 h and concentrated under reduced pressure, and the crude product was separated by preparative high performance liquid chromatography (separation condition: column: Boston Green ODS 150 mm×30 mm, 5 μm; mobile phase: (water (0.075% trifluoroacetic acid solution)-acetonitrile); acetonitrile %: 18%-48%) to obtain compound 1 (HPLC retention time: 8.53 min).

MS (ESI) m/z $(M+H)^+=957.1$ $^1H$ NMR (400 MHz, DMSO-$d_6$) δ 12.83 (br s, 2H), 7.97 (br s, 2H), 7.64 (d, J=5.6 Hz, 2H), 7.36 (br d, J=8.4 Hz, 2H), 7.32 (br d, J=5.2 Hz, 2H), 7.25-6.91 (m, 2H), 6.52 (s, 2H), 5.82 (br d, J=4.0 Hz, 2H), 4.92 (br d, J=10.2 Hz, 4H), 4.65 (d, J=3.6 Hz, 1H), 4.52 (br d, J=7.2 Hz, 4H), 4.08 (br s, 2H), 3.75 (s, 3H), 3.27 (br d, J=8.0 Hz, 2H), 3.18 (s, 4H), 3.11-2.92 (m, 3H), 2.11 (d, J=1.6 Hz, 6H).

Example 2

Preparation of Compound 2

Step 1: Preparation of Compound 2-1

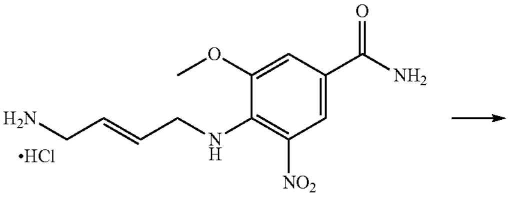

1-6

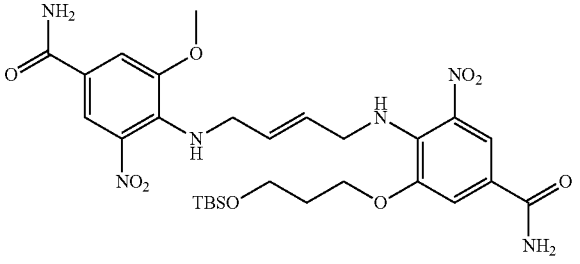

2-1

Compound 1-6 (1.5 g, 4.74 mmol) and compound 1-4 (2.03 g, 5.21 mmol) were dissolved in n-butanol (20 mL), diisopropylethylamine (1.84 g, 14.21 mmol, 2.5 mL) was added, and the reaction system was heated to 120° C. in a sealed tube and stirred for 24 h. The reaction solution was filtered, the filter cake was dried, and the crude product was purified by high performance preparative silica gel plate chromatography (dichloromethane/methanol (v/v)=1/0-10/1) to obtain compound 2-1.

MS (ESI) m/z $(M+Na)^+=655.1$.

Step 2: Preparation of Compound 2-2

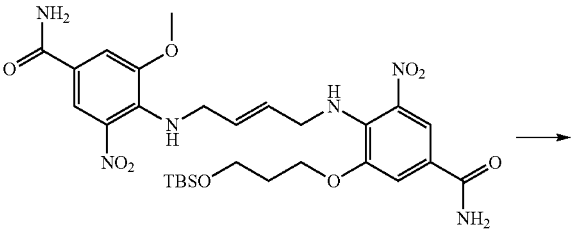

2-1

-continued

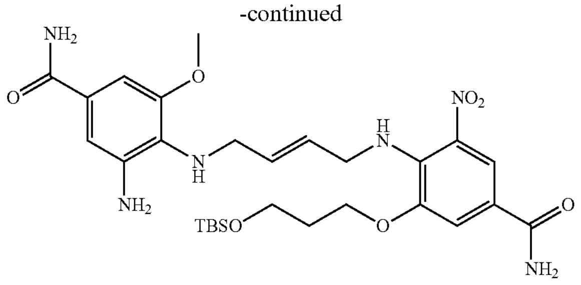

2-2

Compound 2-1 (680 mg, 1.07 mmol) was dissolved in methanol (10 mL) and tetrahydrofuran (5 mL) at 0° C., an aqueous solution (5 mL) of sodium dithionate (1.87 g, 10.75 mmol) and aqueous ammonia (3.36 g, 26.87 mmol, 3.7 mL, 28% aqueous solution) were serially added, and the system was heated to 15° C. and stirred for 1 h. The reaction solution was filtered to remove the solid, and the filtrate was diluted with water (50 mL) and extracted with ethyl acetate (100 mL×3). The organic phases were combined, dried over anhydrous sodium sulfate and filtered, and the filtrate was concentrated under reduced pressure to obtain a crude product 2-2 which was used in the next step directly without further purification.

MS (ESI) m/z $(M+H)^+$=573.1.

Step 3: Preparation of Compound 2-3

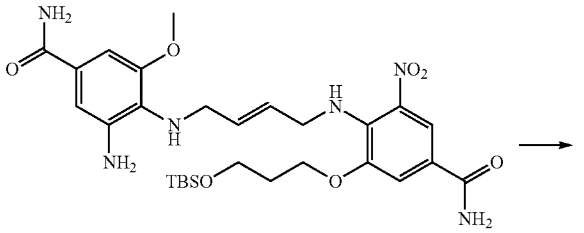

2-2

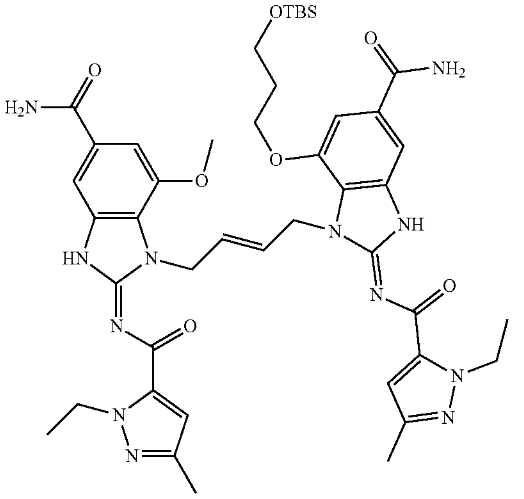

2-3

Compound 2-2 (600 mg, 963.41 μmol) was dissolved in N,N-dimethylformamide (15 mL) at 0° C., compound 1-12 (0.4 M in 1,4-dioxane, 6.02 mL) was added dropwise within 30 min, then 1-ethyl-(3-dimethylaminopropyl)carbonyldiimine hydrochloride (461 mg, 2.41 mmol) and triethylamine (487 mg, 4.82 mmol, 670 μL) were added, and the reaction system was heated to 15° C. and stirred for 16 h. The reaction was quenched by adding water (10 mL), the system was concentrated under reduced pressure to remove the solvent, and the residue was dissolved in a mixed solution of dichloromethane (180 mL) and methanol (20 mL) and washed with saturated brine (50 mL×3). The organic phase was dried over anhydrous sodium sulfate and filtered, the filtrate was concentrated under reduced pressure, and the crude product was purified by high performance preparative silica gel plate chromatography (dichloromethane/methanol (v/v)=20/1) to obtain compound 2-3.

MS (ESI) m/z $(M+H)^+$=895.4.

Step 4: Preparation of Compound 2-4

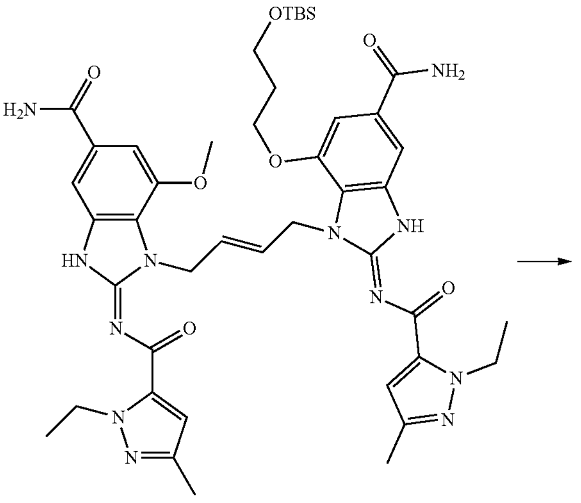

2-3

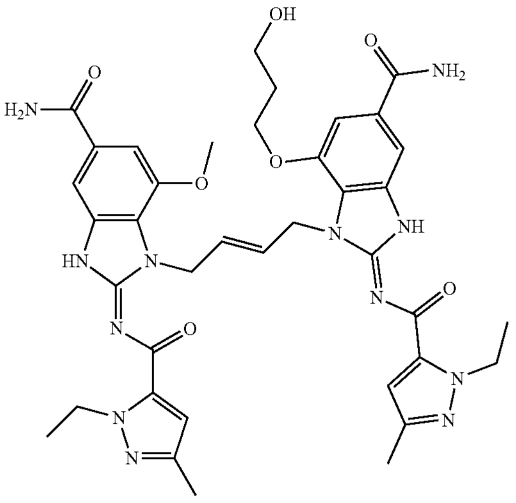

2-4

Compound 2-3 (550 mg, 614.46 μmol) was dissolved in tetrahydrofuran (8 mL), acetic acid (554 mg, 9.22 mmol, 527.14 μL) and tetrabutylammonium fluoride (1.0 M in tetrahydrofuran, 3.69 mL) were serially added, the reaction system was heated to 20° C., stirred for 20 h and filtered to remove the solid, and the filtrate was diluted with water (50 mL) and extracted with a mixed solution of dichloromethane and methanol (dichloromethane/methanol (v/v)=10/1, 60 mL×4). The organic phase was dried with anhydrous sodium sulfate and filtered, the filtrate was concentrated under reduced pressure, and the crude product was purified by flash silica gel column chromatography (dichloromethane/methanol (v/v)=1/0-10/1) to obtain compound 2-4.

MS (ESI) m/z $(M+H)^+$=781.3.

Step 5: Preparation of Compound 2-5

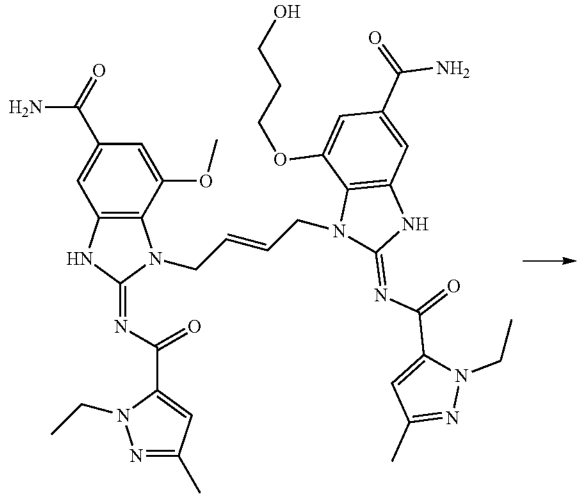

2-4

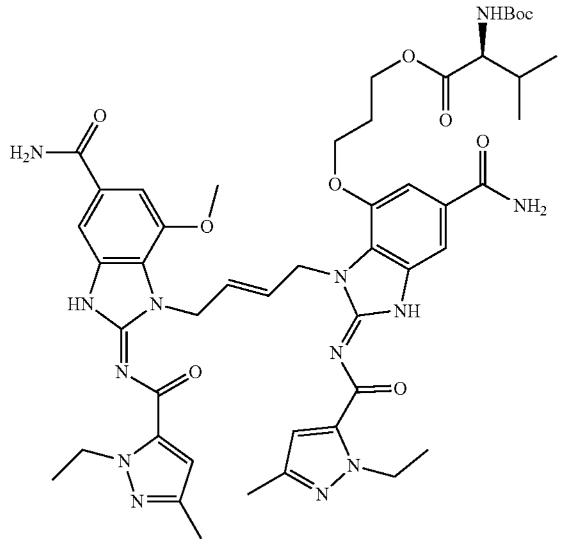

2-5

Compound 2-4 (36 mg, 166.49 μmol) was dissolved in dichloromethane (6 mL) at 0° C., N-Boc-L-valine (65 mg, 83.24 μmol), 1-ethyl-(3-dimethylaminopropyl)carbodiimide hydrochloride (24 mg, 124.87 μmol) and N,N-dimethylaminopyridine (2 mg, 16.65 μmol) were serially added, the reaction system was heated to 15° C. and stirred for 20 h, and diluted with ethyl acetate (100 mL), the organic phase was washed with saturated saline (20 mL×2), dried over anhydrous sodium sulfate and filtered, the filtrate was concentrated under reduced pressure, and the crude product was purified by flash silica gel column chromatography (dichloromethane/methanol (v/v)=1/0-5/1) to obtain compound 2-5.

MS (ESI) m/z $(M+H)^+$=980.6.

Step 6: Preparation of Compound 2

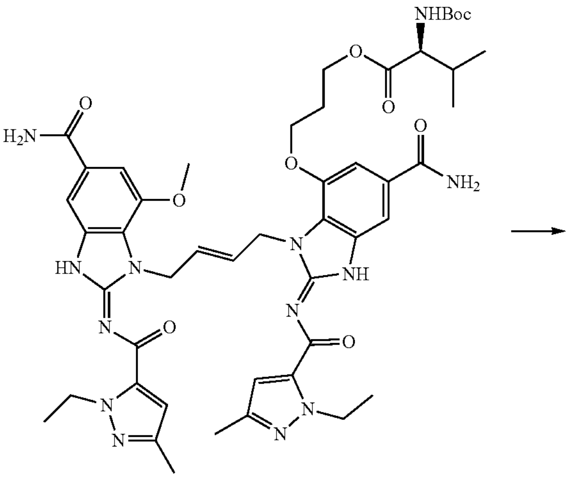

2-5

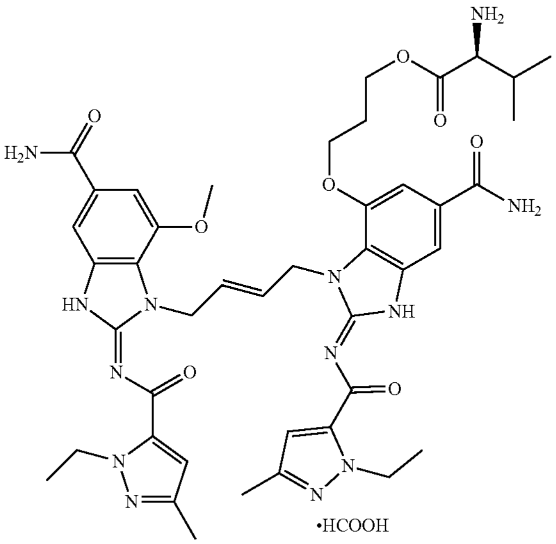

2

Compound 2-5 (85 mg, 42.25 μmol) was dissolved in 1,4-dioxane (2 mL), a solution of hydrogen chloride in 1,4-dioxane (4.0 M, 528.17 μL) was added, the reaction system was stirred at 15° C. for 1 h and concentrated under reduced pressure, and the crude product was separated by preparative high performance liquid chromatography (separation condition: column: Xtimate® C18 150 mm×40 mm, 10 μm; mobile phase: (water (0.2% trifluoroacetic acid solution)-acetonitrile); acetonitrile %: 20%-50%) to obtain compound 2 (HPLC retention time: 6.98 min).

MS (ESI) m/z $(M+H)^+$=880.2.

$^1H$ NMR (400 MHz, DMSO-$d_6$) δ 8.51 (s, 0.3H), 7.59 (s, 1H), 7.56 (s, 1H), 7.30 (s, 1H), 7.27 (s, 1H), 6.59 (s, 1H), 6.56 (s, 1H), 5.86-5.83 (m, 2H), 5.04-5.00 (m, 4H), 4.62-4.56 (m, 4H), 4.21-4.20 (m, 2H), 4.05-4.02 (m, 2H), 3.76 (s, 1H), 3.52-3.51 (m, 4H), 2.20 (s, 3H), 2.19 (s, 3H), 2.07-2.05 (m, 1H), 1.97-1.94 (m, 1H), 1.36-1.31 (m, 6H), 0.96-0.94 (m, 3H), 0.92-0.90 (m, 3H).

Example 3

Preparation of Compound 3

Step 1: Preparation of Compound 3-3

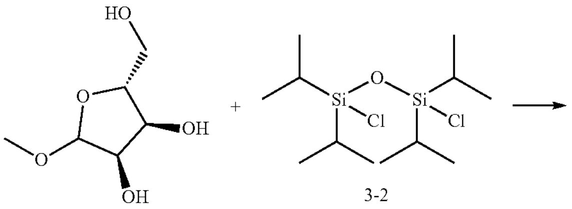

3-1 3-2

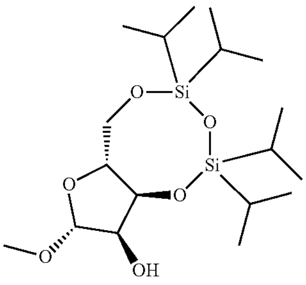

3-3

Compound 3-1 (10 g, 60.9 mmol) was dissolved in pyridine (30 mL), compound 3-2 (23 g, 73.1 mmol) was added, the reaction system was stirred at room temperature for 3 h and diluted with ethyl acetate (800 mL). The organic phase was washed with saturated saline (400 mL×2), dried over anhydrous sodium sulfate and filtered, the filtrate was concentrated under reduced pressure, and the crude product was purified by flash silica gel column chromatography (petroleum ether/ethyl acetate (v/v)=1/0-1/9) to obtain compound 3-3.

$^1$H NMR (400 MHz, Chloroform-d) δ 4.82 (s, 1H), 4.50 (t, J=5.3 Hz, 1H), 4.09-3.98 (m, 3H), 3.75 (dd, J=10.5, 8.7 Hz, 1H), 3.32 (s, 3H), 2.97 (s, 1H), 1.09-1.02 (m, 28H).

Step 2: Preparation of Compound 3-4

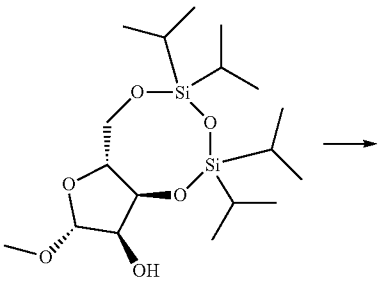

3-3

-continued

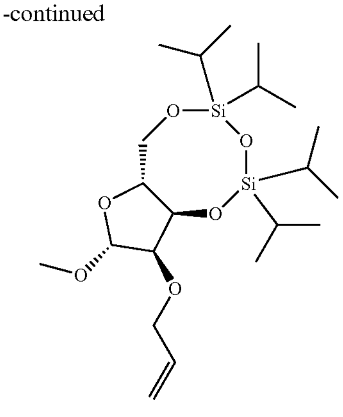

3-4

Compound 3-3 (11 g, 27.1 mmol) was dissolved in tetrahydrofuran (150 mL) under nitrogen atmosphere, allyl methyl carbonate (4.72 g, 40.65 mmol), tris(dibenzylideneacetone)dipalladium (1.24 g, 1.36 mmol) and 1,1'-bis (diphenylphosphine)ferrocene (2.31 g, 5.42 mmol) were serially added, the reaction system was heated to 80° C. and stirred for 3 h, then cooled to room temperature and filtered, the filtrate was concentrated under reduced pressure to dryness, and the crude product was purified by flash silica gel column chromatography (petroleum ether/ethyl acetate (v/v)=1/0-9/1) to obtain compound 3-4.

$^1$H NMR (400 MHz, Chloroform-d) δ 5.92 (ddt, J=16.6, 10.8, 5.4 Hz, 1H), 5.35-5.24 (m, 1H), 5.18 (d, J=10.3 Hz, 1H), 4.76 (s, 1H), 4.46 (dd, J=7.8, 4.2 Hz, 1H), 4.36 (dd, J=13.1, 5.2 Hz, 1H), 4.16 (dd, J=13.2, 5.8 Hz, 1H), 4.07-3.97 (m, 2H), 3.87 (dd, J=11.9, 5.7 Hz, 1H), 3.77 (d, J=4.3 Hz, 1H), 3.32 (s, 3H), 1.13-0.99 (m, 28H).

Step 3: Preparation of Compound 3-5

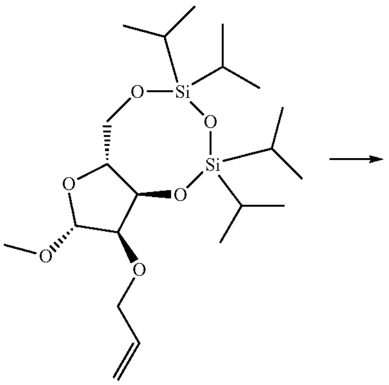

3-4

-continued

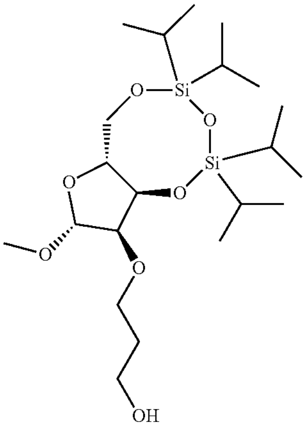

3-5

Compound 3-4 (2.0 g, 4.48 mmol) was dissolved in tetrahydrofuran (20 mL) under nitrogen atmosphere, 9-borabicyclo[3.3.1]nonane (26.9 mL, 0.5 mol/L) was added, and the reaction system was stirred at room temperature for 16 h, then cooled to 0° C., added with a 1.0 M aqueous sodium hydroxide solution (28 mL), added dropwise slowly with hydrogen peroxide solution (28 mL, 30% aqueous solution), and then heated to room temperature and stirred for 3 h. The reaction was quenched by adding a saturated sodium thiosulfate solution (50 mL), and the system was extracted with dichloromethane (300 mL). The organic phase was dried over anhydrous sodium sulfate and filtered, the filtrate was concentrated under reduced pressure to dryness, and the crude product was purified by flash silica gel column chromatography (petroleum ether/ethyl acetate (v/v)=1/0-3/2) to obtain compound 3-5.

$^1$H NMR (400 MHz, Chloroform-d) δ 4.77 (s, 1H), 4.48 (dd, J=7.7, 4.5 Hz, 1H), 4.01-3.72 (m, 8H), 3.70 (d, J=4.5 Hz, 1H), 3.33 (s, 3H), 1.95-1.86 (m, 1H), 1.78-1.65 (m, 1H), 1.10-1.03 (m, 28H).

Step 4: Preparation of Compound 3-6

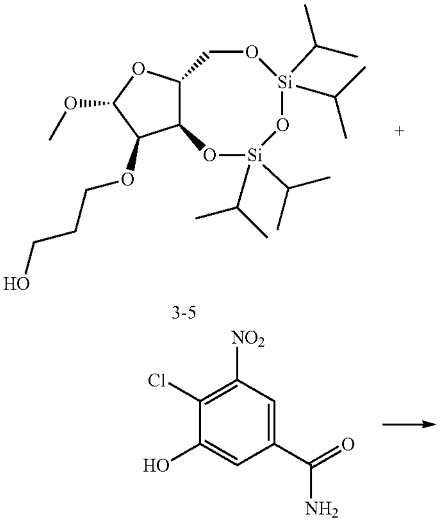

3-5

1-3

-continued

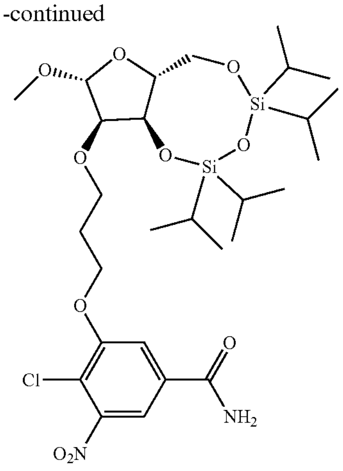

3-6

Compound 3-5 (859 mg, 1.85 mmol), compound 1-3 (440 mg, 2.03 mmol) and triphenylphosphine (630 mg, 2.4 mmol) were dissolved in dichloromethane (45 mL) under nitrogen atmosphere, diisopropyl azodicarboxylate (486 mg, 2.4 mmol) was added dropwise, and the reaction system was stirred at room temperature for 2 h. The reaction was quenched by adding a saturated ammonium chloride solution (100 mL), and the system was extracted with dichloromethane (200 mL). The organic phase was dried over anhydrous sodium sulfate and filtered, the filtrate was concentrated, and the crude product was purified by flash silica gel column chromatography (petroleum ether/dichloromethane (v/v)=1/0-7/3) to obtain compound 3-6.

MS (ESI) m/z $(M-31)^+$=631.4.

$^1$H NMR (400 MHz, Chloroform-d) δ 7.76 (d, J=1.8 Hz, 1H), 7.67 (d, J=1.9 Hz, 1H), 7.14 (d, J=2.2 Hz, 1H), 4.73 (s, 1H), 4.47 (dd, J=7.6, 4.3 Hz, 1H), 4.31 (td, J=6.2, 1.7 Hz, 2H), 4.09-3.94 (m, 3H), 3.87-3.76 (m, 2H), 3.71 (d, J=4.3 Hz, 1H), 3.30 (s, 3H), 2.18-2.13 (m, 2H), 2.01 (s, 1H), 1.51-1.41 (m, 1H), 1.40-1.21 (m, 4H), 1.11-0.96 (m, 28H).

Step 5: Preparation of Compound 3-7

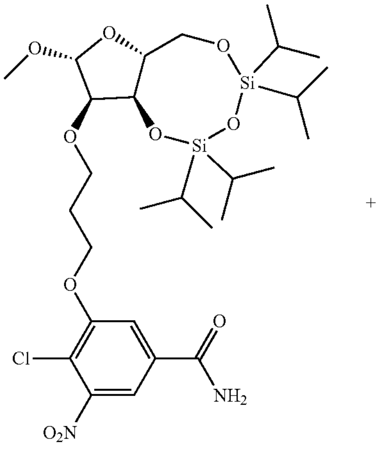

3-6

-continued

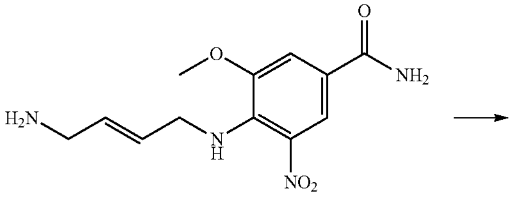

1-6

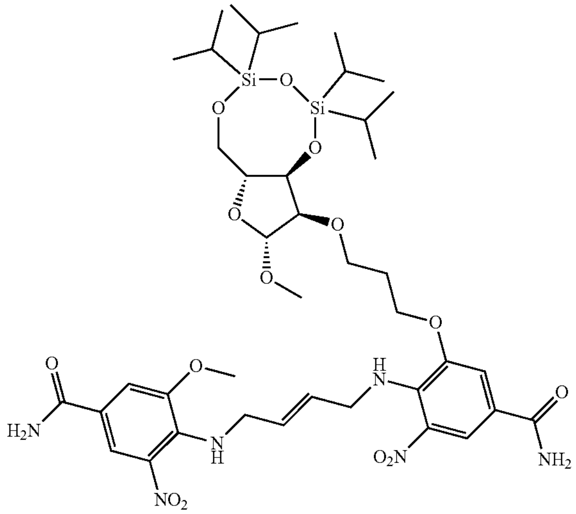

3-7

Compound 3-6 (510 mg, 0.77 mmol) and compound 1-6 (414 mg, 1.31 mmol) were dissolved in n-butanol (6 mL) under nitrogen atmosphere, sodium bicarbonate (123 mg, 1.46 mmol) and N,N-diisopropylethylamine (995 mg, 7.70 mmol) were serially added, the reaction system was heated to 140° C. for 4 h in a microwave tube, then cooled to room temperature and concentrated under reduced pressure to remove the solvent, and the crude product was purified by flash silica gel column chromatography (dichloromethane/methanol (v/v)=1/0-9/1) to obtain compound 3-7.

MS (ESI) m/z $(M+H)^+$=907.6.

Step 6: Preparation of Compound 3-8

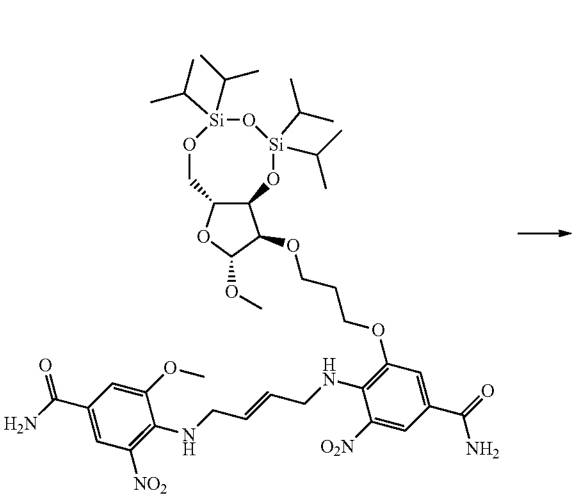

3-7

-continued

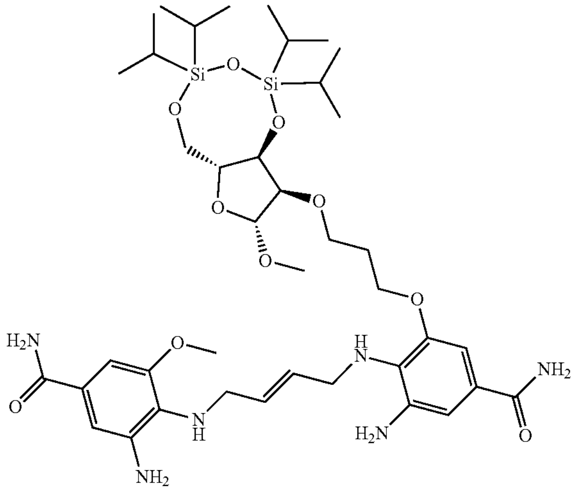

3-8

Compound 3-7 (220 mg, 0.24 mmol) was dissolved in a mixed solution of tetrahydrofuran and methanol (16 mL, 5/1 v/v) at 0° C., an aqueous solution (4.0 mL) of sodium dithionite (1.06 g, 6.07 mmol) and a 28% aqueous ammonia solution (1.58 g, 12.14 mmol) were added dropwise serially, and the reaction system was stirred at this temperature for 3 min, then heated to 22° C. and stirred for 2 h, added with a saturated sodium chloride solution (30 mL) and extracted with ethyl acetate (100 mL). The organic phase was dried with anhydrous sodium sulfate and filtered, the filtrate was concentrated under reduced pressure to dryness, and the crude product was purified by flash silica gel column chromatography (dichloromethane/methanol (v/v)=1/0-9/1) to obtain compound 3-8.

MS (ESI) m/z $(M+H)^+$=847.4.

Step 7: Preparation of Compound 3-9

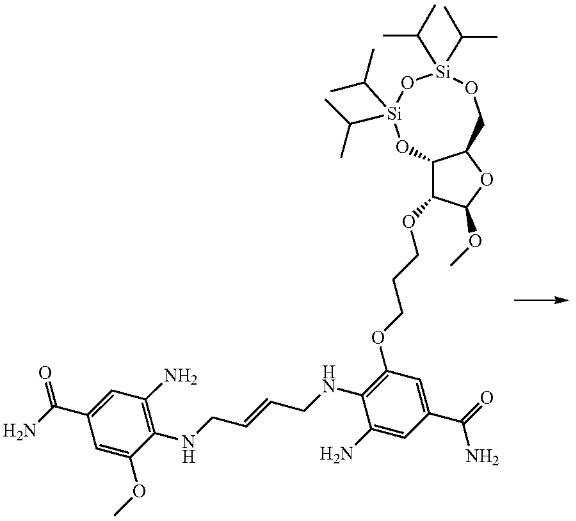

3-8

-continued

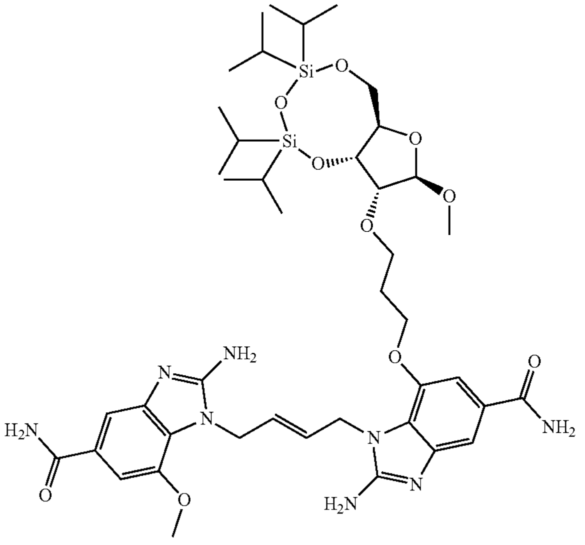

3-9

-continued

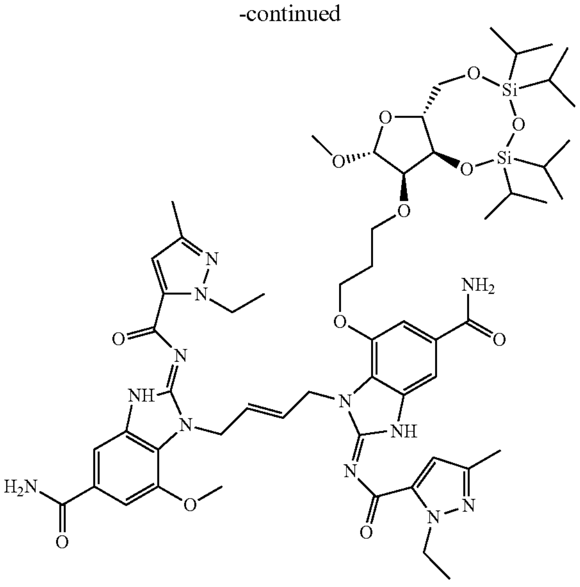

3-10

Compound 3-8 (80 mg, 0.094 mmol) was dissolved in methanol (10 mL), cyanogen bromide (10 mg, 0.094 mmol) was added, and the reaction system was stirred at room temperature for 16 h and concentrated under reduced pressure to obtain a crude product 3-9.

MS (ESI) m/z $(M+H)^+$=897.4

Step 8: Preparation of Compound 3-10

Compound 3-9 (100 mg, 0.11 mmol) was dissolved in N-methylpyrrolidinone (10 mL), 1-ethyl-3-methylpyrazole-5-carboxylic acid (86 mg, 0.56 mmol), 1-(3-dimethylaminopropyl)-3-ethylcarbodiimide hydrochloride (53.5 mg, 0.28 mmol), 1-hydroxybenzotriazole (38 mg, 0.28 mmol) and triethylamine (113 mg, 1.12 mmol) were serially added, and the reaction system was stirred at room temperature for 65 h. The reaction was quenched by adding water (20 mL), and the system was extracted with dichloromethane (60 mL). The organic phase was dried over anhydrous sodium sulfate and filtered, the filtrate was concentrated under reduced pressure to dryness, and the crude product was purified by flash silica gel column chromatography (dichloromethane/methanol (v/v)=1/0-9/1) to obtain compound 3-10.

MS (ESI) m/z $(M+H)^+$=1169.

Step 9: Preparation of Compound 3

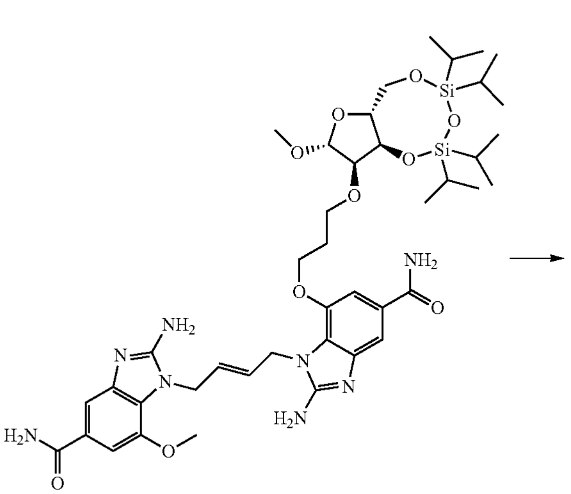

3-9

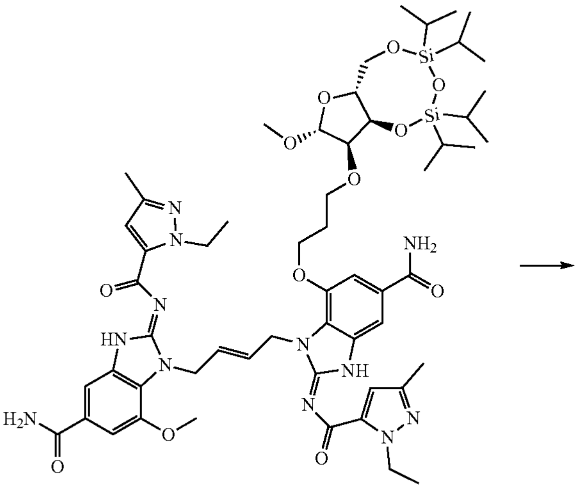

3-10

-continued

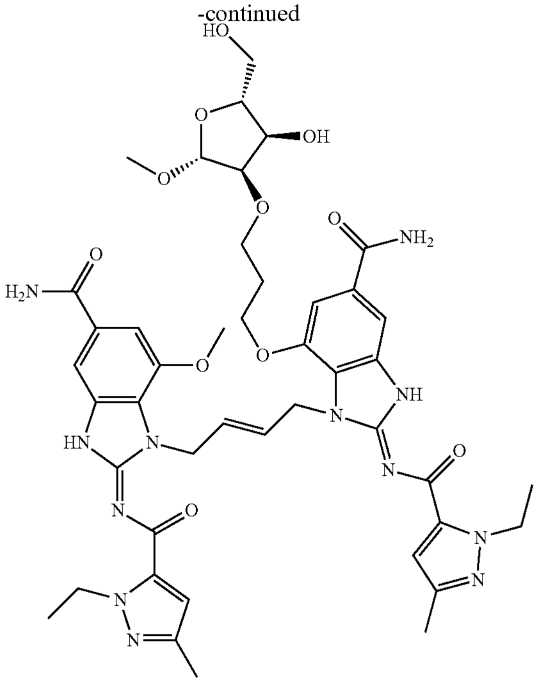

3

Compound 3-10 (73 mg, 0.062 mmol) was dissolved in tetrahydrofuran (5 mL), tetrabutylammonium fluoride (1.0 mL, 1.0 mol/L in tetrahydrofuran) was added, the reaction system was stirred at room temperature for 2 h and concentrated under reduced pressure to dryness, and the crude product was purified by high performance liquid chromatography (separation condition: column: Xtimate® C18 250 mm×21.2 mm, 10 μm; mobile phase: (water (10 mM ammonium bicarbonate)-acetonitrile); flow rate: 30 mL/min) to obtain compound 3 (HPLC retention time: 3.76 min).

MS (ESI) m/z $(M+H)^+$=927.4.

$^1$H NMR (400 MHz, DMSO-$d_6$) δ 12.79 (s, 2H), 7.96 (s, 2H), 7.63 (dd, J=3.5, 1.2 Hz, 2H), 7.39-7.22 (m, 4H), 6.50 (s, 2H), 5.87-5.76 (m, 2H), 4.91 (dd, J=10.1, 4.2 Hz, 4H), 4.79 (d, J=6.8 Hz, 1H), 4.69 (d, J=1.6 Hz, 1H), 4.62 (t, J=5.6 Hz, 1H), 4.51 (q, J=7.1 Hz, 4H), 4.08 (t, J=6.4 Hz, 2H), 3.93 (q, J=5.6 Hz, 1H), 3.77-3.71 (m, 4H), 3.67-3.43 (m, 5H), 3.19 (s, 3H), 2.10 (d, J=1.3 Hz, 6H), 1.82-1.81 (m, 2H), 1.26 (t, J=7.1 Hz, 6H).

Example 4

Preparation of Compound 4

Step 1: Preparation of Compound 4-1

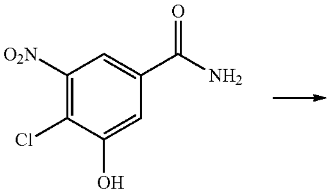

1-3

-continued

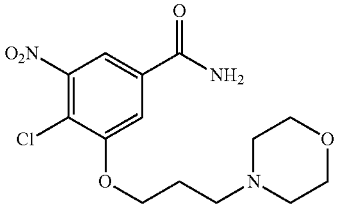

4-1

Compound 1-3 (2.6 g, 12.0 mmol), 3-(4-morpholine)-1-propanol (2.44 g, 16.8 mmol) and triphenylphosphine (4.72 g, 18.0 mmol) were dissolved in dichloromethane (50 mL) at 0° C., diisopropyl azodicarboxylate (3.64 g, 16.8 mmol) was added dropwise, and the reaction system was heated to room temperature and stirred for 4 h. The reaction was quenched by adding water (100 mL), and the system was extracted with dichloromethane (200 mL). The organic phase was dried over anhydrous sodium sulfate and filtered, the filtrate was concentrated under reduced pressure to dryness, and the crude product was purified by flash silica gel column chromatography (dichloromethane/methanol (v/v)=1/0-9/1) to obtain compound 3-10.

MS (ESI) m/z $(M+H)^+$=344.0.

Step 2: Preparation of Compound 4-2

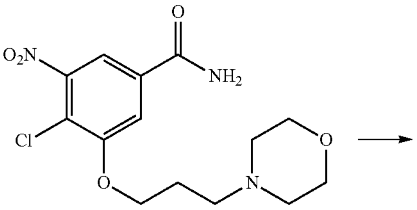

4-1

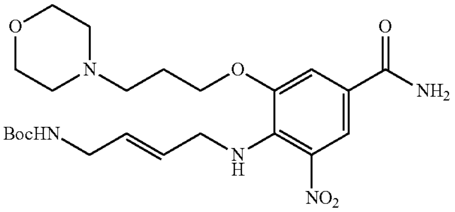

4-2

Compound 4-1 (1.6 g, 4.66 mmol), tert-butyl (4-aminobut-2-en-1-yl)carbamate (1.06 g, 5.69 mmol) and N,N-diisopropylethylamine (1.57 g, 12.12 mmol) were dissolved in ethanol (20 mL), the reaction system was heated to 120° C. in a sealed tube and stirred for 42 h, then cooled to room temperature and concentrated under reduced pressure to remove the solvent, and the crude product was purified by flash silica gel column chromatography (dichloromethane/methanol (v/v)=1/0-9/1) to obtain compound 3-10.

MS (ESI) m/z $(M+H)^+$=494.2.

Step 3: Preparation of Compound 4-3

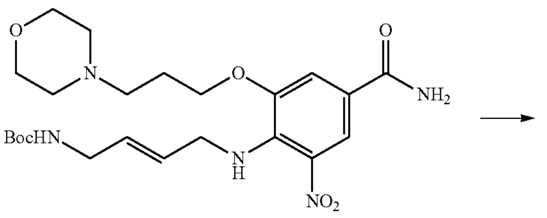

4-2

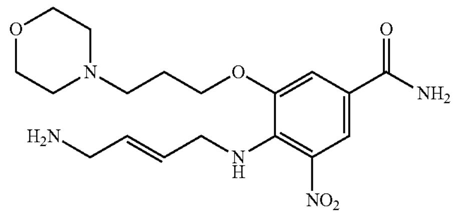

4-3

Compound 4-2 (1.6 g, 3.24 mmol) was dissolved in methanol (18 mL), a solution of hydrogen chloride in dioxane (5 mL, 4.0 mol/L) was added, and the reaction system was stirred at room temperature for 2 h and concentrated under reduced pressure to remove the solvent. Methanol (10 mL) and petroleum ether (100 mL) were serially added, the system was stirred for 10 min and filtered, and the filter cake was dried to obtain compound 4-3.

MS (ESI) m/z $(M+H)^+$=394.0.

Step 4: Preparation of Compound 4-4

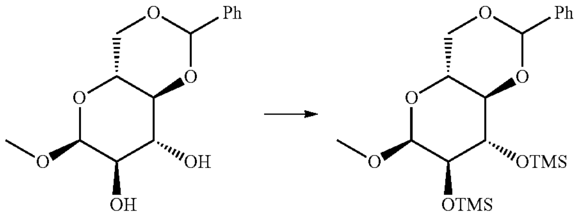

1-8 4-4

Compound 1-8 (40 g, 141.6 mmol) was dissolved in acetonitrile (800 mL) under nitrogen atmosphere, triethylamine (200 mL, 1.42 mol) and chlorotrimethylsilane (50 mL, 394.0 mmol) were serially added, the reaction system was stirred at room temperature for 3 h and filtered, the filtrate was concentrated under reduced pressure to dryness, and n-heptane (800 mL) was added. The reaction system was stirred for 30 min and filtered, and the filtrate was concentrated to dryness to obtain a crude product 4-4 which was used in the next step directly without further purification.

Step 5: Preparation of Compound 4-5

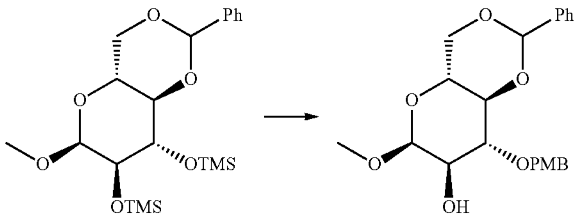

4-4 4-5

Compound 4-4 (5.0 g, 11.7 mmol) was dissolved in dichloromethane (100 mL), a 4A molecular sieve (5.0 g), p-anisaldehyde (1.91 g, 14.0 mmol) and triethylsilane (1.64 g, 14.1 mmol) were serially added, the reaction system was stirred at room temperature for 30 min and then cooled to −78° C., trimethylsilyl trifluoromethanesulfonate (0.78 g, 3.51 mmol) was added dropwise and the reaction system was stirred for 6 h, and a solution of tetrabutylammonium fluoride in tetrahydrofuran (1.0 M, 14.1 mL, 14.1 mmol) was added dropwise, and the reaction system was stirred at room temperature for 8 h and filtered, the filtrate was washed with saturated brine (100 mL), dried over anhydrous sodium sulfate and filtered, the filtrate was concentrated under reduced pressure, and the crude product was slurried and purified with a mixed solvent of methanol (35 mL) and water (25 mL) to obtain compound 4-5 which was directly used in the next step directly without further purification.

Step 6: Preparation of Compound 4-6

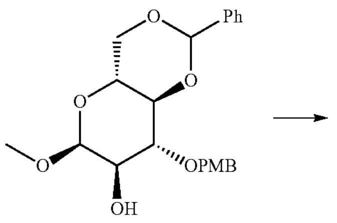

4-5

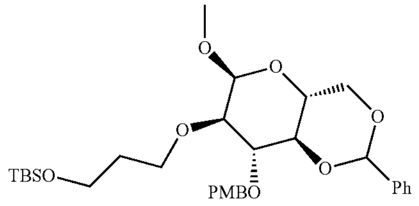

4-6

Compound 4-5 (1.0 g, 2.48 mmol) was dissolved in N,N-dimethylformamide (10 mL) at 0° C. under nitrogen atmosphere, sodium hydride (149 mg, 3.73 mmol, 60%) was added and the reaction system was stirred for 0.5 h, (3-bromopropoxy)-tert-butyldimethylsilane (1.88 g, 7.42 mmol) was added, and the reaction system was heated to room temperature and stirred for 8 h. The reaction was quenched by adding water (20 mL), and the system was diluted with n-heptane (30 mL) and separated. The organic phase was washed with water (10 mL), dried over anhydrous sodium sulfate, and concentrated under reduced pressure to obtain compound 4-6 which was used in the next step directly without further purification.

MS (ESI) m/z $(M+Na)^+$=597.3.

Step 7: Preparation of Compound 4-7

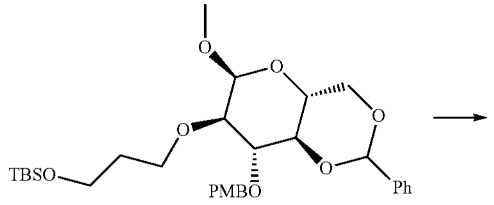

4-6

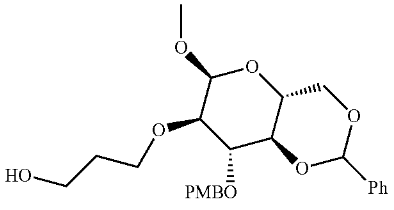

4-7

Compound 4-6 (1.92 g, 3.34 mmol) was dissolved in a solution of tetrabutylammonium fluoride in tetrahydrofuran (1.0 M, 5 mL) under nitrogen atmosphere, the reaction system was stirred at room temperature for 1 h, concentrated under reduced pressure to remove the solvent, added with water (20 mL) and filtered, and the filter cake was added to a mixed solvent of methanol (8 mL) and water (16 mL), slurried, filtered and dried to obtain compound 4-7 which was used in the next step directly without further purification.

MS (ESI) m/z $(M+Na)^+=483.3$.

Step 8: Preparation of Compound 4-8

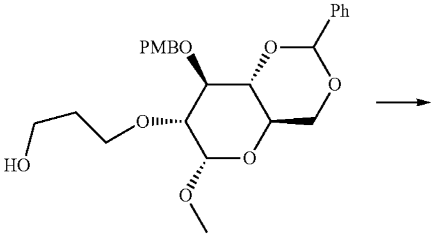

4-7

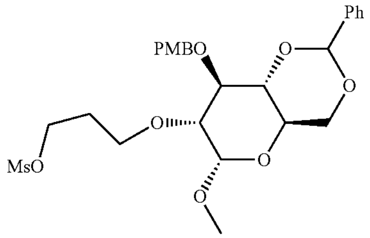

4-8

Compound 4-7 (2.0 g, 4.34 mmol) was dissolved in tetrahydrofuran (40 mL), triethylamine (1.32 g, 13.0 mmol) and methanesulfonyl chloride (995 mg, 8.69 mmol) were serially added, and the reaction system was stirred at room temperature for 2 h. The reaction was quenched by adding water (20 mL), and the system was extracted with ethyl acetate (40 mL). The organic phase was washed with saturated brine (40 mL), dried over anhydrous sodium sulfate and filtered, and the filtrate was concentrated under reduced pressure to obtain a crude product 4-8.

MS (ESI) m/z $(M+18)^+=556.0$.

Step 9: Preparation of Compound 4-9

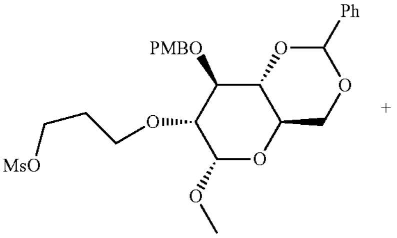

4-8

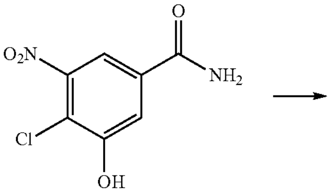

1-3

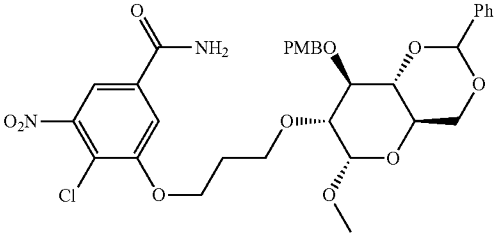

4-9

Compound 4-8 (2.5 g, 4.65 mmol) and compound 1-3 (1.08 g, 5.02 mmol) were dissolved in N,N-dimethylformamide (30 mL), potassium carbonate (1.28 g, 9.3 mmol) was added, and the reaction system was heated to 60° C., stirred for 2 h and then cooled to room temperature. The reaction was quenched by adding water (30 mL), the system was extracted with ethyl acetate (60 mL), the organic phase was washed with saturated saline (40 mL), dried over anhydrous sodium sulfate and filtered, the filtrate was concentrated under reduced pressure, and the crude product was purified by flash silica gel column chromatography (petroleum ether/ethyl acetate (v/v)=1/0-4/1) to obtain compound 4-9.

MS (ESI) m/z $(M+H)^+=659.0$.

Step 10: Preparation of Compound 4-10

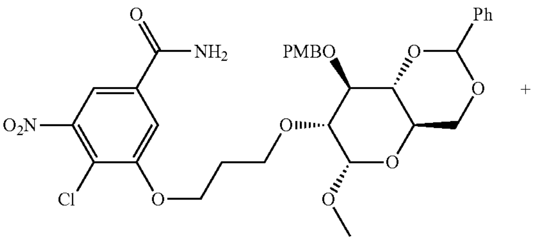

4-9

-continued

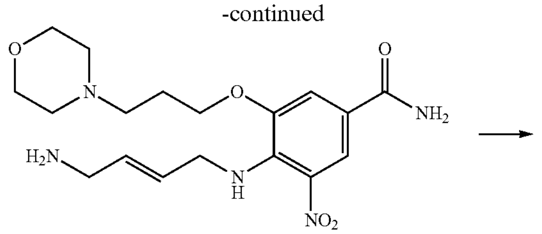

4-3

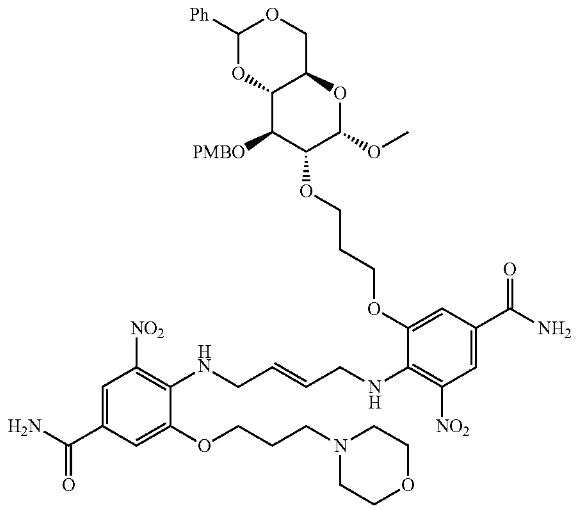

4-10

Compound 4-9 (400 mg, 0.61 mmol) and compound 4-3 (495 mg, 1.15 mmol) were dissolved in n-butanol (7 mL) under nitrogen atmosphere, sodium bicarbonate (107 mg, 1.27 mmol) and N,N-diisopropylethylamine (784 mg, 6.07 mmol) were serially added, the reaction system was heated to 140° C. in a microwave condition and stirred for 4 h, then cooled to room temperature and concentrated under reduced pressure to remove the solvent, and the crude product was purified by flash silica gel column chromatography (dichloromethane/methanol (v/v)=1/0-9/1) to obtain compound 4-10.

MS (ESI) m/z $(M+H)^+$=1016.4.

Step 11: Preparation of Compound 4-11

-continued

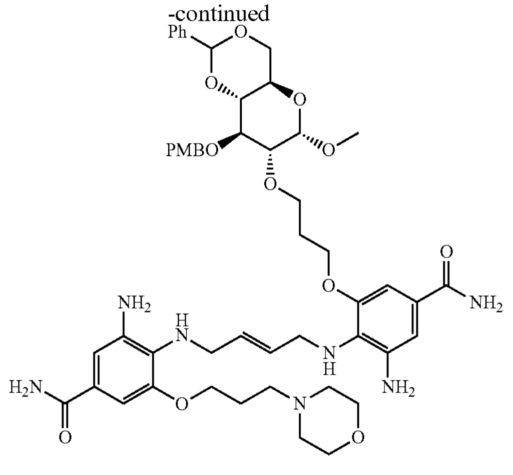

4-11

Compound 4-10 (195 mg, 0.192 mmol) and 28% aqueous ammonia (997 mg, 7.68 mmol) were dissolved in a tetrahydrofuran/methanol solution (12 mL, 4/1 v/v) at 0° C., an aqueous solution (3 mL) of sodium dithionite (669 mg, 3.84 mmol) was added, and the reaction system was stirred at 0° C. for 30 min, heated to room temperature and stirred for 2 h, added with water (30 mL) and extracted with ethyl acetate (120 mL). The organic phase was washed with saturated saline (60 mL), dried over anhydrous sodium sulfate and filtered, the filtrate was concentrated under reduced pressure, and the crude product was purified by flash silica gel column chromatography (dichloromethane/methanol (v/v)=1/0-4/1) to obtain compound 4-11.

MS (ESI) m/z $(M+H)^+$=956.4.

Step 12: Preparation of Compound 4-12

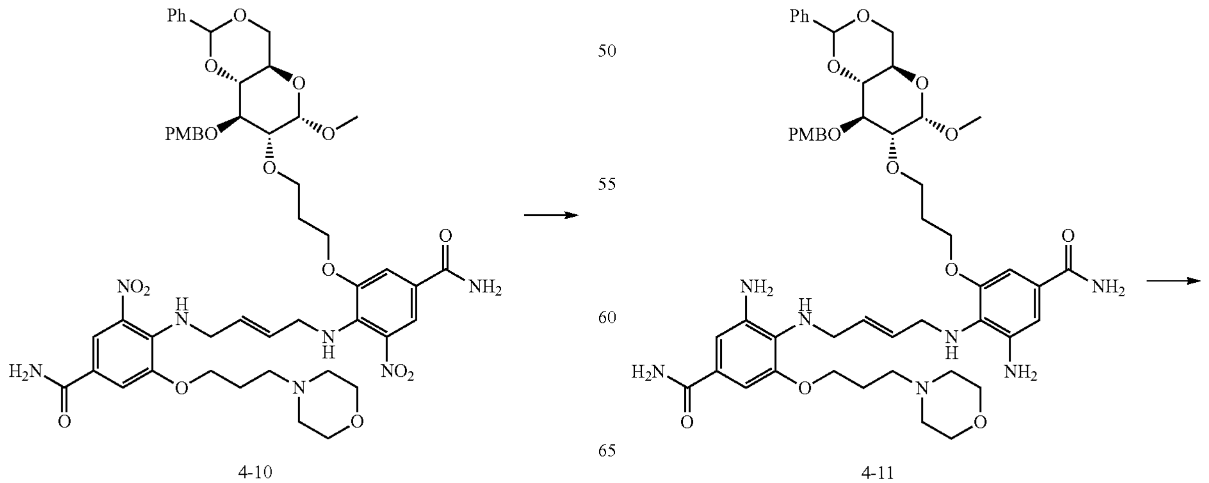

4-10

4-11

-continued

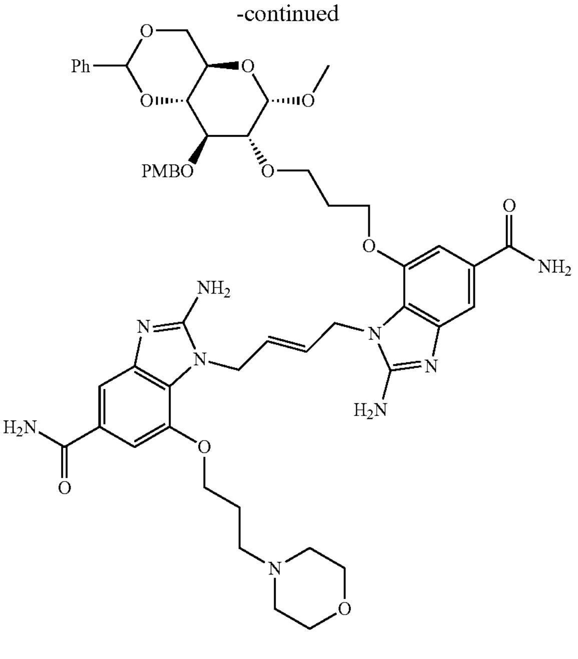

4-12

Compound 4-11 (40 mg, 0.04 mmol) was dissolved in methanol (10 mL), cyanogen bromide (4.2 mg, 0.04 mmol) was added, and the reaction system was stirred at room temperature for 3 h and concentrated under reduced pressure to remove the solvent to obtain a crude product 4-12.

MS (ESI) m/z $(M+H)^+$=1006.4.

Step 13: Preparation of Compound 4-13

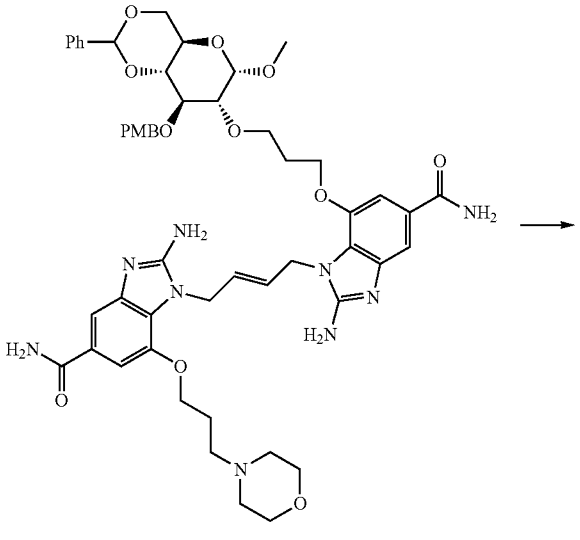

4-12

-continued

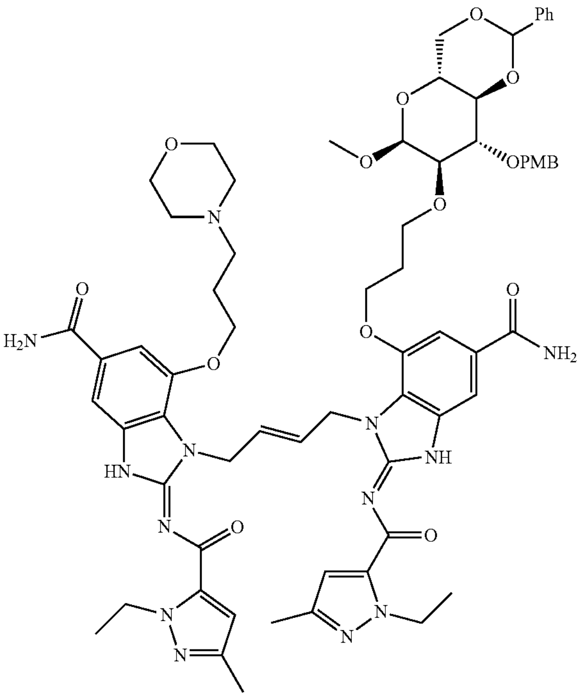

4-13

Compound 4-12 (53 mg, 0.053 mmol) was dissolved in N-methylpyrrolidinone (3 mL), 1-ethyl-3-methylpyrazole-5-carboxylic acid (49 mg, 0.32 mmol), 1-(3-dimethylaminopropyl)-3-ethylcarbodiimide hydrochloride (25 mg, 0.13 mmol), 1-hydroxybenzotriazole (18 mg, 0.13 mol) and triethylamine (64 mg, 0.64 mmol) were serially added, and the reaction system was stirred at room temperature for 42 h. The reaction was quenched by adding water (20 mL), and the system was extracted with dichloromethane (60 mL). The organic phase was dried over anhydrous sodium sulfate and filtered, the filtrate was concentrated under reduced pressure, and the crude product was purified by flash silica gel column chromatography (dichloromethane/methanol (v/v)=1/0-17/3) to obtain compound 4-13.

MS (ESI) m/z $(M+H)^+$=1278.6.

Step 14: Preparation of Compound 4

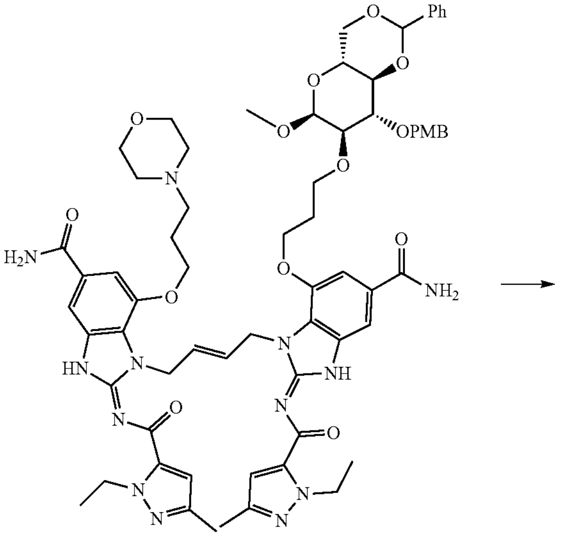

4-13

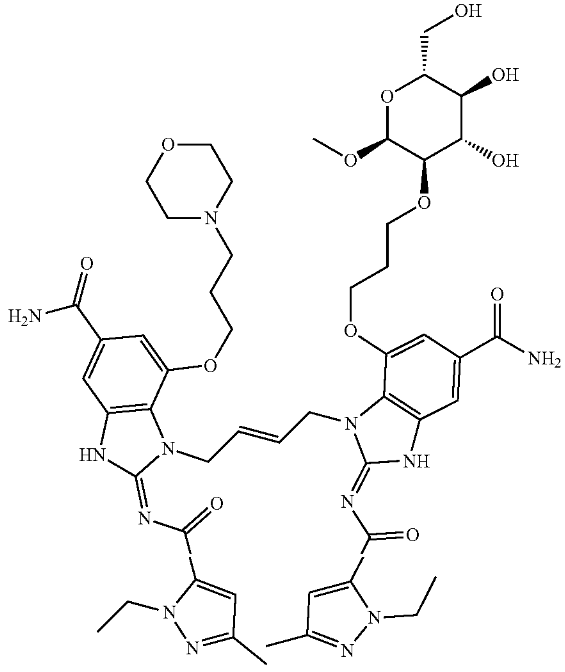

4

Compound 4-13 (10 mg, 0.008 mmol) was dissolved in dichloromethane (3 mL), trifluoroacetic acid (0.2 mL) was added, the reaction system was stirred at room temperature for 2 h and concentrated under reduced pressure to remove the solvent, and the crude product was purified by high performance liquid chromatography (separation condition: column: Xtimate® C18 250 mm×21.2 mm, 10 μm; mobile phase: (water (10 mM ammonium bicarbonate)-acetonitrile); flow rate: 30 mL/min) to obtain compound 4 (HPLC retention time: 3.53 min).

HPLC analysis: column: Waters XBridge 4.6 mm×100 mm, 3.5 μm; mobile phase: (water (10 mM ammonium bicarbonate)-acetonitrile); B %: 5%-95%, 7 min;

MS (ESI) m/z $(M+H)^+$=1070.4.

$^1$H NMR (400 MHz, DMSO-$d_6$) δ 12.81 (s, 2H), 7.95 (s, 2H), 7.66-7.61 (m, 2H), 7.33 (s, 2H), 7.26 (d, J=9.9 Hz, 2H), 6.56 (s, 1H), 6.51 (s, 1H), 5.80 (s, 2H), 4.94-4.91 (s, 6H), 4.62-4.61 (m, 1H), 4.58-4.43 (m, 5H), 3.99 (s, 2H), 3.90 (t, J=6.3 Hz, 2H), 3.63-3.60 (m, 2H), 3.46-3.44 (m, 5H), 3.17-3.15 (m, 2H), 3.15-2.54 (m, 3H), 2.54-2.11 (m, 11H), 1.73-1.53 (m, 5H), 1.32-1.26 (m, 6H).

Example 5

Preparation of Compound 5

Step 1: Preparation of Compound 5-1

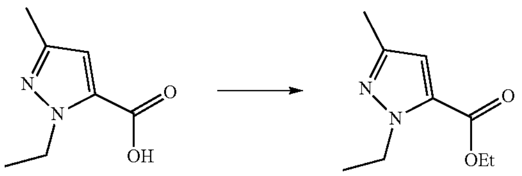

1-10 5-1

Compound 1-10 (10 g, 64.9 mmol) was dissolved in dichloromethane (80 mL), oxalyl chloride (16.5 g, 129.7 mmol, 11.0 mL) and 2 drops of N,N-dimethylformamide were serially added, the reaction system was stirred at room temperature for 2 h, concentrated under reduced pressure to remove the solvent, and the resulting crude product was dissolved in ethanol (80 g, 1.75 mol, 103 mL). The reaction system was stirred at room temperature for 1 h, concentrated under reduced pressure and dissolved in ethyl acetate (400 mL). The organic phase was washed with saturated brine (100 mL×2), dried over anhydrous sodium sulfate and filtered, and the filtrate was concentrated under reduced pressure to obtain a crude product 5-1 which was used in the next step directly without further purification.

MS (ESI) m/z $(M+H)^+$=183.0.

$^1$H NMR (400 MHz, $CDCl_3$) δ 6.59 (s, 1H), 4.53-4.49 (m, 2H), 4.39-4.22 (m, 2H), 2.26 (s, 3H), 1.47-1.28 (m, 6H).

Step 2: Preparation of Compound 5-2

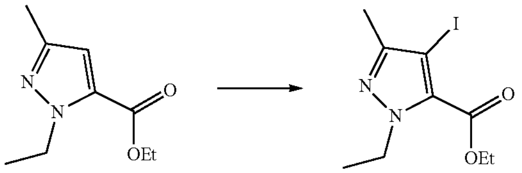

5-1 5-2

Compound 5-1 (10.9 g, 59.8 mmol) was dissolved in N,N-dimethylformamide (200 mL) under nitrogen atmosphere, iodosuccinimide (16.0 g, 71.8 mmol) was added, and the reaction system was heated to 90° C., stirred for 72 h, then cooled to room temperature and diluted with ethyl acetate (400 mL). The organic phase was washed with a saturated sodium thiosulfate solution (100 mL×2) and saturated saline (100 mL×2), dried over anhydrous sodium sulfate and filtered, the filtrate was concentrated under reduced pressure, and the crude product was purified by flash silica gel column chromatography (petroleum ether/ethyl acetate (v/v)=1/0-7/3) to obtain compound 5-2.

MS (ESI) m/z $(M+H)^+$=308.9.

$^1$H NMR (400 MHz, $CDCl_3$) δ 4.53 (q, J=7.2 Hz, 2H), 4.40 (q, J=7.2 Hz, 2H), 2.28 (s, 3H), 1.66-1.38 (m, 6H).

Step 3: Preparation of Compound 5-4

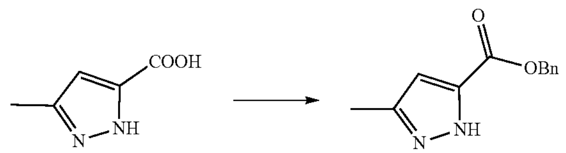

5-3 5-4

Compound 5-3 (20 g, 158.6 mmol) was dissolved in dimethyl sulfoxide (800 mL), potassium bicarbonate (19.1 g, 190.3 mmol) was added, and the reaction system was stirred for 30 min, added with benzyl bromide (27.1 g, 158.6 mmol, 18.8 mL), stirred for 4 h and diluted with ethyl acetate (1000 mL). The organic phase was washed with a saturated sodium bicarbonate solution (300 mL×2) and saturated saline (300 mL×2), dried over anhydrous sodium sulfate and filtered, the filtrate was concentrated under reduced pressure, and the crude product was slurried and purified (with petroleum ether/ethyl acetate (v/v)=20/1, 120 mL) to obtain compound 5-4.

MS (ESI) m/z $(M+H)^+$=216.9.

$^1$H NMR (400 MHz, $CDCl_3$) δ 11.26 (br s, 1H), 8.23-7.95 (m, 5H), 7.91 (s, 1H), 6.00 (s, 2H), 2.98 (s, 3H).

Step 4: Preparation of Compound 5-5

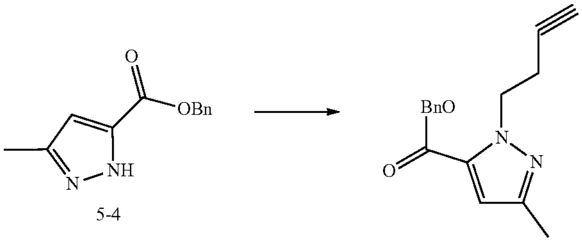

5-4 5-5

Diisopropyl azodicarboxylate (11.2 g, 55.5 mmol, 11.0 mL) and triphenylphosphine (14.6 g, 55.5 mmol) were dissolved in tetrahydrofuran (250 mL) at 0° C., the reaction system was stirred for 30 min, added with 4-pentyn-1-ol (4.67 g, 55.5 mmol), then stirred for 30 min, added with compound 5-4 (10 g, 46.3 mmol), heated to room temperature, stirred for 16 h and diluted with ethyl acetate (500 mL). The organic phase was serially washed with a saturated sodium bicarbonate solution (100 mL×2) and saturated saline (100 mL×2), dried over anhydrous sodium sulfate and filtered, the filtrate was concentrated under reduced pressure, and the crude product was purified by flash silica gel column chromatography (petroleum ether/ethyl acetate (v/v)=1/0-7/3) to obtain compound 5-5.

MS (ESI) m/z $(M+H)^+$=283.0.

$^1$H NMR (400 MHz, $CDCl_3$) δ 7.50-7.31 (m, 5H), 6.66 (s, 1H), 5.31 (s, 2H), 4.59 (t, J=7.2 Hz, 2H), 2.27 (s, 3H), 2.21-2.19 (m, 2H), 2.08-1.95 (m, 2H), 1.96 (t, J=2.4 Hz, 1H).

Step 5: Preparation of Compound 5-6

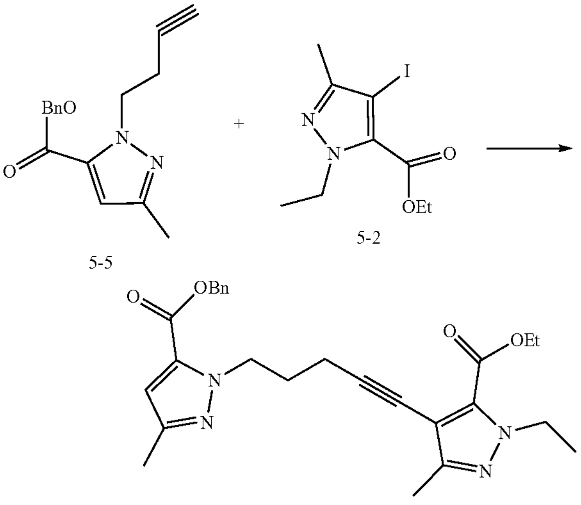

5-5 5-2 5-6

Compound 5-5 (6 g, 21.3 mmol) and compound (7.86 g, 25.5 mmol) were dissolved in toluene (60 mL) under nitrogen atmosphere, cuprous chloride (105 mg, 1.06 mmol), palladium tri-o-tolylphosphine (304 mg, 0.42 mmol), 1,10-o-phenanthroline (1.15 g, 6.38 mmol) and cesium carbonate (13.9 g, 42.5 mmol) were serially added, and the reaction system was stirred at 100° C. for 16 h and diluted with ethyl acetate (500 mL). The organic phase was washed with saturated brine (100 mL×3), dried over anhydrous sodium sulfate and filtered, the filtrate was concentrated under reduced pressure, and the crude product was purified by flash silica gel column chromatography (petroleum ether/ethyl acetate (v/v)=1/0-7/3) to obtain compound 5-6.

MS (ESI) m/z $(M+H)^+$=463.1.

$^1$H NMR (400 MHz, $CDCl_3$) δ 7.50-7.33 (m, 5H), 6.66 (s, 1H), 5.29 (s, 2H), 4.64 (t, J=7.2 Hz, 2H), 4.55-4.43 (m, 2H), 4.37 (q, J=7.2 Hz, 2H), 2.48 (t, J=7.2 Hz, 2H), 2.28 (s, 3H), 2.26 (s, 3H), 2.14 (q, J=7.2 Hz, 2H), 1.40-1.37 (m, 6H).

Step 6: Preparation of Compound 5-7

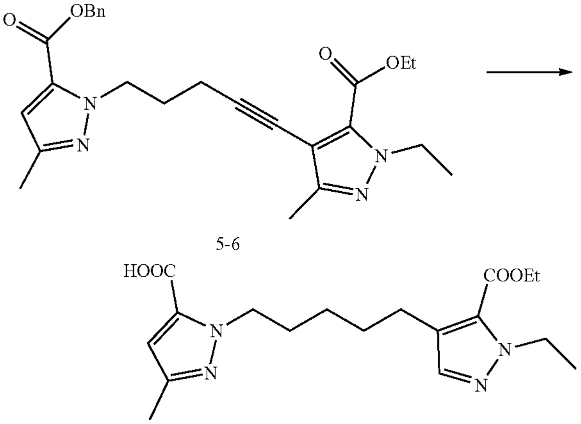

5-6 5-7

Compound 5-6 (7.2 g, 15.6 mmol) was dissolved in ethanol (130 mL), and the reaction system was added with Pd/C (740 mg, 10% wet), stirred for 18 h under hydrogen atmosphere (15 psi), filtered to remove the catalyst, and concentrated under reduced pressure to remove the solvent to obtain a crude product 5-7 which was used in the next step directly without further purification.

MS (ESI) m/z $(M+H)^+$=377.1.

$^1$H NMR (400 MHz, $CDCl_3$) δ 6.70 (s, 1H), 4.50 (q, J=7.2 Hz, 4H), 4.34 (q, J=7.2 Hz, 2H), 2.60 (br t, J=7.6 Hz, 2H), 2.30 (s, 3H), 2.20 (s, 3H), 1.85 (q, J=7.2 Hz, 2H), 1.58-1.44 (m, 2H), 1.40-1.34 (m, 8H).

Step 7: Preparation of Compound 5-8

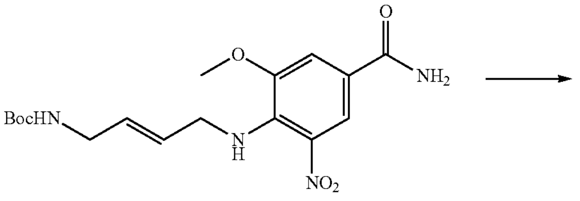

1-5

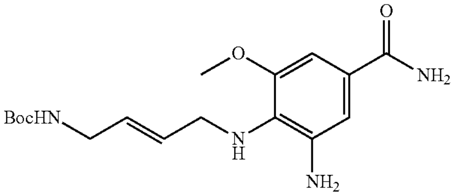

5-8

Compound 1-5 (3.5 g, 9.2 mmol) was dissolved in acetic acid (30 ml), zinc powder (3.01 g, 46.0 mmol) was added, the reaction system was heated to 40° C. and stirred for 4 h, then cooled to room temperature and filtering, and the filtrate was concentrated under reduced pressure to remove the solvent, dissolved in water (5 mL), added with a saturated sodium bicarbonate solution to adjust the pH to 7-8, and extracted with ethyl acetate (600 mL). The organic phase was dried with anhydrous sodium sulfate and filtered, the filtrate was concentrated under reduced pressure, and the crude product was purified by flash silica gel column chromatography (dichloromethane/methanol (v/v)=1/0-23/2) to obtain compound 5-8.

MS (ESI) m/z $(M+H)^+$=351.2

Step 8: Preparation of Compound 5-9

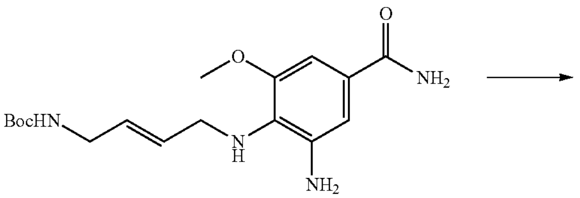

5-8

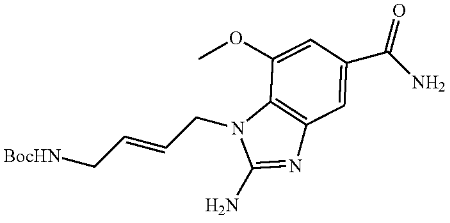

5-9

Compound 5-8 (2.08 g, 5.94 mmol) was dissolved in methanol (25 mL), cyanogen bromide (629 mg, 5.94 mmol) was added, the reaction system was stirred at room temperature for 62 h and filtered, and the filter cake was slurried with petroleum ether (100 mL), purified, filtered, and dried under vacuum to obtain a crude product 5-9 which was used in the next step directly without further purification.

MS (ESI) m/z $(M+H)^+$=376.2

Step 9: Preparation of Compound 5-10

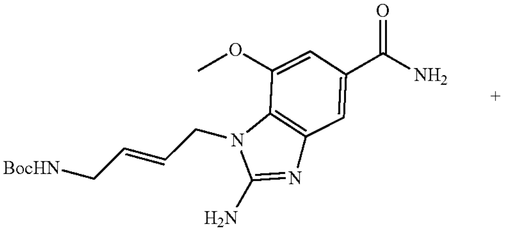

5-9

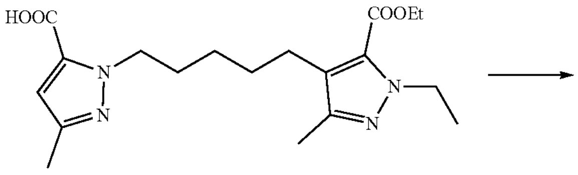

5-7

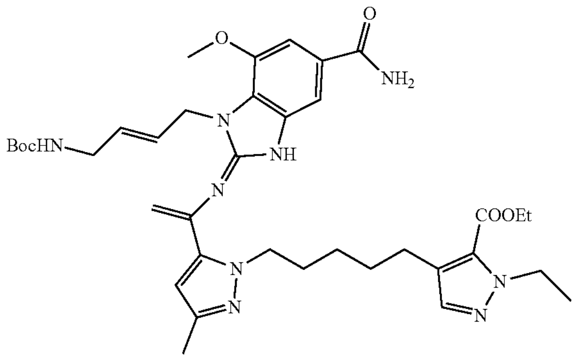

5-10

Compound 5-9 (2.3 g, 6.13 mmol) was dissolved in N-methylpyrrolidinone (30 mL), compound 5-7 (2.19 g, 5.82 mmol), 1-(3-dimethylaminopropyl)-3-ethylcarbodiimide hydrochloride (1.75 g, 9.19 mmol), 1-hydroxybenzotriazole (1.49 g, 11.0 mmol) and triethylamine (3.1 g, 30.6 mmol) were serially added, and the reaction system was stirred at room temperature for 60 h and extracted with ethyl acetate (800 mL). The organic phase was washed with saturated saline (400 mL), dried over anhydrous sodium sulfate and filtered, the filtrate was concentrated under reduced pressure, and the crude product was purified by flash silica gel column chromatography (dichloromethane/methanol (v/v)=1/0-93/7) to obtain compound 5-10.

MS (ESI) m/z $(M+H)^+$=734.6

Step 10: Preparation of Compound 5-11

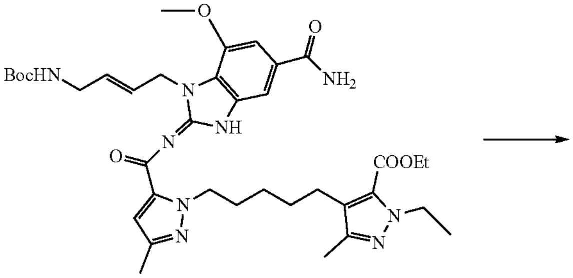

5-10

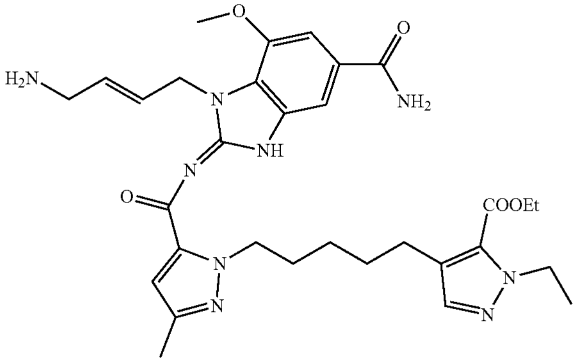

5-11

Compound 5-10 (3.2 g, 4.36 mmol) was dissolved in methanol (20 mL), a solution of hydrogen chloride in methanol (10 mL, 4.0 mol/L) was added, and the reaction system was stirred at room temperature for 2 h and concentrated under reduced pressure to remove the solvent to obtain a crude product 5-11.

MS (ESI) m/z (M+H)+=634.5.

Step 11: Preparation of Compound 5-12

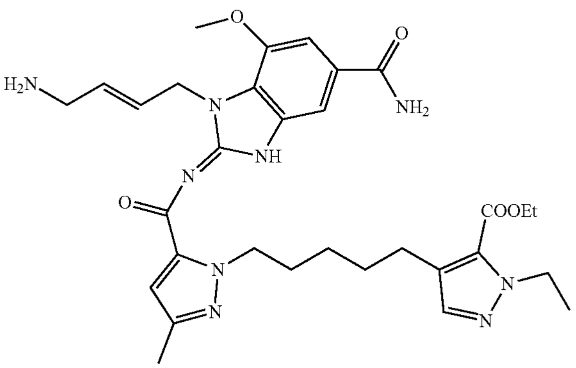

5-11

-continued

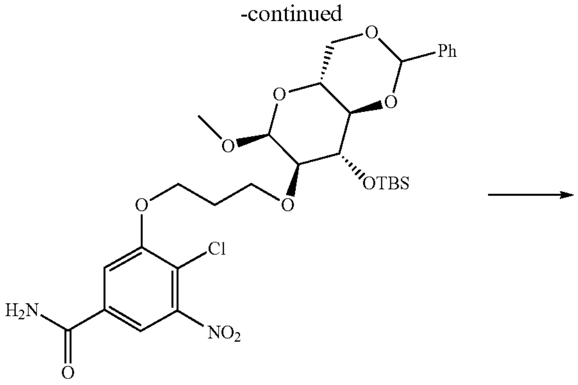

1-15

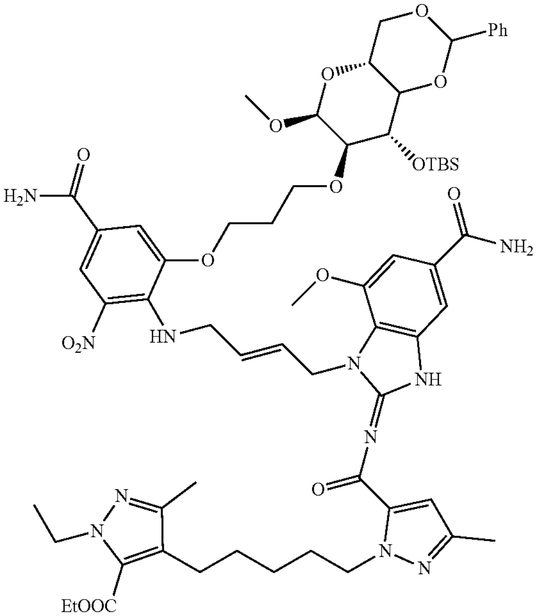

5-12

Compound 1-5 (350 mg, 0.54 mmol) and compound 5-11 (646 mg, 0.96 mmol) were dissolved in n-butanol (3.0 mL) under nitrogen atmosphere, sodium bicarbonate (86 mg, 1.02 mmol) and N, N-diisopropylethylamine (693 mg, 5.36 mmol) were serially added, the reaction system was heated to 140° C. for 4 h in a microwave tube, then cooled to room temperature and concentrated under reduced pressure to remove the solvent, and the crude product was purified by flash silica gel column chromatography (dichloromethane/methanol (v/v)=1/0-9/1) to obtain compound 5-12.

MS (ESI) m/z (M+H)+=1250.5

Step 11: Preparation of Compound 5-13

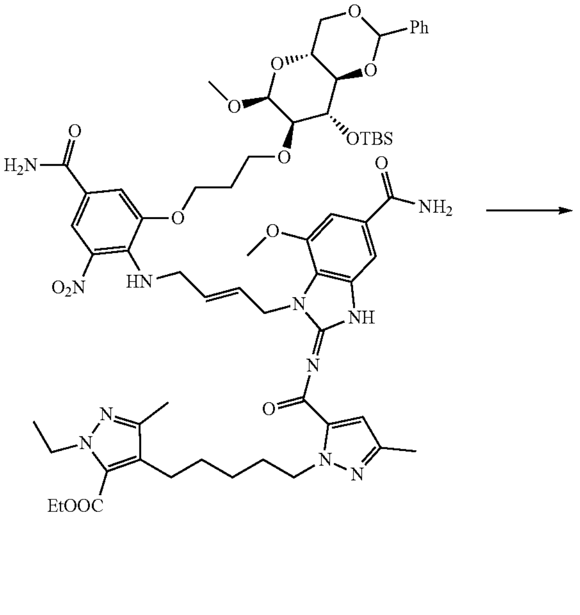

5-12

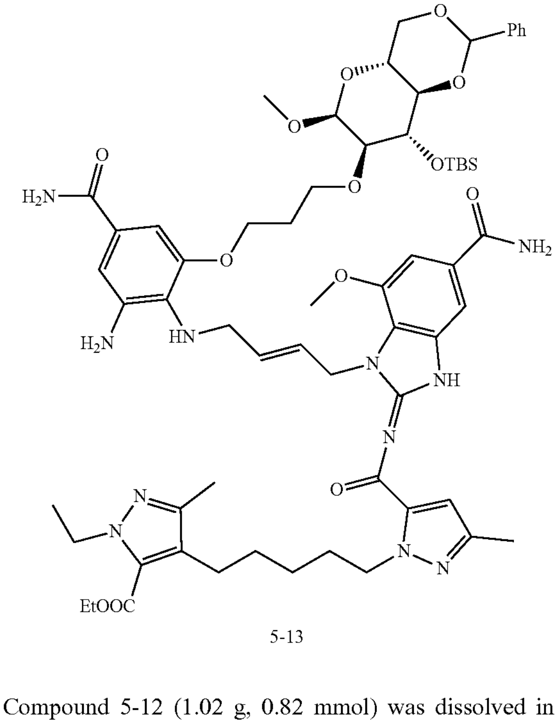

5-13

Compound 5-12 (1.02 g, 0.82 mmol) was dissolved in methanol (20 mL) at 0° C., an aqueous solution (4.0 mL) of sodium dithionite (1.71 g, 9.80 mmol) and 28% ammonia (3.18 g, 24.5 mmol) were serially added, and the reaction system was stirred at room temperature for 3 h, added with water (50 mL) and extracted with ethyl acetate (200 mL). The organic phase was washed with saturated saline (100 mL), dried over anhydrous sodium sulfate and filtered, the filtrate was concentrated under reduced pressure, and the crude product was purified by flash silica gel column chromatography (dichloromethane/methanol (v/v)=1/0-9/1) to obtain compound 5-13.

MS (ESI) m/z $(M+H)^+$=1220.8.

Step 12: Preparation of Compound 5-14

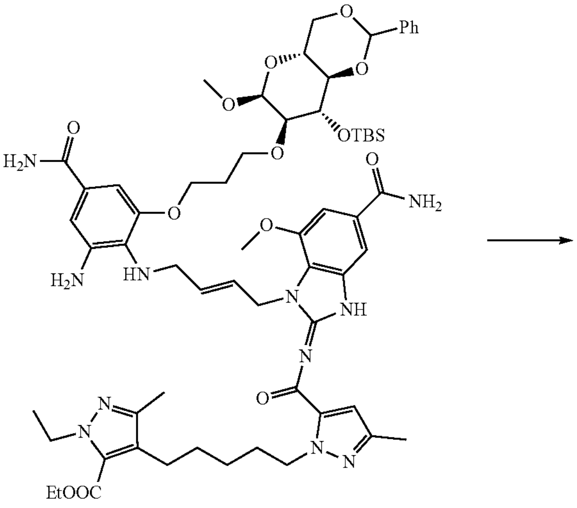

5-13

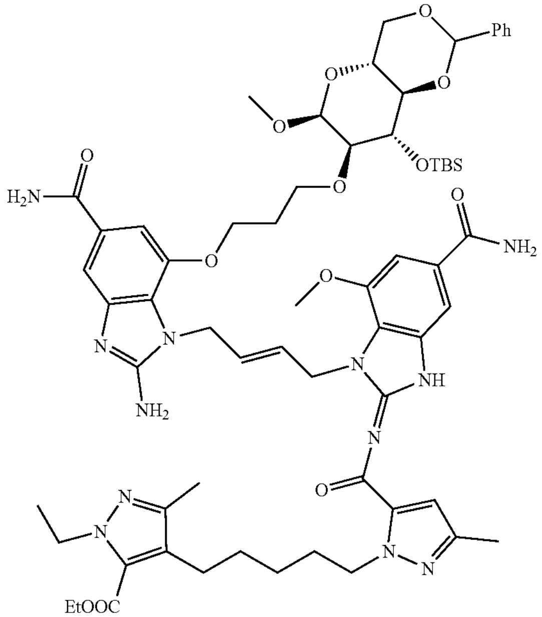

5-14

Compound 5-13 (445 mg, 0.36 mmol) was dissolved in methanol (15 mL), cyanogen bromide (38.7 mg, 0.36 mmol) was added, and the reaction system was stirred at room temperature for 16 h and concentrated under reduced pressure to remove the solvent to obtain a crude product 5-14.

MS (ESI) m/z $(M+H)^+$=1245.8.

Step 13: Preparation of Compound 5-15

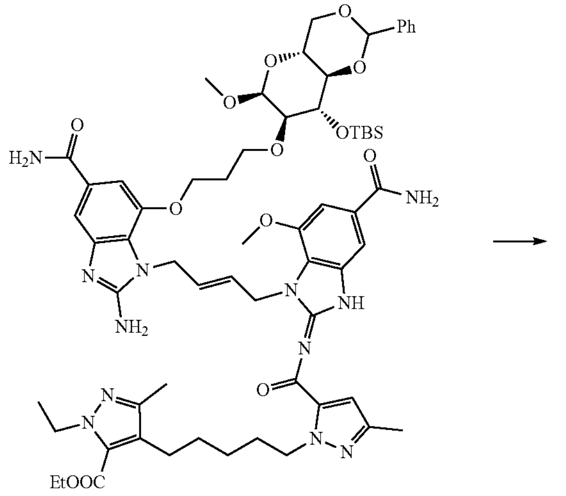

5-14

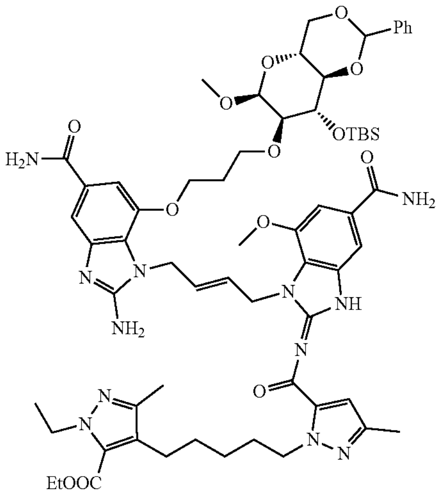

5-15

Compound 5-14 (339 mg, 0.27 mmol) was dissolved in methanol (6.0 mL), a sodium hydroxide solution (2.0 mL, 2.0 mol/L) was added, and the reaction system was stirred at room temperature for 16 h, added with dilute hydrochloric acid (1.0 mol/L) to adjust the pH to 5.0, and extracted with ethyl acetate (90 mL). The organic phase was washed with saturated saline (50 mL), dried over anhydrous sodium sulfate and filtered, and the filtrate was concentrated under reduced pressure to obtain a crude product 5-15.

MS (ESI) m/z $(M+H)^+$=1217.8.

Step 14: Preparation of Compound 5-16

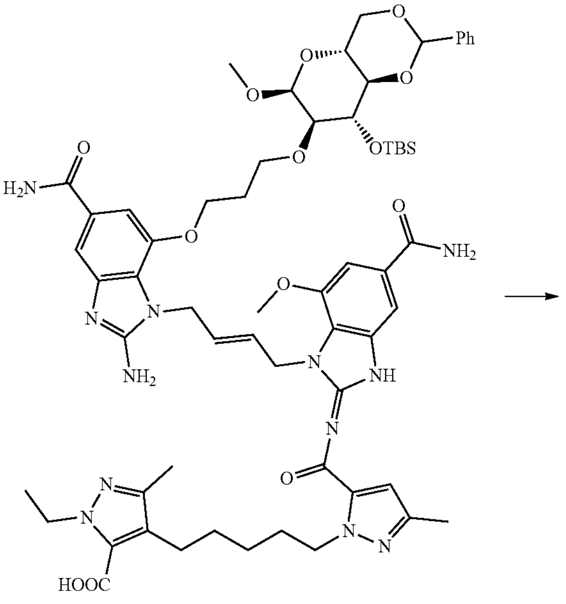

5-15

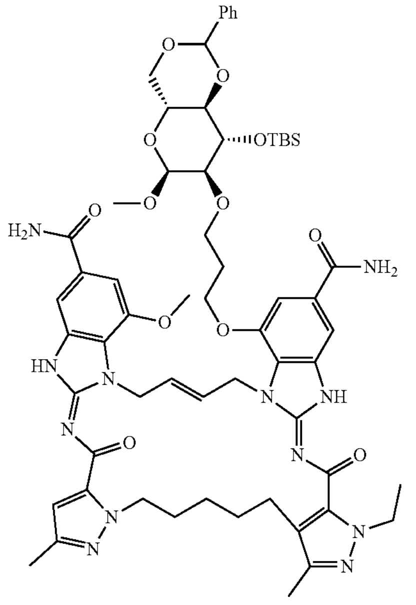

5-16

Compound 5-15 (307 mg, 0.25 mmol) was dissolved in N-methylpyrrolidinone (12 mL), and 1-(3-dimethylamino-propyl)-3-ethylcarbodiimide hydrochloride (72.2 mg, 0.38 mmol), 1-hydroxybenzotriazole (61.3 mg, 0.45 mol) and triethylamine (128 mg, 1.26 mmol) were serially added, the reaction system was stirred at room temperature for 24 h and concentrated under reduced pressure to remove the solvent, and the crude product was purified by flash silica gel column chromatography (dichloromethane/methanol (v/v)=1/0-9/1) to obtain compound 5-16.

MS (ESI) m/z (M+H)+=1200.2.

Step 15: Preparation of Compound 5

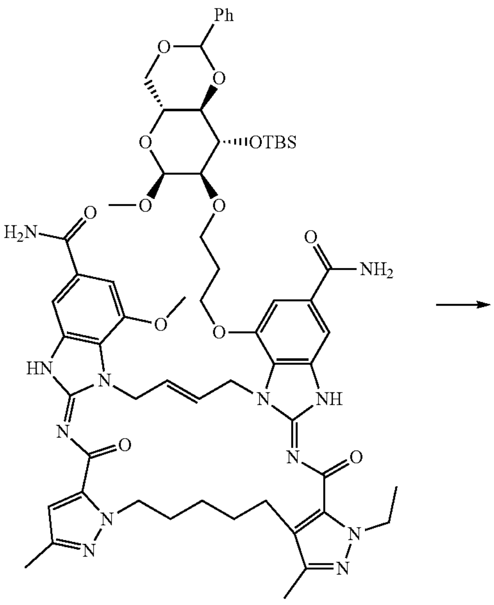

5-16

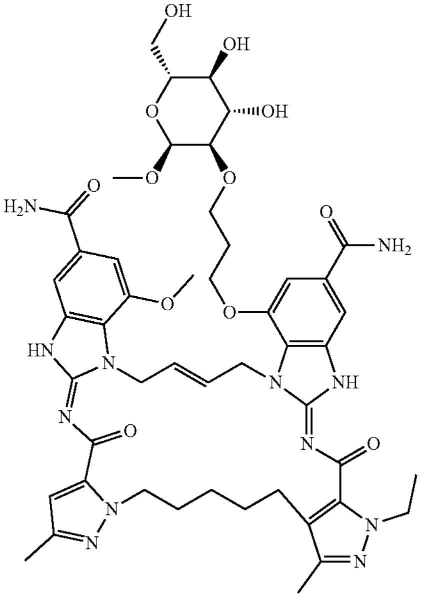

5

Compound 5-16 (207 mg, 0.17 mmol) was dissolved in dichloromethane (6 mL), trifluoroacetic acid (1.0 mL) was added, the reaction system was stirred at room temperature for 2 h and concentrated under reduced pressure to remove the solvent, and the crude product was purified by high performance liquid chromatography (separation condition: column: Ximate® C18 250 mm×21.2 mm, 10 μm; mobile phase: (water (10 mM ammonium bicarbonate)-acetonitrile); flow rate: 30 mL/min) to obtain compound 5 (HPLC retention time: 3.74 min).

HPLC analysis: column: Waters XBridge 4.6 mm×100 mm, 3.5 μm; mobile phase: (water (10 mM ammonium bicarbonate)-acetonitrile); B %: 5%-95%, 7 min;

MS (ESI) m/z $(M+H)^+$=996.8.

$^1$H NMR (400 MHz, DMSO-$d_6$) δ 12.89 (s, 2H), 7.99 (s, 2H), 7.66 (d, J=1.3 Hz, 2H), 7.45-7.24 (m, 4H), 6.50 (s, 1H), 5.68-5.66 (m, 2H), 4.96-4.81 (m, 6H), 4.64-4.63 (m, 3H), 4.46-4.42 (m, 3H), 3.99 (s, 2H), 3.48-3.41 (m, 3H), 3.17 (s, 3H), 3.08-2.95 (m, 2H), 2.71-2.69 (m, 2H), 2.16 (s, 3H), 2.08 (s, 3H), 1.76-1.74 (m, 6H), 1.49-1.47 (m, 4H), 1.33-1.27 (m, 6H).

Example 6: Preparation of Compound 6

Step 1: Preparation of Compound 6-1

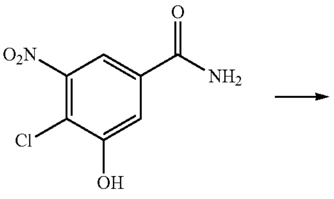

6-1

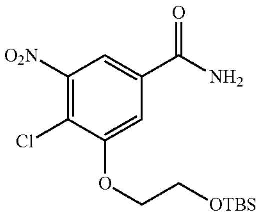

6-2

Compound 6-1 (2.9 g, 12.1 mmol) was dissolved in N,N-dimethylformamide (40 mL) under nitrogen atmosphere, (2-bromoethoxy)-tert-butyldimethylsilane (2 g, 9.2 mmol) and potassium carbonate (2.6 g, 18.5 mmol) were serially added, the reaction system was heated to 100° C. and stirred for 3 h, diluted with ethyl acetate (50 mL), washed with water (30 mL×3), dried over anhydrous sodium sulfate and filtered, the filtrate was concentrated under reduced pressure, and the crude product was purified by flash silica gel column chromatography (ethyl acetate/petroleum ether (v/v)=0/1-2/5) to obtain compound 6-2.

MS (ESI) m/z $(M+H)^+$=375.1.

Step 2: Preparation of Compound 6-3

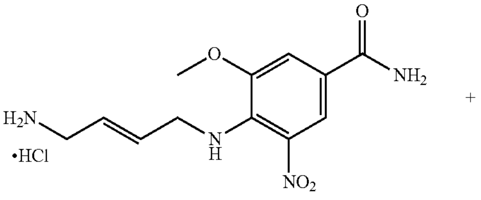

1-6

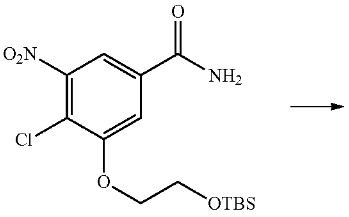

6-2

-continued

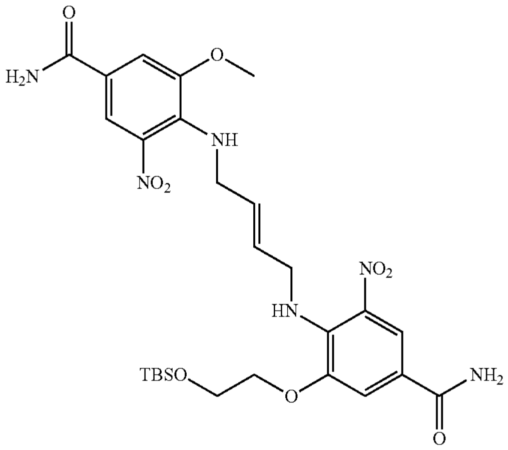

6-3

-continued

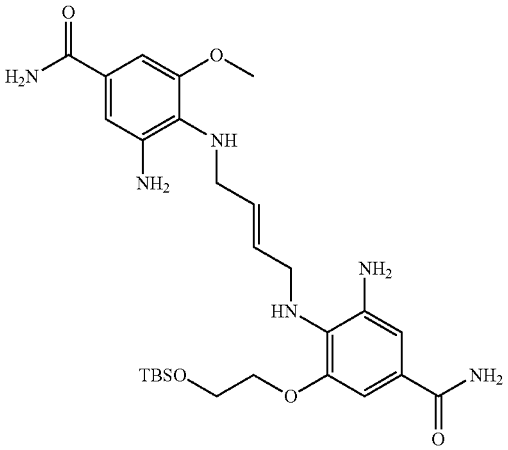

6-4

Compound 1-6 (1.5 g, 4.7 mmol) was dissolved in butanol (25 mL), sodium bicarbonate (1 g, 11.9 mmol), diisopropylethylamine (4.5 mL, 25.84 mmol) were added and stirred for 10 min, then compound 6-2 (2.3 g, 6.1 mmol) was added, and the reaction system was heated to 120° C. in a sealed tube and stirred for 48 h, then cooled to room temperature and filtered. The residue was washed with ethanol (3 mL), the crude product was stirred in ethyl acetate (10 mL) for 10 min and filtered, and the solid was washed with ethyl acetate (5 mL) and ethanol (2 mL) and dried under vacuum to obtain compound 6-3 which was used in the next step directly without further purification.

MS (ESI) m/z $(M+H)^+$=619.3.

Step 3: Preparation of Compound 6-4

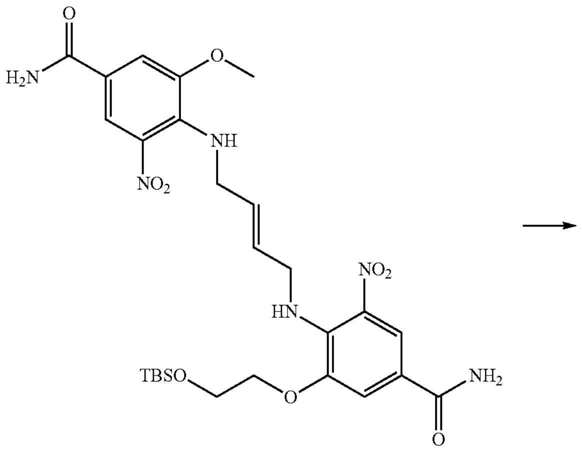

6-3

Compound 6-3 (1.93 g, 2.5 mmol) was dissolved in methanol (20 mL) and tetrahydrofuran (20 mL) at 0° C., an aqueous solution (10.0 mL) of sodium dithionite (4.3 g, 24.6 mmol) and 28% ammonia (8.5 mL, 61.6 mmol) were serially added, and the reaction system was stirred at room temperature for 20 min, added with water (100 mL) and extracted with ethyl acetate (50 mL×5). The organic phases were combined, washed with saturated brine (50 mL), dried over anhydrous sodium sulfate and filtered, and the filtrate was concentrated under reduced pressure to obtain a crude product 6-4 which was used in the next step directly without further purification.

MS (ESI) m/z $(M+H)^+$=559.4.

Step 4: Preparation of Compound 6-5

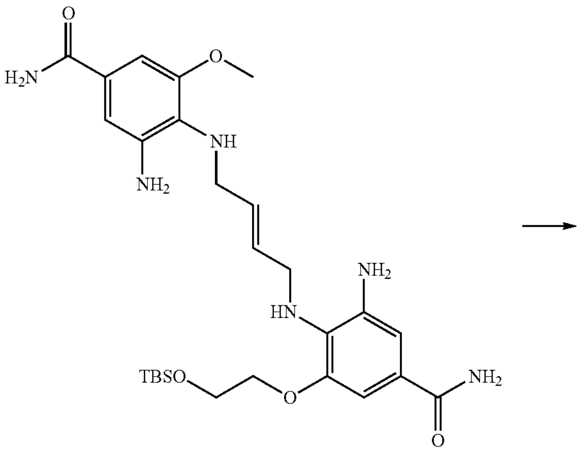

6-4

-continued

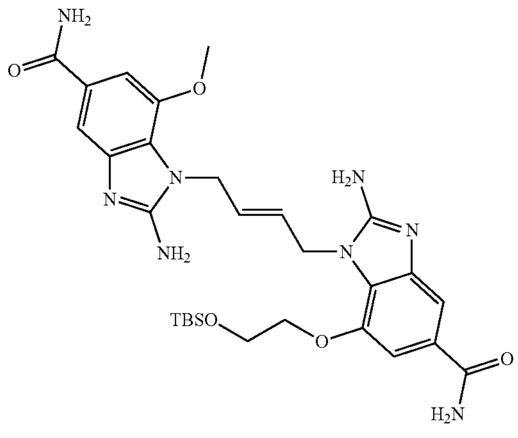

6-5

-continued

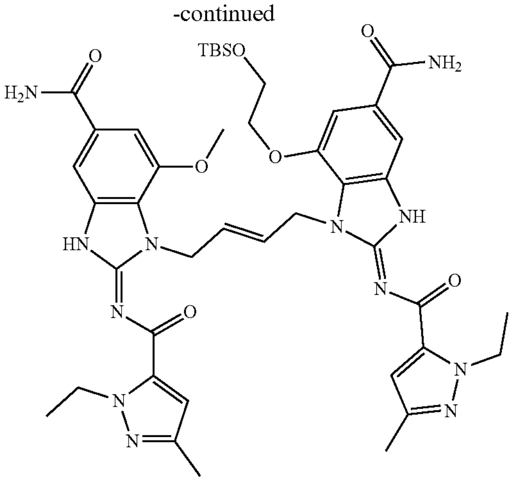

6-6

Compound 6-4 (1.9 g, 2.9 mmol) was dissolved in methanol (100 mL), cyanogen bromide (1.5 g, 14.2 mmol) was added, the reaction system was stirred at 15° C. for 2 h and filtered to collect the solid, and the solid was washed with methanol/ethyl acetate (v/v=1:1, 5 mL×4) to obtain a crude product 6-5 which was used in the next step directly without further purification.

MS (ESI) m/z $(M+H)^+$=609.4.

$^1$H NMR (400 MHz, DMSO-$d_6$) δ 8.72 (br s, 4H), 8.13 (br s, 2H), 7.56-7.51 (m, 2H), 7.44-7.34 (m, 4H), 5.98-5.69 (m, 2H), 5.03-4.81 (m, 4H), 4.17-4.08 (m, 2H), 3.82-3.71 (m, 5H), 0.84-0.76 (m, 9H), −0.01-0.08 (m, 6H).

Step 5: Preparation of Compound 6-6

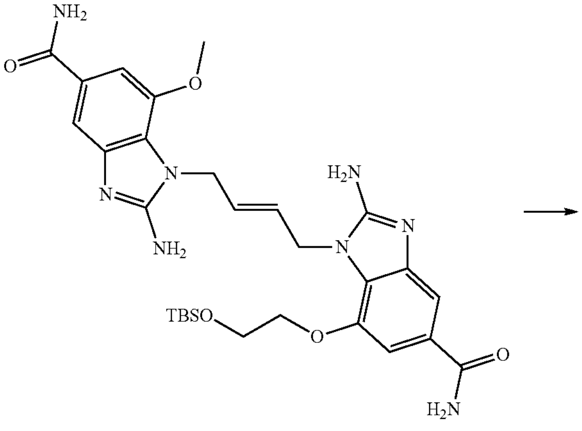

6-5

Compound 6-5 (1.1 g, 7.2 mmol) was dissolved in N,N-dimethylformamide (15 mL), triethylamine (1.2 mL, 8.9 mmol) and O-(7-azabenzotriazol-1-yl)-N,N,N',N'-tetramethyluronium hexafluorophosphate (2.8 g, 7.2 mmol) were added and stirred for 1 h, and 1-ethyl-3-methylpyrazole-5-carboxylic acid (1.25 g, 1.8 mmol) was added and then stirred for 12 h. The reaction was quenched by adding an aqueous sodium hydroxide solution (5 M, 10 mL, 50 mmol), and the reaction system was stirred for 3 h, concentrated under reduced pressure to remove the solvent, added with ethyl acetate (50 mL) and water (50 mL), and filtered to remove the solid. The organic phase was washed with water (15 mL×2), dried over anhydrous sodium sulfate and filtered, the filtrate was concentrated under reduced pressure, and the crude product was purified by flash silica gel column chromatography (dichloromethane/methanol (v/v)=1/0-5/1) to obtain compound 6-6.

MS (ESI) m/z $(M+H)^+$=881.4.

Step 6: Preparation of Compound 6-7

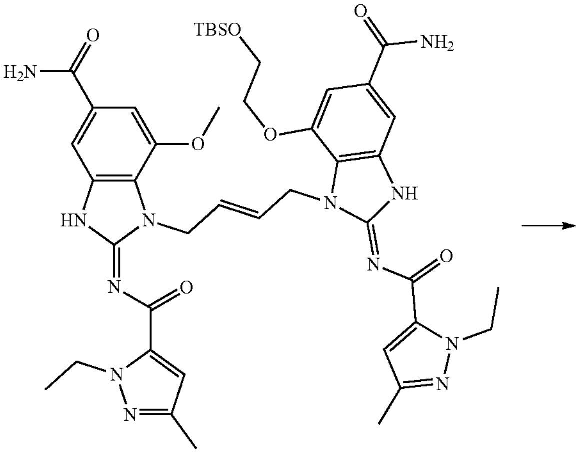

6-6

-continued

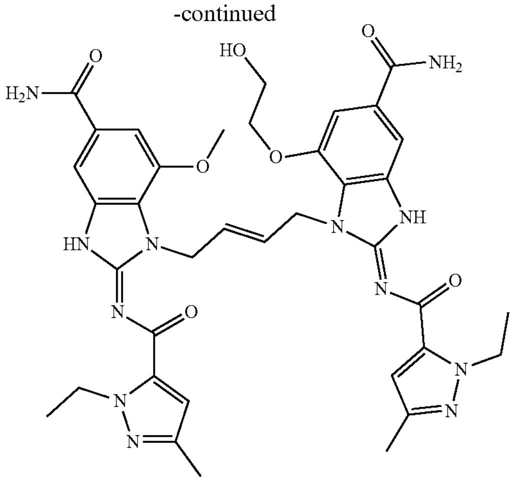

6-7

-continued

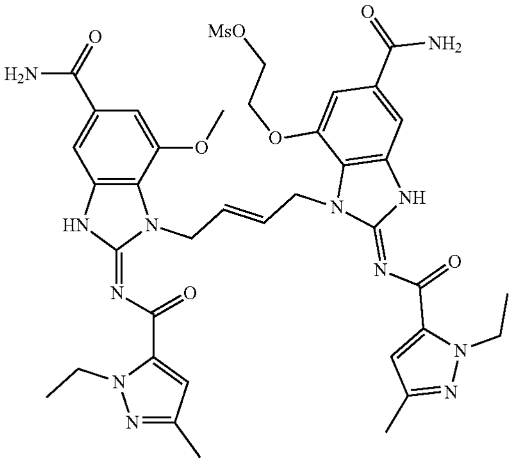

6-8

Compound 6-6 (0.4 g, 454 μmol) was dissolved in tetrahydrofuran (3 mL), tetrabutylammonium fluoride (1 M in tetrahydrofuran, 1.6 mL, 1.6 mmol) and acetic acid (0.1 mL, 1.8 mmol) were added, the reaction system was stirred at 15° C. for 18 h and filtered to collect the solid, and the solid was washed with ethyl acetate (3 mL×3) to obtain a crude product 6-7 which was used in the next step directly without further purification.

MS (ESI) m/z $(M+H)^+$=767.3.

Step 7: Preparation of Compound 6-8

Compound 6-7 (265 mg, 345.6 μmol) was dissolved in N,N-dimethylformamide (15 mL) and tetrahydrofuran (15 mL), triethylamine (150 uL, 1.1 mmol) was added and then the reaction system was stirred for 10 min, then methanesulfonyl chloride (80 uL, 1.0 mmol) was added, and the reaction system was stirred at 15° C. for 2 h. The reaction was quenched by adding water (80 mL), and the system was extracted with dichloromethane/methanol (v/v=10:1, 30 mL×4). The organic phases were combined, dried over anhydrous sodium sulfate and filtered, the filtrate was concentrated under reduced pressure, and the crude product was slurried and purified with acetonitrile/isopropyl ether (v/v=1/1, 6 mL) to obtain compound 6-8.

$^1H$ NMR (400 MHz, DMSO-$d_6$) δ 8.05-7.89 (m, 2H), 7.66 (d, J=17.4 Hz, 2H), 7.42-7.27 (m, 4H), 6.49 (d, J=16.6 Hz, 2H), 5.87-5.75 (m, 2H), 5.11-4.86 (m, 4H), 4.55-4.41 (m, 8H), 4.35-4.29 (m, 2H), 3.78-3.70 (m, 3H), 3.16 (s, 3H), 2.10-2.07 (m, 6H), 1.28-1.21 (m, 6H).

Step 8: Preparation of Compound 6-10

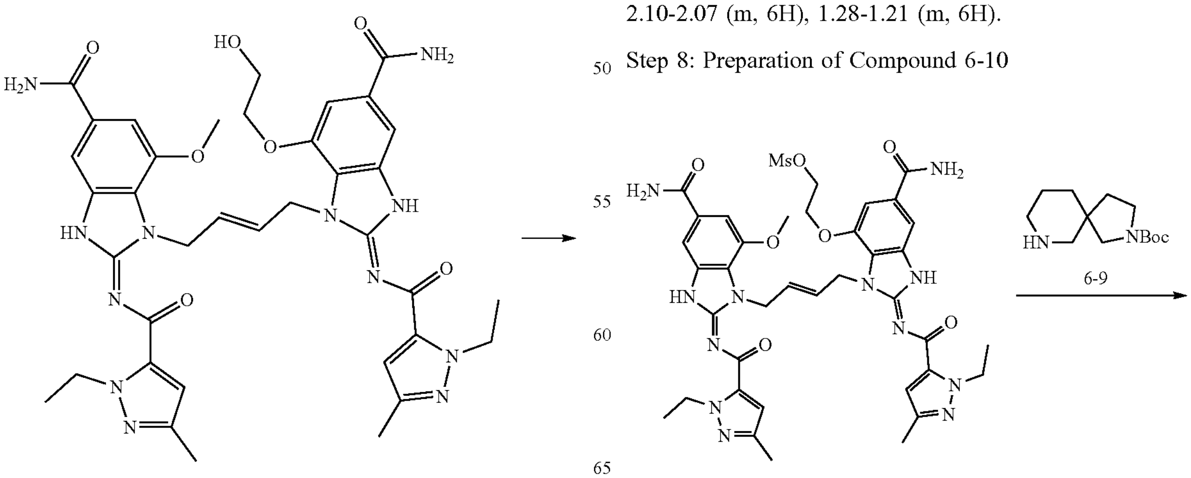

6-7 6-8

-continued

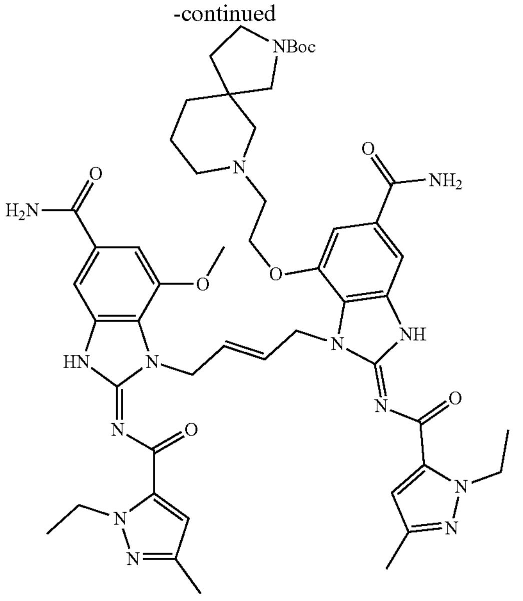

6-10

-continued

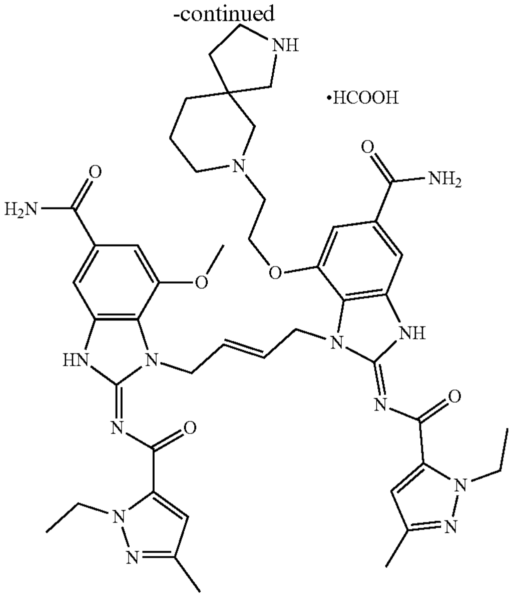

6

Compound 6-8 (110 mg, 130.2 μmol) was dissolved in acetonitrile (5 mL), potassium carbonate (84.6 mg, 612.2 μmol), potassium iodide (42.3 mg, 254.9 μmol) and compound 6-9 (143.9 mg, 598.5 μmol) were added, and the reaction system was stirred at 60° C. for 1 h, then stirred at 80° C. for 8 h, cooled to room temperature, added with ethyl acetate (30 mL) and water (30 mL) and separated. The aqueous phase was extracted with ethyl acetate (30 mL×3), the organic phases were combined, dried over anhydrous sodium sulfate and filtered, and the filtrate was concentrated under reduced pressure to obtain a crude product 6-10 which was used in the next step directly without further purification.

MS (ESI) m/z $(M+H)^+$=989.5.

Step 9: Preparation of Compound 6

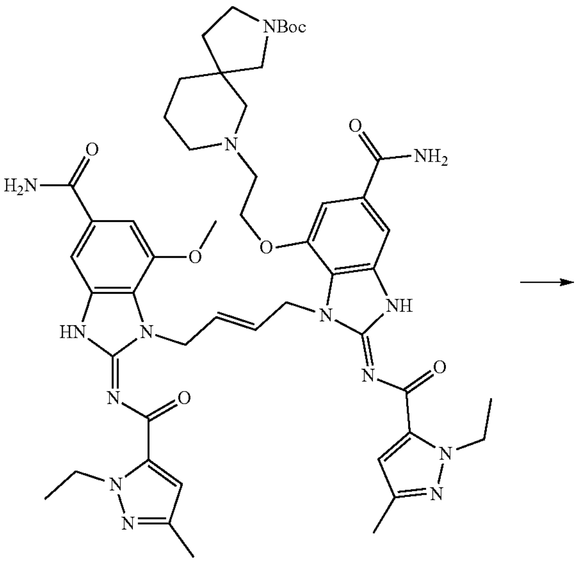

6-10

Compound 6-10 (0.2 g, 202.2 μmol) was dissolved in ethyl acetate (5 mL), a solution of hydrogen chloride in ethyl acetate (4 M, 8 mL, 32 mmol) was added, the reaction system was stirred at room temperature for 1.5 h, concentrated under reduced pressure to remove the solvent, and the crude product was purified by high performance liquid chromatography (separation condition: column: Xtimate® C18 150 mm×40 mm, 10 μm; mobile phase: (water (0.225% trifluoroacetic acid solution)-acetonitrile), B %: 10%-40%; flow rate: 30 mL/min) to obtain compound 5 (HPLC retention time: 8.22 min).

HPLC analysis: column: YMCpack-ODS AQ 150 mm×4.6 mm, 5 μm; mobile phase: (water (0.225% trifluoroacetic acid solution)-acetonitrile); B %: 5%-95%);

MS (ESI) m/z $(M+H)^+$=889.2.

$^1$H NMR (400 MHz, $CD_3OD$) δ 8.53 (s, 1H), 7.59 (s, 1H), 7.52 (s, 1H), 7.27 (s, 1H), 7.23 (s, 1H), 6.61 (s, 1H), 6.53 (s, 1H), 5.89-5.78 (m, 2H), 5.02-4.95 (m, 4H), 4.66-4.51 (m, 4H), 4.03-3.90 (m, 2H), 3.73 (s, 3H), 3.29-3.20 (m, 2H), 3.18-3.10 (m, 1H), 3.00 (d, J=12.0 Hz, 1H), 2.52-2.35 (m, 3H), 2.34-2.25 (m, 1H), 2.21 (s, 3H), 2.18 (s, 3H), 2.16-1.98 (m, 2H), 1.90-1.69 (m, 2H), 1.61-1.39 (m, 4H), 1.39-1.27 (m, 6H).

Example 6

Preparation of Compound 7

Step 1: Preparation of Compound 7-1

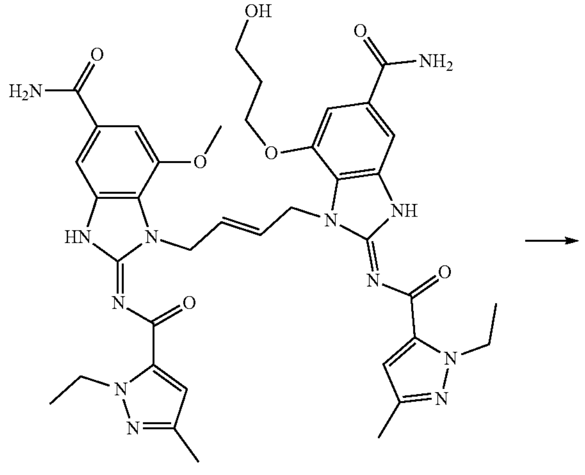

2-4

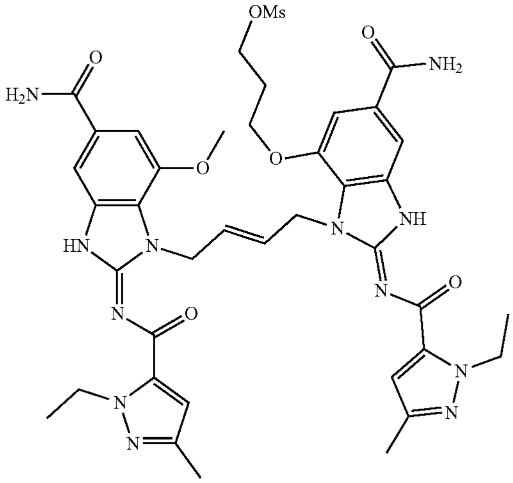

7-1

Compound 2-4 (100 mg, 128.07 μmol) was dissolved in tetrahydrofuran (15 mL), triethylamine (155 mg, 1.54 mmol, 214 uL) and methanesulfonyl chloride (147 mg, 1.28 mmol, 99 uL) were added, and the reaction system was stirred at 15° C. for 1 h. The reaction was quenched by adding water (0.5 mL), and the system was concentrated under reduced pressure to remove the solvent. The residue was dissolved in water (10 mL) and extracted with dichloromethane/methanol (v/v=10:1, 50 mL×4), the organic phases were combined, dried over anhydrous sodium sulfate and filtered, the filtrate was concentrated under reduced pressure, and the crude product was slurried and purified with ethyl acetate (3 mL) to obtain compound 7-1.

MS (ESI) m/z $(M+H)^+$=859.4.

Step 2: Preparation of Compound 7-2

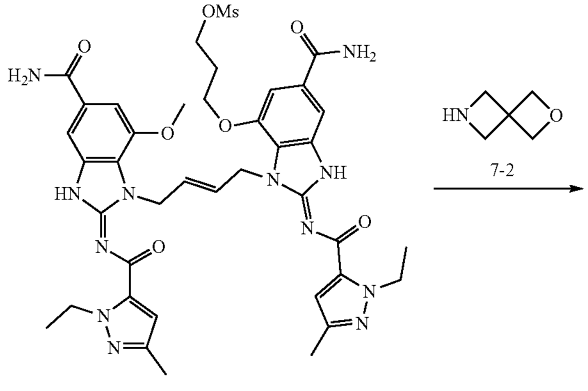

7-1

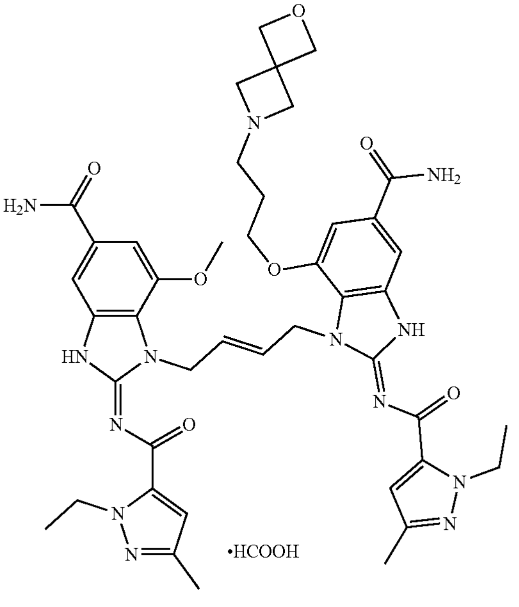

7

Compound 7-1 (60 mg, 69.86 μmol) was dissolved in acetonitrile (1 mL), compound 7-2 (80 mg, 419.13 μmol), potassium carbonate (77 mg, 558.84 μmol) and potassium iodide (1 mg, 6.99 μmol) were added, the reaction system was stirred at 50° C. for 1 h, then stirred at 60° C. for 2 h, cooled to room temperature and filtered to remove the solid, and the filtrate was diluted with water (30 mL) and extracted with ethyl acetate (50 mL×3) and dichloromethane/methanol (v/v=10:1, 50 mL×3). The organic phases were combined, dried over anhydrous sodium sulfate and filtered, the filtrate was concentrated under reduced pressure, and the crude product was purified by high performance liquid chromatography (separation condition: column: Boston Green ODS 150 mm×30 mm, 5 μm; mobile phase: (water (0.2% trifluoroacetic acid solution)-acetonitrile), B %: 18%-48%; flow rate: 35 mL/min) to obtain compound 5 (HPLC retention time: 7.00 min).

HPLC analysis: column: YMCpack-ODS AQ 150 mm×4.6 mm, 5 μm; mobile phase: (water (0.225% trifluoroacetic acid solution)-acetonitrile); B %: 5%-95%);

MS (ESI) m/z $(M+H)^+$=781.3.

$^1H$ NMR (400 MHz, $CD_3OD-d_4$) δ 8.46 (s, 1H), 7.59 (s, 1H), 7.56 (s, 1H), 7.27 (s, 1H), 7.20 (s, 1H), 6.61 (s, 1H), 6.56 (s, 1H), 5.81 (s, 2H), 4.99 (s, 4H), 4.68 (s, 4H), 4.66-4.54 (m, 4H), 3.96-3.80 (m, 2H), 3.71 (s, 3H), 3.46 (s, 4H), 2.63-2.48 (m, 2H), 2.21 (s, 3H), 2.19 (s, 3H), 1.64-1.49 (m, 2H), 1.41-1.23 (m, 6H).

Experimental Example 1

STING In Vitro Binding Assay

Fluorescence polarization assay (FP assay) was used to detect the affinities of compounds to a human STING protein. The reaction system contained a certain amount of fluorescein labeled C-di-GMP and compounds to be detected with different concentrations, and when the C-terminal protein of the recombinant human STING was added, the two small molecules were competitively bound with the protein. The bound fluorescein-labeled c-di-GMP rotated slowly in the liquid phase, and at this point, the degree of fluorescence polarization detected was also high. The fluorescence polarization degree was in inverse relation with the concentrations and the affinities of the compounds to be detected. By detecting the magnitude of the polarized light in the reaction system, the affinities of the compounds to be detected to human STING could be accurately known.

The soluble human STING protein sequence used in the experiment was cut from the C-terminal part of the human wild-type endoplasmic reticulum binding protein STING, from the $140^{th}$ amino acid to the $379^{th}$ amino acid. There are several alleles with sequence differences of the human STING protein, and different alleles differ in affinities to CDN (Yi, et. al., "Single Nucleotide Polymorphisms of Human STING can affect innate immune response to cyclic dinucleotides" PLOS ONE, 2013, 8(10), e77846). The wild-type STING sequences (G230, 8232, 8293) account for about 57.9% of the total. The N-terminal of the recombinant STING protein was a 6His-SUMO sequence to facilitate correct protein folding and purification, and after protease cleavage, the C-terminal STING was used for FP assay.

In FP assay, a 384-well plate was used, with the fluorescein-labeled c-di-GMP with a final concentration of 30 nM, 10 μM human STING protein, and either reference compounds with different concentrations or the compounds to be detected added into 10 μL of the reaction system each well. The plate was centrifuged at 1000 g for 1 min, incubated at room temperature for 30 min in the dark and read with Envision.

The experimental results of the STING in vitro binding assay described above are shown in Table 1.

TABLE 1

| Compound No. | FP affinity assay $IC_{50}$ (μM) |
|---|---|
| ML RR-S2 CDA (ADU-S100) | 4.2 |
| Compound 1 | 0.4 |
| Compound 2 | 1.7 |
| Compound 3 | 3.7 |
| Compound 4 | 1.6 |
| Compound 5 | 1.5 |
| Compound 6 | 2.2 |
| Compound 7 | 3.8 |

Conclusion: in FP affinity assay, the compounds of the present disclosure showed a higher affinity to the human wild-type STING protein than endogenous 2'3'-cGAMP.

Experimental Example 2

THP-Dual In Vitro Binding Assay

The THP1-Dual™ cells used in the assay (InvivoGen, Catalog code: thpd-nfis) were constructed by stable integration of two inducible reporter genes in the human monocyte-like cell line THP1. The promoter sequence of the secretory embryo alkaline phosphatase (SEAP) reporter gene comprised an IFN-β basal promoter, 5 copies of NF-κB coexpression transcriptional response elements (NF-κB consensus transcriptional response elements) at the upstream and 3 copies of c-Rel binding sites. The secreted luciferase (Lucia) reporter gene was driven by 5 interferon-stimulated response elements (IFN-stimulated response elements) and a basal promoter of ISG54, thus making it possible to study two major downstream signaling pathways of STING simultaneously: the NF KB pathway was studied by assaying the SEAP activity; and the IRF pathway was studied by assessing the activity of Lucia luciferase.

To each well of a 96-well plate were added 20 μL of reference compounds or the compounds to be detected followed by the addition of 180 μL of THP1-Dual™ cell-containing FBS-free RPMI-1640 culture medium (about 90,000 cells/well). After incubating at 37° C. for 30 min under 5% $CO_2$, the plate was centrifuged at 1000 rpm for 10 min, the supernatant was discarded, and the plate was washed twice with RPMI-1640 at 200 μL/well, and incubated for 18 h with RPMI-1640 at 200 L/well. IF-α/β activity was quantified using QUANTI-Luc™ prepared and used according to the manufacturer's instructions.

The results of the THP-dual in vitro binding assay described above are shown in Table 2.

TABLE 2

| Compound No. | $EC_{50}$ (μM) |
|---|---|
| ML RR-S2 CDA (ADU-S100) | 18.2 |
| Compound 1 | 0.021 |
| Compound 2 | 0.008 |
| Compound 3 | 0.04 |
| Compound 4 | 0.52 |
| Compound 5 | 0.06 |
| Compound 6 | 2.10 |
| Compound 7 | 0.08 |

Conclusion: in the human monocyte-like cell line THP1, the compounds of the present disclosure showed strong beta interferon activation promoting capacity.

Experimental Example 3

Drug Efficacy Evaluation

The compound efficacy evaluation was carried out by a CT26 syngeneic mouse model in this experiment. 3E5 colon cancer cells CT26 (ATCC-CRL-2638) were inoculated subcutaneously into 6-8 week-old Balb/C mice (Shanghai Lingchang Biotechnology Co., Ltd.), and the mice were randomly divided grouped, 6 mice per group when the tumor volume reached 100 $mm^3$. Intratumoral administration was performed on day 1 after grouping. Compound 1 was administered at a dose of 1 μg per mouse, 0.1 μg per mouse and 0.01 μg per mouse, respectively, for each group. Tumor volume measurements were taken three times a week after the start of administration. The calculation formula for tumor volume was: $V=0.5a \times b^2$, with a and b representing the long and short diameters of the tumor, respectively. Each point is the mean and standard error of mean (SEM) of the tumor volume. Differences between control (saline) and administered groups were statistically analyzed using two-way ANOVA (statistical differences on day 15: Prism 8, ****p<0.0001).

Conclusion: compared with the control group, the tumor growth speed of the mice in the administrated groups showed significantly slowed down. The inhibition of tumor growth in mice by compound 1 appeared dose-dependent.

What is claimed is:

1. A compound of formula (IA), an optical isomer thereof or a pharmaceutically acceptable salt thereof,

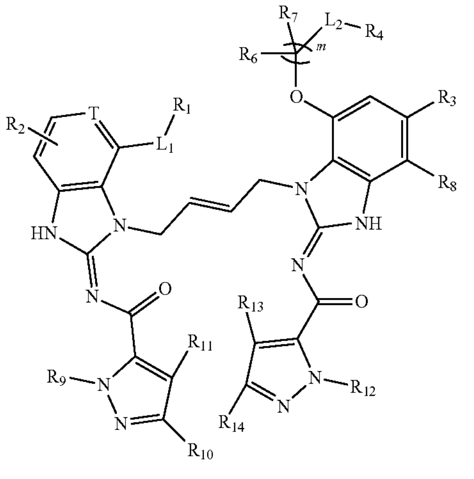

(IA)

wherein, $L_1$ is selected from the group consisting of —O—, —NH— and a single bond;

$R_1$ is selected from the group consisting of H and $C_{1-6}$ alkyl, wherein the $C_{1-6}$ alkyl is optionally substituted with 1, 2 or 3 R;

$R_2$ and $R_3$ are each independently selected from the group consisting of H,

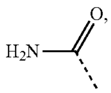 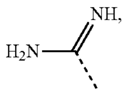

$C_{3-6}$ cycloalkyl, 5-6 membered heterocycloalkyl and 5-6 membered heteroaryl, wherein the $C_{3-6}$ cycloalkyl, 5-6 membered heterocycloalkyl or 5-6 membered heteroaryl is optionally substituted with 1, 2 or 3 R;

$L_2$ is selected from the group consisting of a single bond, —O—, —S—, —NH— and —NHC(=O)—;

$R_4$ is selected from the group consisting of

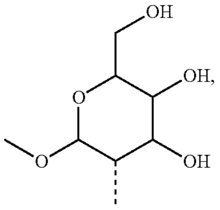 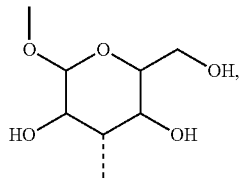

-continued

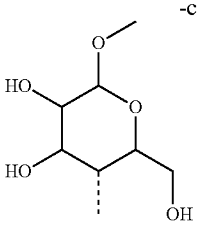 , 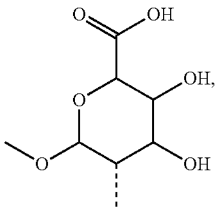

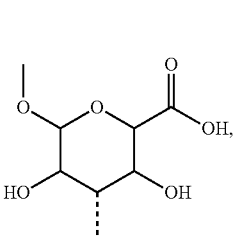 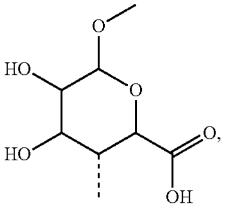

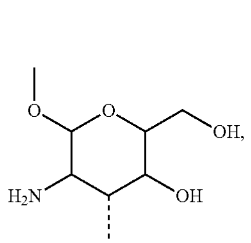 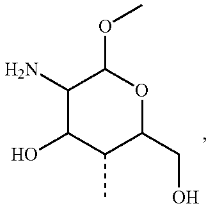 ,

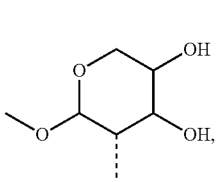 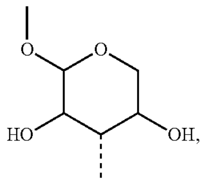

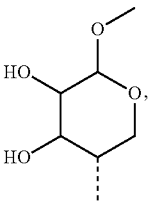 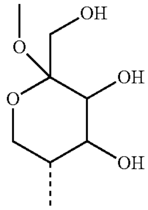 , 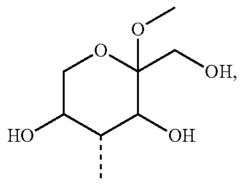

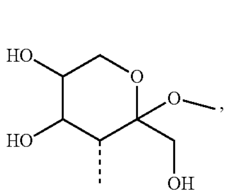 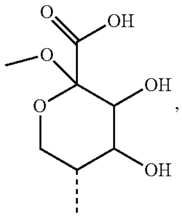 ,

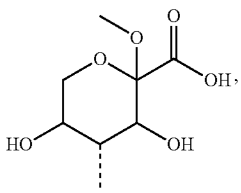 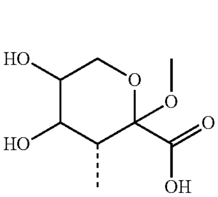 ,

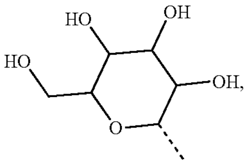 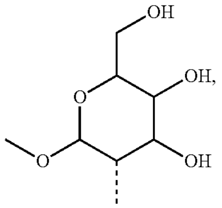

-continued

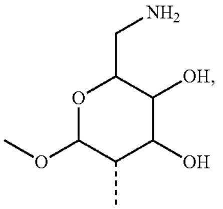 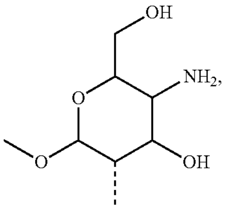

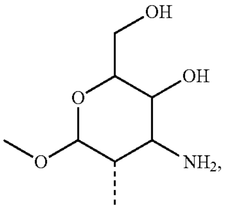 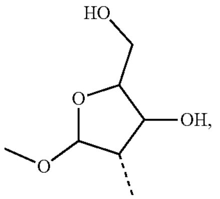

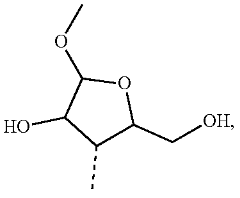 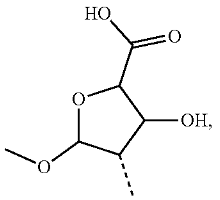

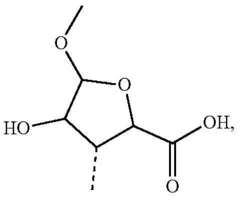 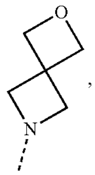 , 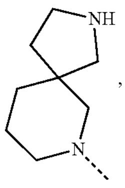 ,

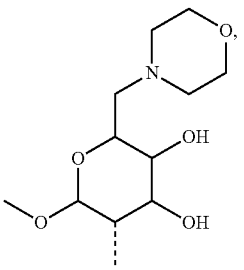

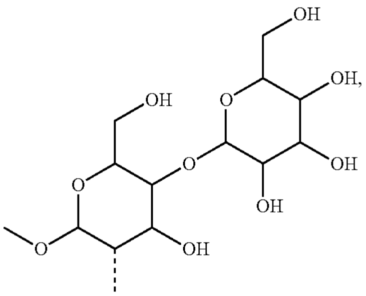 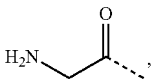

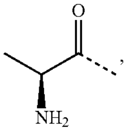 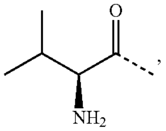 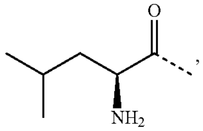

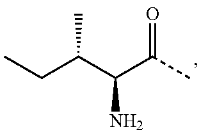 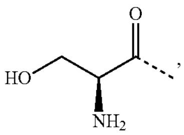 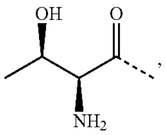

-continued

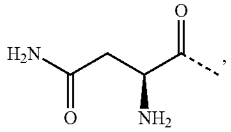 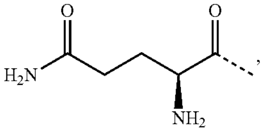

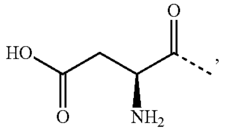 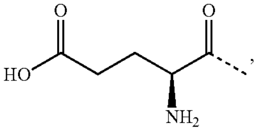

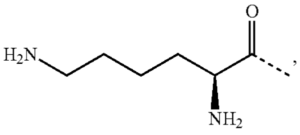 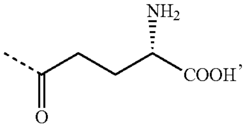

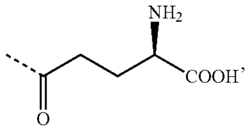 and 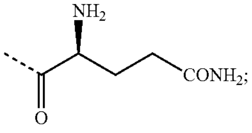

m is selected from the group consisting of 1, 2, 3, 4, 5 and 6;

$R_5$ is independently selected from the group consisting of OH, $NH_2$, $—CH_2NH_2$,

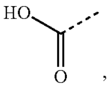 , 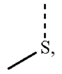 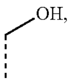 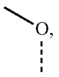

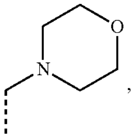 , and 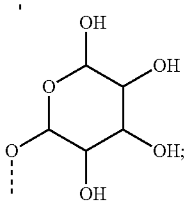

$R_6$ and $R_7$ are included in each instance of repeating unit of variable m, and in each instance, $R_6$ and $R_7$ are each independently selected from the group consisting of H, halogen, $N_3$, OH, SH, $NH_2$, CN,

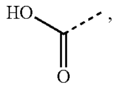

$C_{1-6}$ alkyl, $C_{1-6}$ alkoxy, $C_{1-6}$ alkylthio and $C_{1-6}$ alkylamino, wherein the $C_{1-6}$ alkyl, $C_{1-6}$ alkoxy, $C_{1-6}$ alkylthio or $C_{1-6}$ alkylamino is optionally substituted with 1, 2 or 3 R;

$R_8$ is selected from the group consisting of H, halogen, $N_3$, OH, SH, $NH_2$, CN,

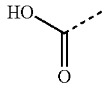

and $C_{1-6}$ alkyl, wherein the $C_{1-6}$ alkyl is optionally substituted with 1, 2 or 3 R;

or, $R_3$ and $R_8$ are linked to form a 5-6 membered heterocyclic ring;

$R_9$ and $R_{12}$ are each independently selected from the group consisting of H and $C_{1-6}$ alkyl, wherein the $C_{1-6}$ alkyl is optionally substituted with 1, 2 or 3 R;

$R_{10}$, $R_{11}$, $R_{13}$ and $R_{14}$ are each independently selected from the group consisting of H, halogen, $N_3$, OH, SH, $NH_2$, CN and $C_{1-6}$ alkyl, wherein the $C_{1-6}$ alkyl is optionally substituted with 1, 2 or 3 R;

or, $R_9$ and $R_{13}$ are linked to form a carbon chain comprising 3-7 carbon atoms;

T is selected from the group consisting of N and CH;

R is independently selected from the group consisting of H, halogen, $N_3$, OH, SH, $NH_2$, CN,

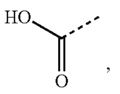,
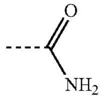,
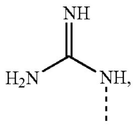

$C_{1-6}$ alkyl, $C_{1-6}$ alkoxy, $C_{1-6}$ alkylthio, $C_{1-6}$ alkylamino, 5-6 membered heterocycloalkyl, phenyl and 5-10 membered heteroaryl, wherein the $C_{1-6}$ alkyl, $C_{1-6}$ alkoxy, $C_{1-6}$ alkylthio, $C_{1-6}$ alkylamino, 5-6 membered heterocycloalkyl, phenyl or 5-10 membered heteroaryl is optionally substituted with 1, 2 or 3 R';

R' is selected from the group consisting of H, F, Cl, Br, I, OH, $NH_2$ and $CH_3$;

the 5-6 membered heterocycloalkyl, 5-6 membered heteroaryl, 4-10 membered heterocycloalkyl or 5-10 membered heteroaryl contains 1, 2 or 3 heteroatoms or heteroatom groups independently selected from the group consisting of —O—, —NH—, —S— and N.

2. The compound, the optical isomer thereof or the pharmaceutically acceptable salt thereof according to claim 1, selected from:

(IB)

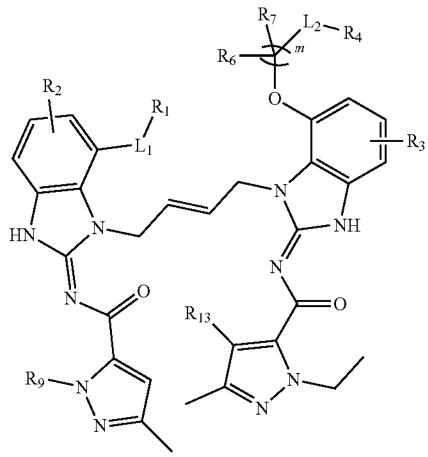

wherein, $L_1$ is selected from the group consisting of —O—, —NH— and a single bond;

$R_1$ is selected from the group consisting of H and $C_{1-6}$ alkyl, wherein the $C_{1-6}$ alkyl is optionally substituted with 1, 2 or 3 R;

$R_2$ and $R_3$ are each independently selected from the group consisting of H,

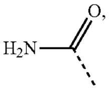
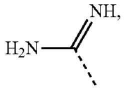

$C_{3-6}$ cycloalkyl, 5-6 membered heterocycloalkyl and 5-6 membered heteroaryl, wherein the $C_{3-6}$ cycloalkyl, 5-6 membered heterocycloalkyl or 5-6 membered heteroaryl is optionally substituted with 1, 2 or 3 R;

$L_2$ is selected from the group consisting of a single bond, —O—, —S—, —NH— and —NHC(=O)—;

$R_4$ is selected from the group consisting of

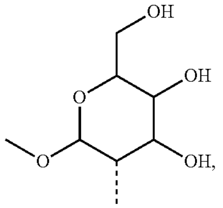
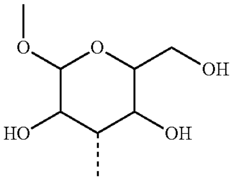,
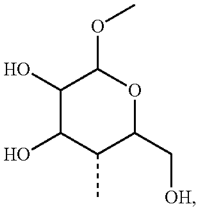
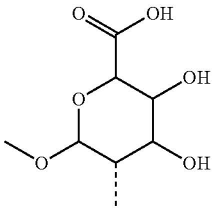,
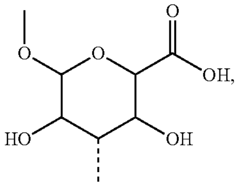
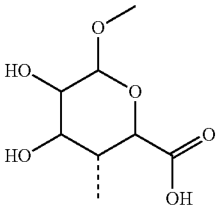,
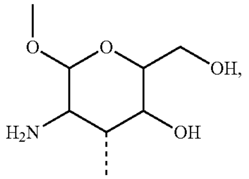
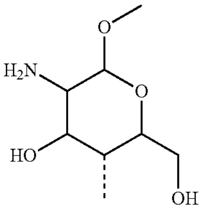,
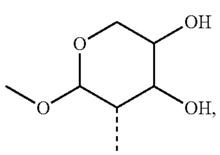
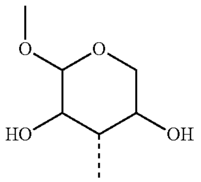,
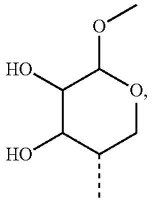
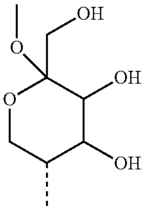, -continued
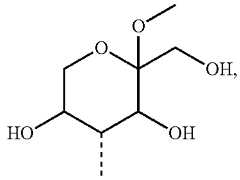
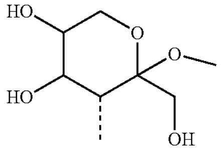
,
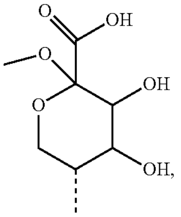
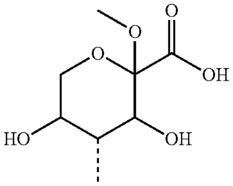
,
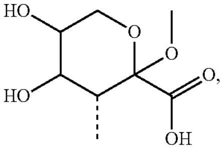
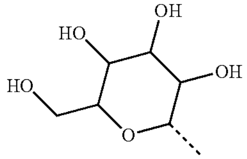
,
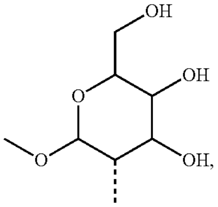
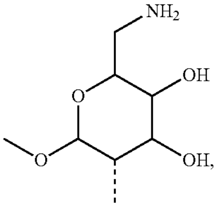
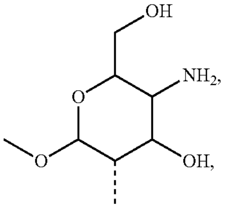
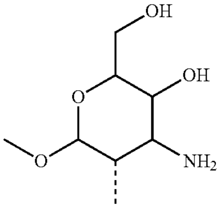
,
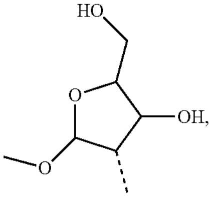
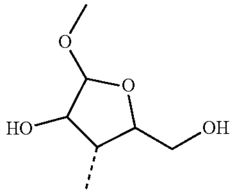
,
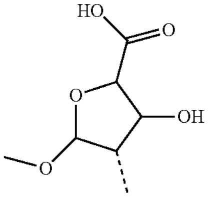
,
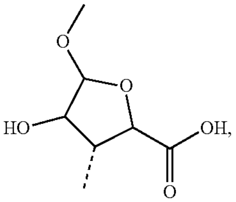
-continued
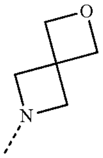
,
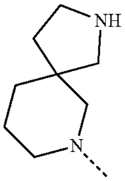
,
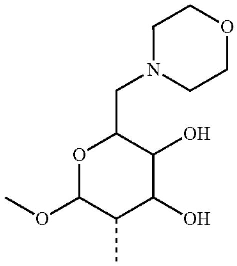
,
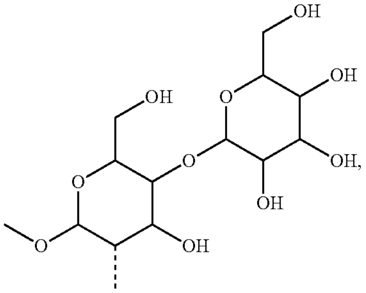
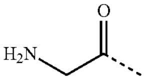
,
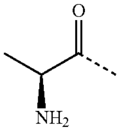
,
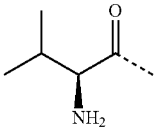
,
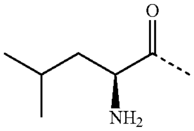
,
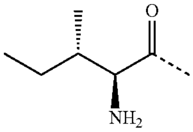
,
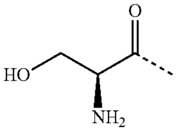
,
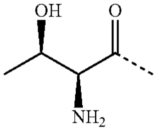
,
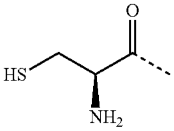
,
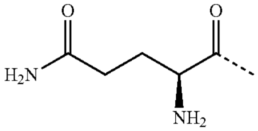
,
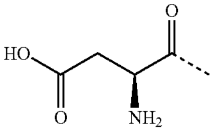
,
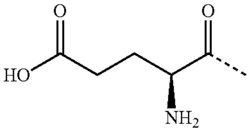
,
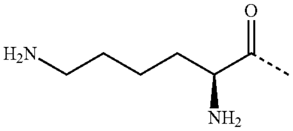
,
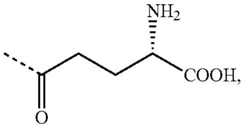

-continued

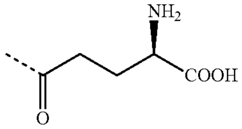 and 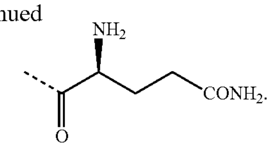

m is selected from the group consisting of 1, 2, 3, 4, 5 and 6;

$R_5$ is independently selected from the group consisting of OH, $NH_2$, —$CH_2NH_2$,

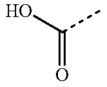,

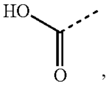, 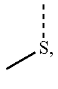 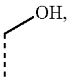 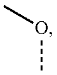

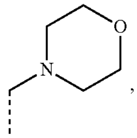, and 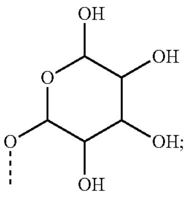

$R_6$ and $R_7$ are included in each instance of repeating unit of variable m, and in each instance, $R_6$ and $R_7$ are each independently selected from the group consisting of H, halogen, $N_3$, OH, SH, $NH_2$, CN,

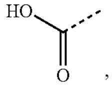, $C_{1-6}$ alkyl, $C_{1-6}$ alkoxy, $C_{1-6}$ alkylthio and $C_{1-6}$ alkylamino, wherein the $C_{1-6}$ alkyl, $C_{1-6}$ alkoxy, $C_{1-6}$ alkylthio or $C_{1-6}$ alkylamino is optionally substituted with 1, 2 or 3 R;

$R_9$ is independently selected from the group consisting of H and $C_{1-6}$ alkyl, wherein the $C_{1-6}$ alkyl is optionally substituted with 1, 2 or 3 R;

$R_{13}$ is independently selected from the group consisting of H, halogen, $N_3$, OH, SH, $NH_2$, CN and $C_{1-6}$ alkyl, wherein the $C_{1-6}$ alkyl is optionally substituted with 1, 2 or 3 R;

or, $R_9$ and $R_{13}$ are linked to form a carbon chain comprising 3-7 carbon atoms;

R is independently selected from the group consisting of H, halogen, $N_3$, OH, SH, $NH_2$, CN,

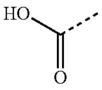, 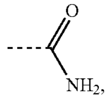 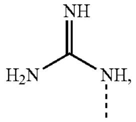

$C_{1-6}$ alkyl, $C_{1-6}$ alkoxy, $C_{1-6}$ alkylthio, $C_{1-6}$ alkylamino, 5-6 membered heterocycloalkyl, phenyl and 5-10 membered heteroaryl, wherein the $C_{1-6}$ alkyl, $C_{1-6}$ alkoxy, $C_{1-6}$ alkylthio, $C_{1-6}$ alkylamino, 5-6 membered heterocycloalkyl, phenyl or 5-10 membered heteroaryl is optionally substituted with 1, 2 or 3 R';

R' is selected from the group consisting of H, F, Cl, Br, I, OH, $NH_2$ and $CH_3$;

the 5-6 membered heterocycloalkyl, 5-6 membered heteroaryl, 5-10 membered heterocycloalkyl or 5-10 membered heteroaryl contains 1, 2 or 3 heteroatoms or heteroatom groups independently selected from the group consisting of —O—, —NH—, —S— and N.

3. The compound, the optical isomer thereof or the pharmaceutically acceptable salt thereof according to claim 1, wherein R is independently selected from the group consisting of H, halogen, $N_3$, OH, SH, $NH_2$, CN,

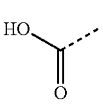, 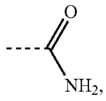 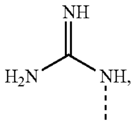

$C_{1-3}$ alkyl, $C_{1-3}$ alkoxy, $C_{1-3}$ alkylthio, $C_{1-3}$ alkylamino, morpholinyl, phenyl, imidazolyl and indolyl, wherein the $C_{1-3}$ alkyl, $C_{1-3}$ alkoxy, $C_{1-3}$ alkylthio, $C_{1-3}$ alkylamino, morpholinyl, phenyl, imidazolyl or indolyl is optionally substituted with 1, 2 or 3 R'.

4. The compound, the optical isomer thereof or the pharmaceutically acceptable salt thereof according to claim 3, wherein R is independently selected from the group consisting of H, F, Cl, Br, I, $N_3$, OH, SH, $NH_2$, CN, Me,

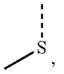 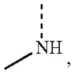 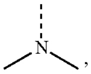 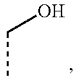, 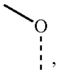 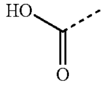,

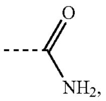 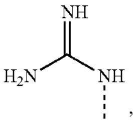, 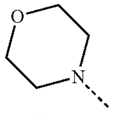 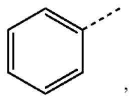,

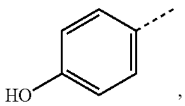, 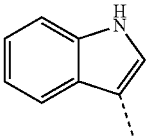 and 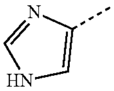.

5. The compound, the optical isomer thereof or the pharmaceutically acceptable salt thereof according to claim 1, wherein $R_1$ is selected from the group consisting of H, Me,

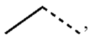 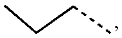 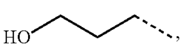 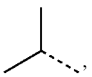

-continued

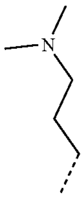 and 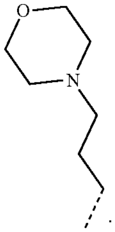 .

6. The compound, the optical isomer thereof or the pharmaceutically acceptable salt thereof according to claim 5, wherein the structural unit

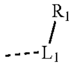

is selected from the group consisting of H,

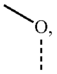 , 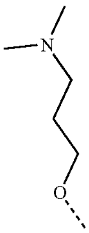 and 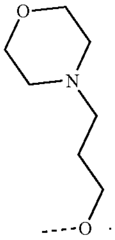 .

7. The compound, the optical isomer thereof or the pharmaceutically acceptable salt thereof according to claim 1, wherein R4 is selected from the group consisting of

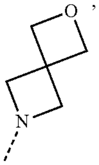 , 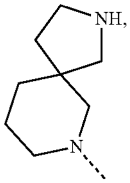 , and 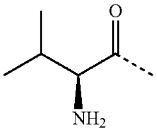 .

8. The compound, the optical isomer thereof or the pharmaceutically acceptable salt thereof according to claim 1, wherein R4 is selected from the group consisting of

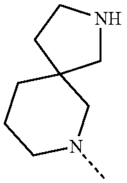 and 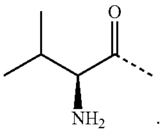 .

9. The compound, the optical isomer thereof or the pharmaceutically acceptable salt thereof according to claim 1, wherein $R_6$ and $R_7$ are included in each instance of repeating unit of variable m, and in each instance, $R_6$ and $R_7$ are each independently selected from the group consisting of H, halogen, $N_3$, OH, SH, $NH_2$, CN,

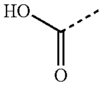 , $C_{1-3}$ alkyl, $C_{1-3}$ alkoxy, $C_{1-3}$ alkylthio and $C_{1-3}$ alkylamino, wherein the $C_{1-3}$ alkyl, $C_{1-3}$ alkoxy, $C_{1-3}$ alkylthio or $C_{1-3}$ alkylamino is optionally substituted with 1, 2 or 3 R.

10. The compound, the optical isomer thereof or the pharmaceutically acceptable salt thereof according to claim 9, wherein $R_6$ and $R_7$ are included in each instance of repeating unit of variable m, and in each instance, $R_6$ and $R_7$ are each independently selected from the group consisting of H, F, Cl, Br, I, $N_3$, OH, SH, $NH_2$, CN, Me,

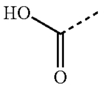 , 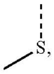 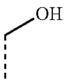 and 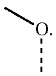

11. The compound, the optical isomer thereof or the pharmaceutically acceptable salt thereof according to claim 1, wherein the structural unit

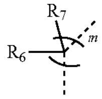

is selected from the group consisting of $—CH_2—$,

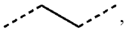 , 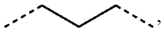 , 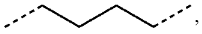 ,

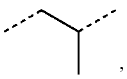 , 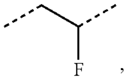 , 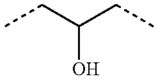 ,

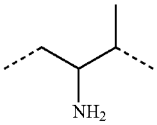 , 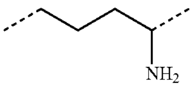 and

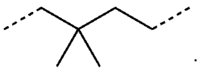 .

12. The compound, the optical isomer thereof or the pharmaceutically acceptable salt thereof according to claim 1, wherein the compound is selected from the group consisting of:
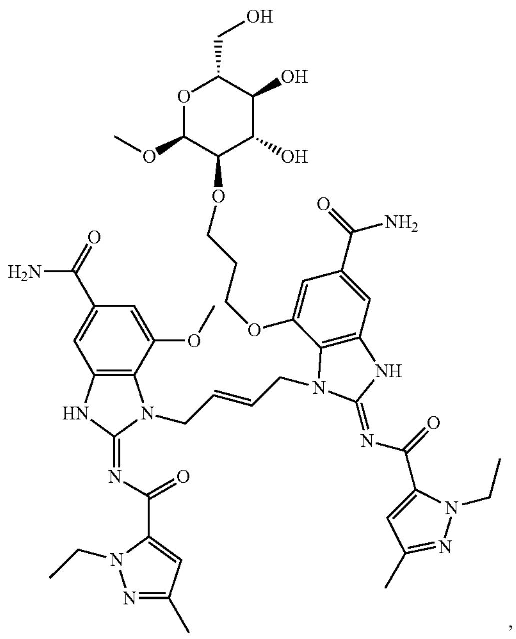
,
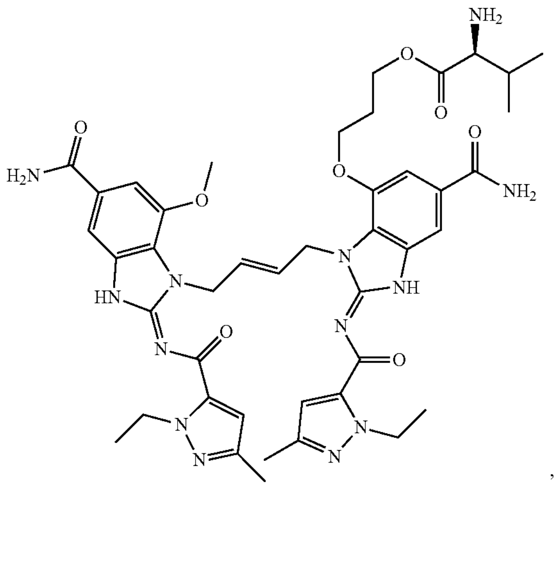
,
-continued
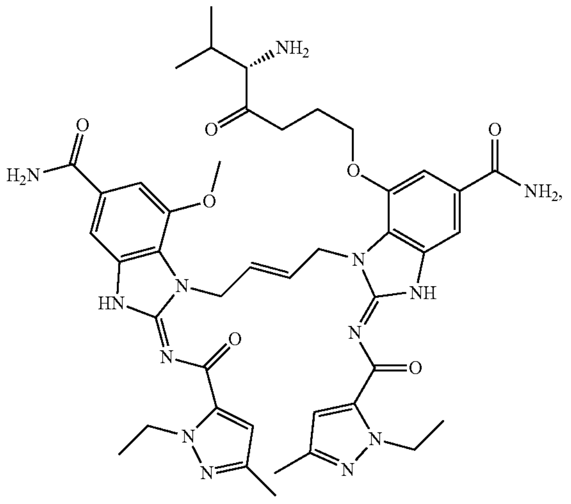
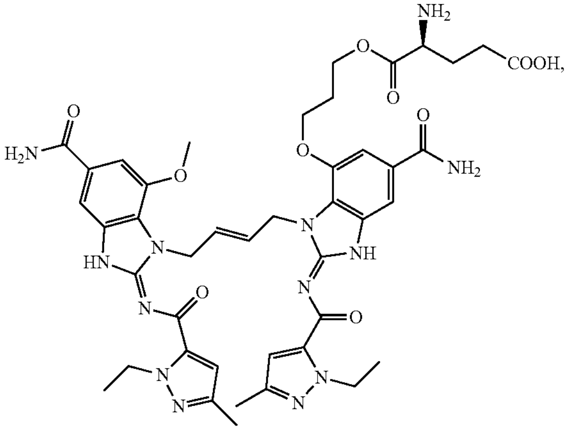
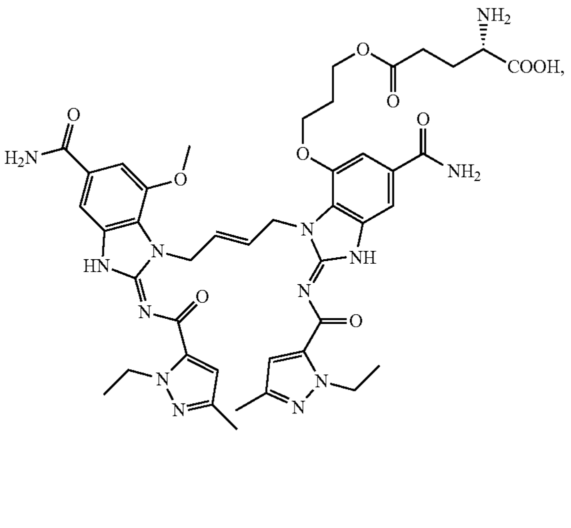

-continued
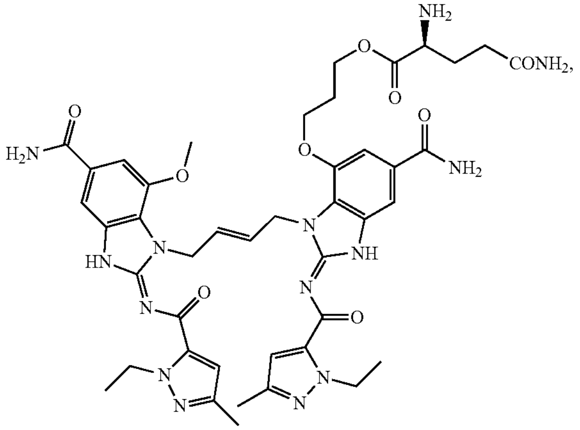
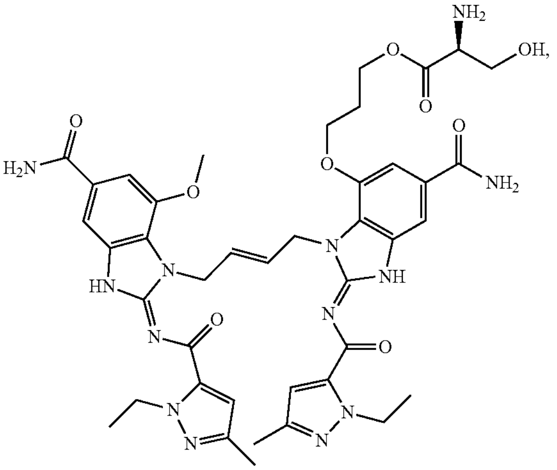
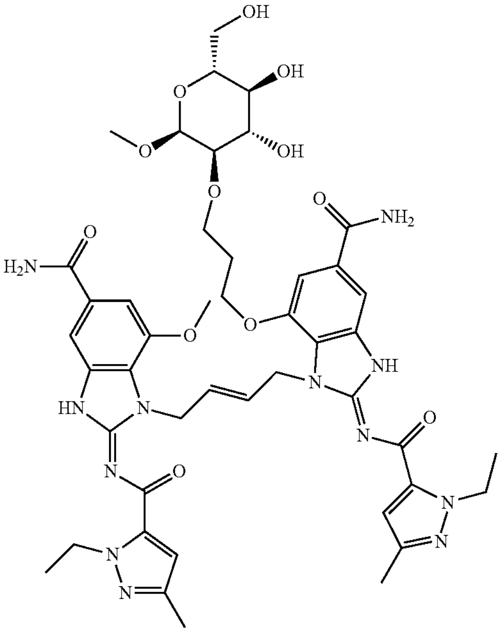
,
-continued
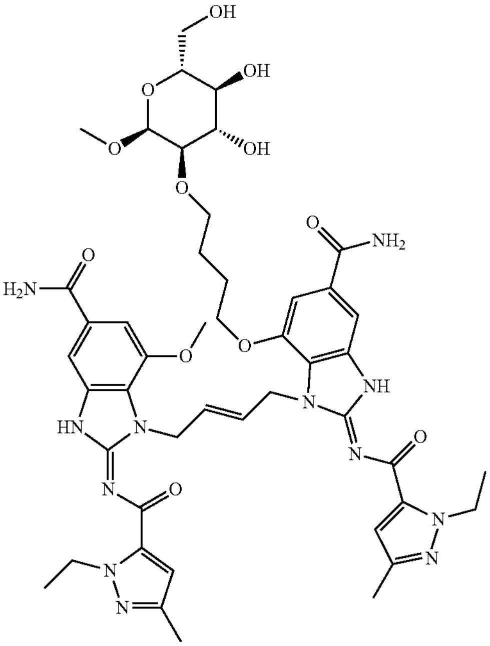
,
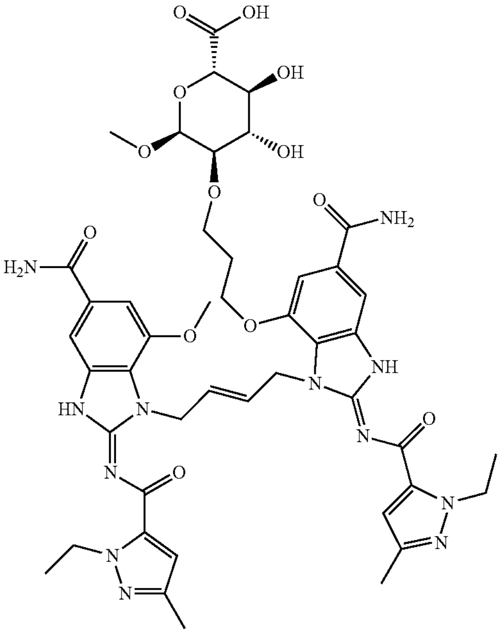
, -continued
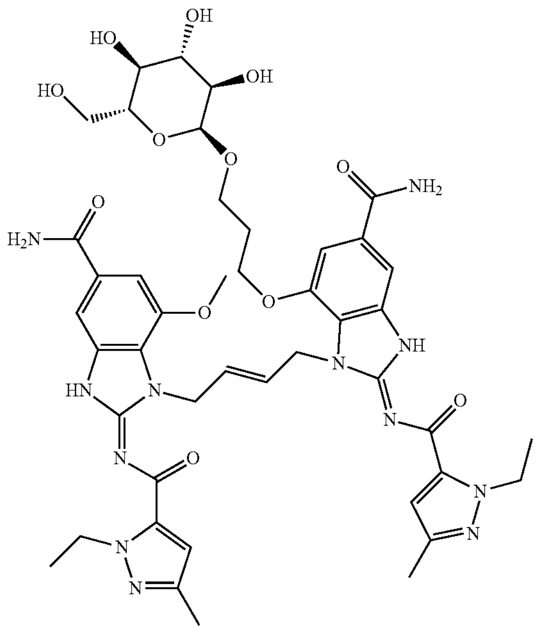
,
-continued
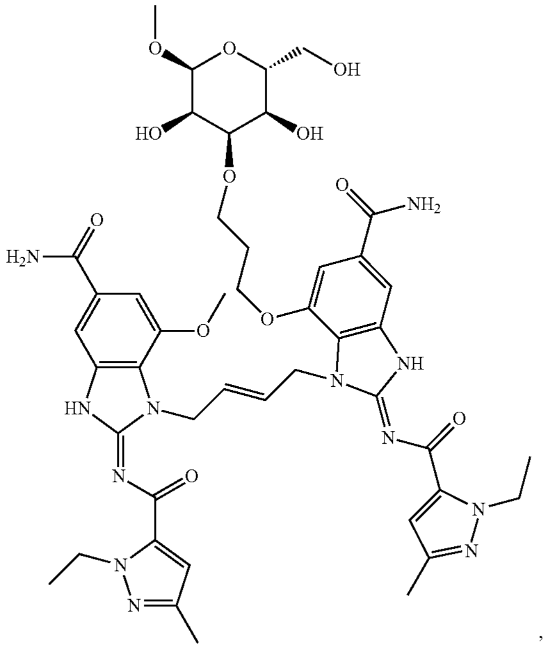
,
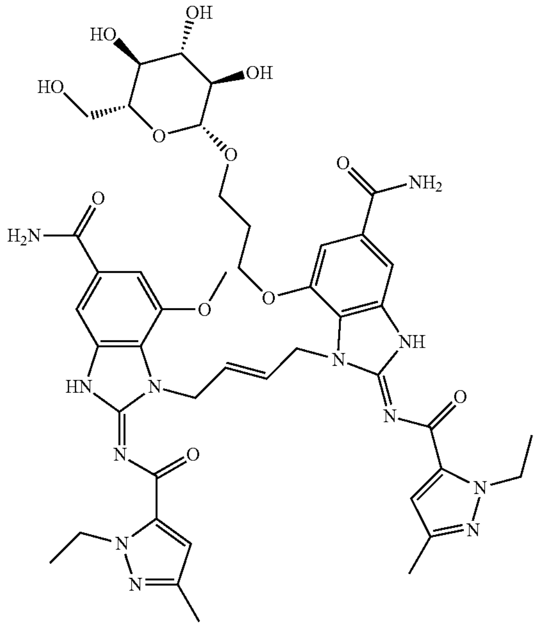
,
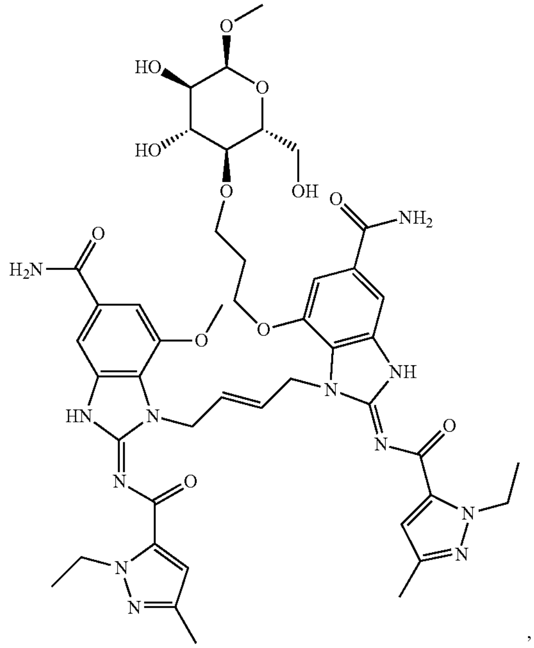
, -continued
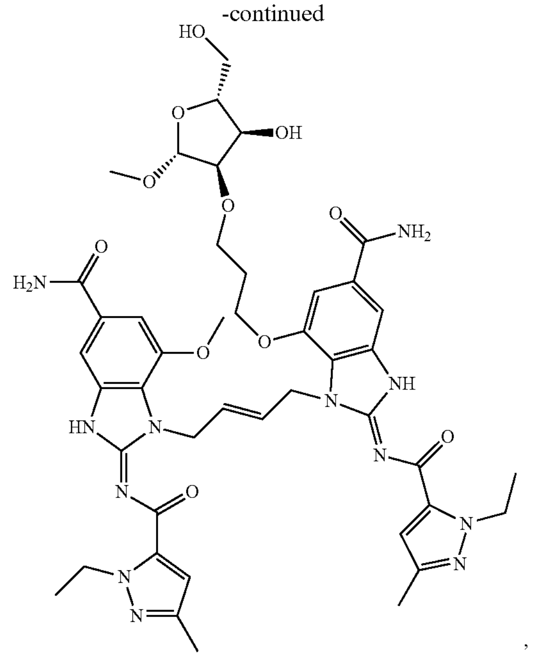
,
-continued
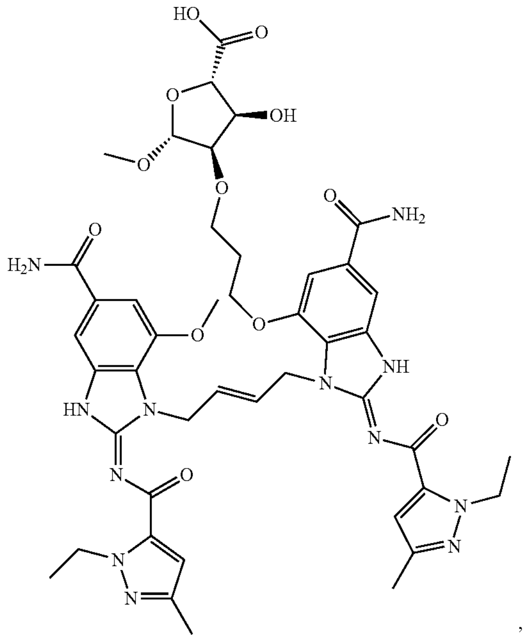
,
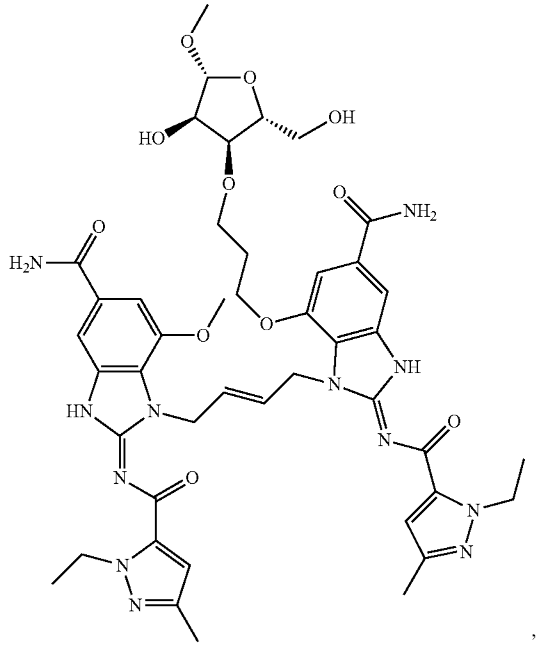
,
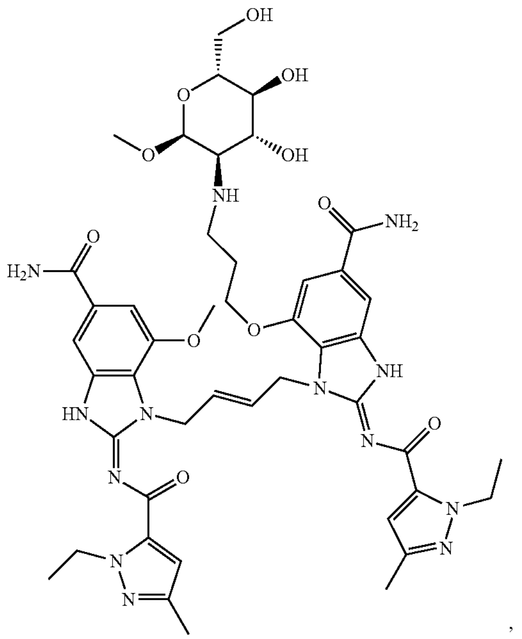
, -continued
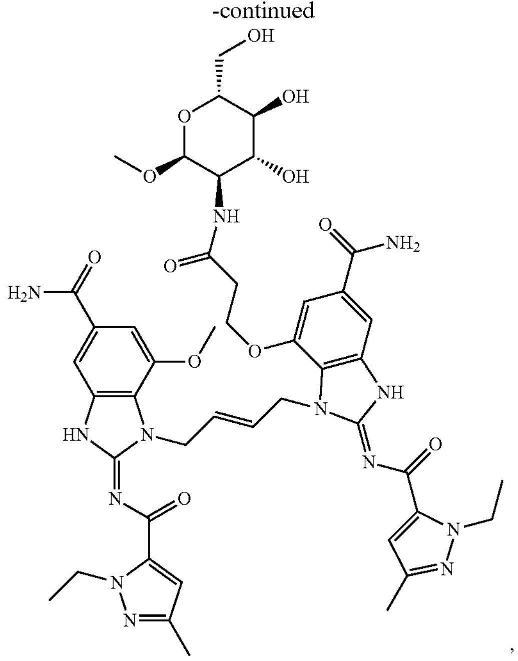
,
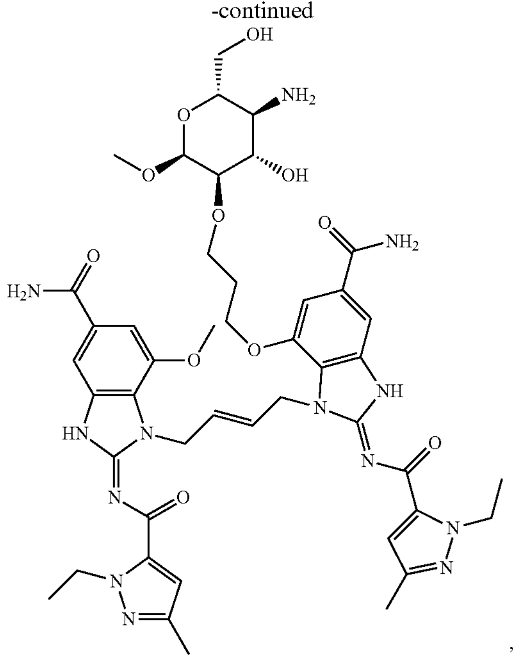
,
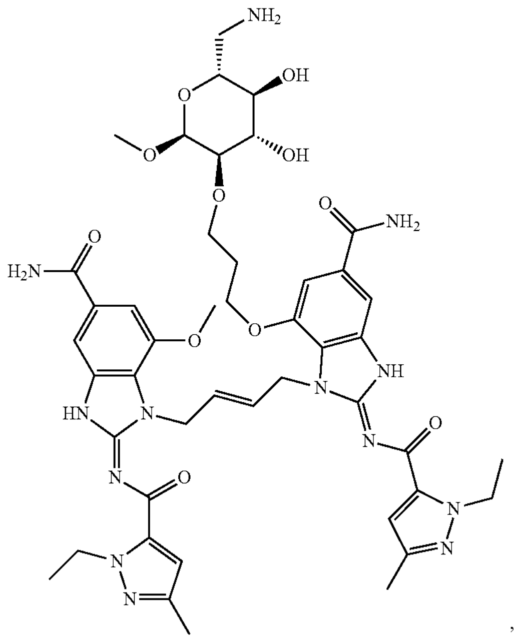
,
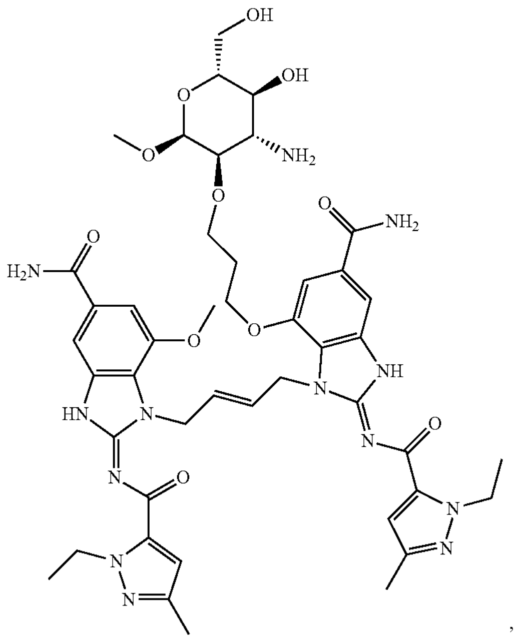
, -continued
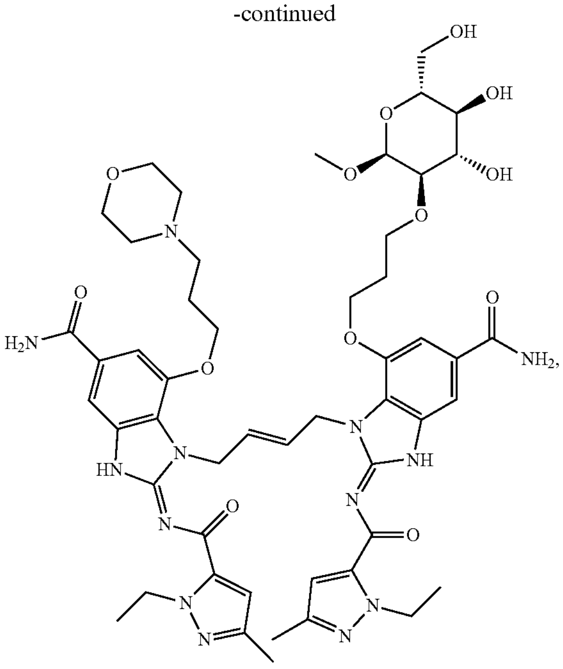
-continued
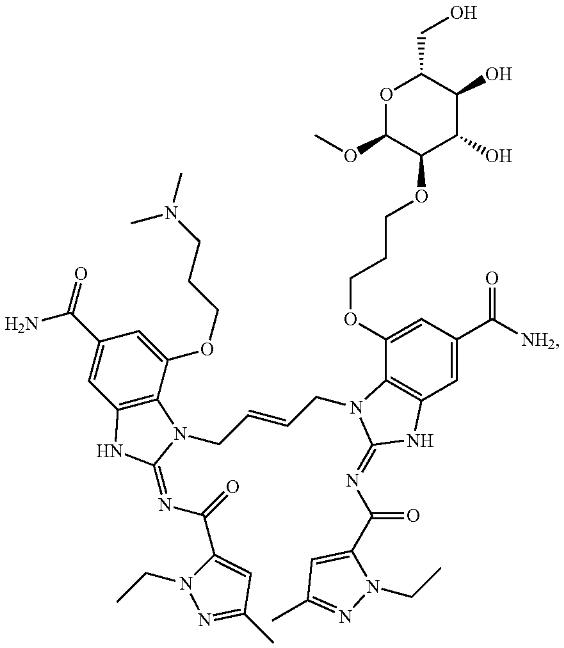
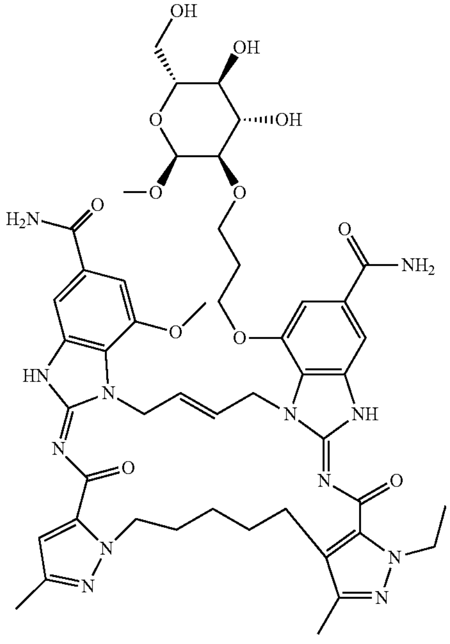
,
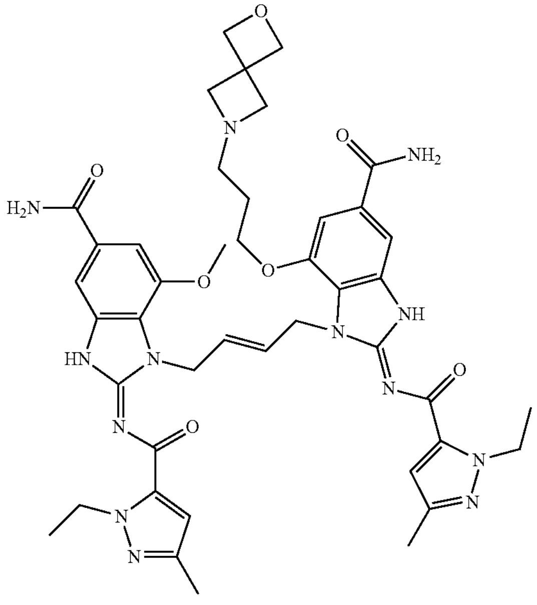
, -continued

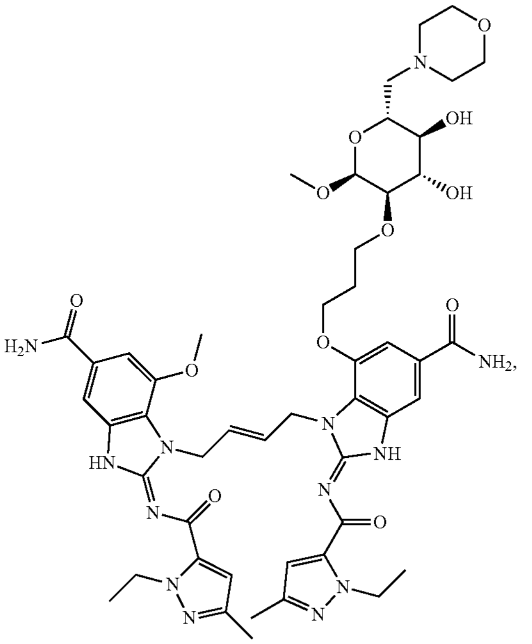

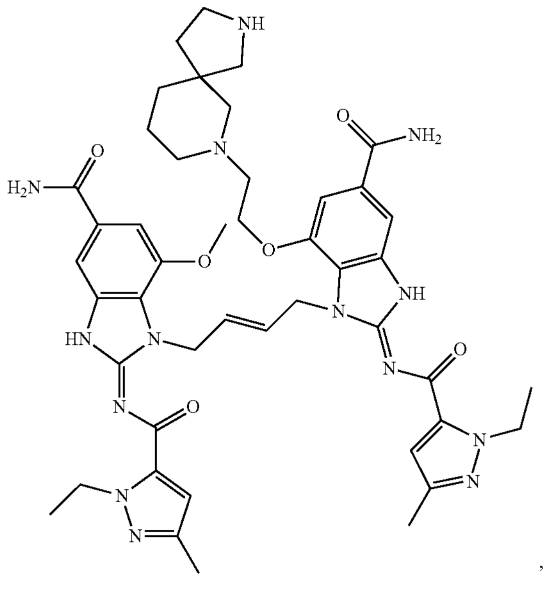 [SMILES: CCn1nc(C)cc1C(=O)/N=c1/[nH]c2cc(C(N)=O)cc(OC)c2n1C/C=C/Cn1/c(=N/C(=O)c2cc(C)nn2CC)[nH]c2cc(C(N)=O)cc(OCCN3CCCC4(CCNC4)C3)c21]

,

-continued

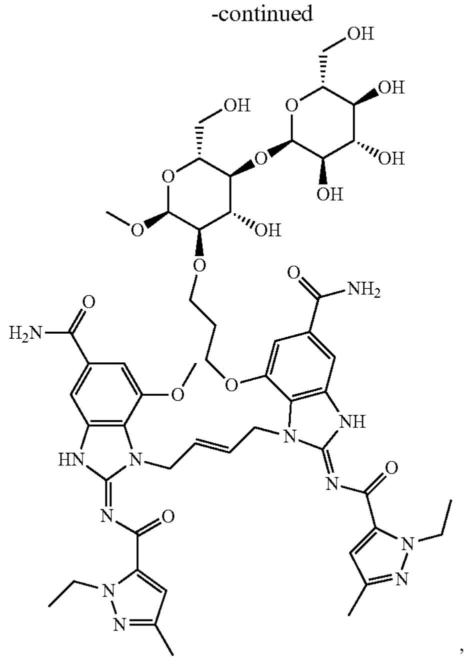

, and

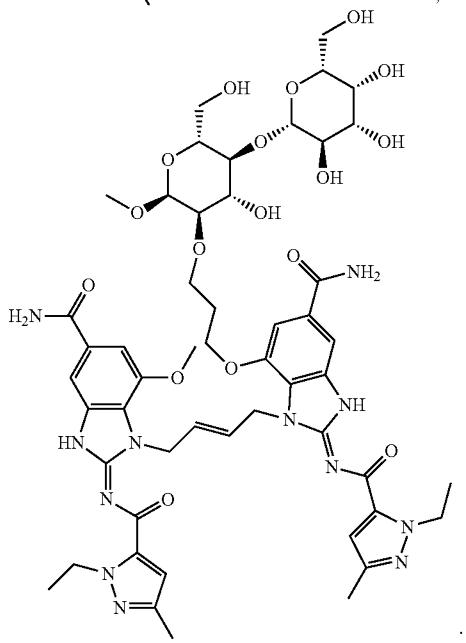

.

13. A pharmaceutical composition, comprising the compound or the pharmaceutically acceptable salt thereof according to claim 1.

14. A method for the treatment of a STING-mediated disease or a STING-mediated tumor complication in a subject in need thereof, comprising administering the compound or the pharmaceutically acceptable salt thereof according to claim 1 to the subject, wherein the STING-mediated disease comprises a disease selected from the group consisting of cancer, inflammation, infectious diseases and immune-related diseases.

15. The method according to claim 14, wherein the cancer is selected from the group consisting of adrenocortical carcinoma, anal carcinoma, anorectal carcinoma, anal canal carcinoma, appendiceal carcinoma, cerebellar astrocytoma, cerebral astrocytoma, basal cell carcinoma, skin carcinoma (non-melanoma), biliary tract carcinoma, extrahepatic bile duct carcinoma, intrahepatic bile duct carcinoma, bladder carcinoma, osteoarticular carcinoma, osteosarcoma, malignant fibrous histiocytoma, brain carcinoma, brain tumors, brain stem glioma, ependymoma, medulloblastoma, visual pathway and hypothalamic gliomas, breast carcinoma, bronchial adenoma, nervous system carcinoma, nervous system lymphoma, central nervous system carcinoma, central nervous system lymphoma, cervical carcinoma, chronic lymphocytic leukemia, chronic myelogenous leukemia, chronic myeloproliferative disease, colon carcinoma, colorectal carcinoma, cutaneous T-cell lymphoma, lymphoid tumors, granuloma fungoides, Sezary syndrome, endometrial carcinoma, esophageal carcinoma, extracranial germ cell tumors, extragonadal germ cell tumors, eye carcinoma, intraocular melanoma, retinoblastoma, gallbladder carcinoma, gastric carcinoma, gastrointestinal carcinoids, gastrointestinal stromal tumors (GIST), germ cell tumors, ovarian germ cell tumors, head and neck carcinoma, hepatocellular carcinoma, Hodgkin lymphoma, islet cell tumors, Kaposi's sarcoma, kidney carcinoma, laryngeal carcinoma, acute lymphocytic leukemia, acute myelogenous leukemia, hairy cell leukemia, lip and oral cavity carcinoma, liver carcinoma, lung carcinoma, non-small-cell lung carcinoma, small cell lung carcinoma, non-Hodgkin's lymphoma, primary central nervous system lymphoma, Waldenstrom macroglobulinemia, melanoma, mesothelioma, metastatic squamous carcinoma, tongue carcinoma, multiple endocrine tumor syndrome, myelodysplastic syndrome, multiple myeloma, nasopharyngeal carcinoma, neuroblastoma, oropharyngeal carcinoma, ovarian carcinoma, ovarian epithelial carcinoma, ovarian low malignant potential tumors, pancreatic carcinoma, pancreatic islet cell pancreatic carcinoma, sinus and nasal cavity carcinoma, parathyroid carcinoma, penile carcinoma, pharyngeal carcinoma, pheochromocytoma, pinealoma, pituitary tumors, plasma cell tumors, pleuropulmonary blastoma, prostate carcinoma, rectal carcinoma, renal pelvis and ureter transitional cell carcinoma, retinoblastoma, rhabdomyosarcoma, salivary gland carcinoma, Ewing's sarcoma, Kaposi's sarcoma, synovial sarcoma, uterine carcinoma, uterine sarcoma, small intestine carcinoma, soft tissue sarcoma, squamous cell carcinoma, supratentorial primitive neuroectodermal tumors, testicular carcinoma, throat carcinoma, thymoma, urinary tract carcinoma, endometriosis, vaginal carcinoma, vulval carcinoma, and Wilm's tumors.

16. The method according to claim 14, wherein the STING-mediated tumor complication is selected from malignant pleural effusion and ascites.

* * * * *